US012064442B2

(12) United States Patent
Khairatkar-Joshi et al.

(10) Patent No.: US 12,064,442 B2
(45) Date of Patent: *Aug. 20, 2024

(54) TREATMENT OF ALLERGIC RHINITIS USING A COMBINATION OF MOMETASONE AND OLOPATADINE

(71) Applicant: GLENMARK SPECIALTY S.A., La Chaux-de-Fonds (CH)

(72) Inventors: Neelima Khairatkar-Joshi, Thane (IN); Abhay Kulkarni, Navi Mumbai (IN); Dinesh Pradeep Wale, Maharashtra (IN); Vikram M. Bhosale, Mumbai (IN); Piyush Agarwal, Mumbai (IN); Patrick Keohane, London (GB); Sudeesh K. Tantry, Jamison, PA (US); Chad Oh, San Francisco, CA (US)

(73) Assignee: GLENMARK SPECIALTY S.A., Neuchâtel (CH)

( * ) Notice: Subject to any disclaimer, the term of this patent is extended or adjusted under 35 U.S.C. 154(b) by 101 days.

This patent is subject to a terminal disclaimer.

(21) Appl. No.: 17/807,487

(22) Filed: Jun. 17, 2022

(65) Prior Publication Data
US 2022/0387452 A1 Dec. 8, 2022

Related U.S. Application Data

(63) Continuation of application No. 17/003,584, filed on Aug. 26, 2020, now Pat. No. 11,400,101, which is a continuation of application No. 15/903,597, filed on Feb. 23, 2018, now Pat. No. 10,758,550, which is a continuation-in-part of application No. 15/842,063, filed on Dec. 14, 2017, now Pat. No. 10,653,661, which is a continuation-in-part of application No. 15/716,661, filed on Sep. 27, 2017, now abandoned, which is a continuation-in-part of application No. 15/691,500, filed on Aug. 30, 2017, now abandoned, which is a continuation-in-part of application No. 15/636,120, filed on Jun. 28, 2017, now Pat. No. 10,016,443, which is a continuation-in-part of application No. 14/682,001, filed on Apr. 8, 2015, now Pat. No. 10,548,907, which is a continuation-in-part of application No. 14/506,122, filed on Oct. 3, 2014, now Pat. No. 10,646,500.

(30) Foreign Application Priority Data

Oct. 4, 2013 (IN) .......................... 3174/MUM/2013

(51) Int. Cl.
| | | |
|---|---|---|
| *A61K 31/58* | (2006.01) | |
| *A61K 9/00* | (2006.01) | |
| *A61K 31/335* | (2006.01) | |
| *A61K 31/573* | (2006.01) | |
| *A61M 11/00* | (2006.01) | |
| *A61M 15/08* | (2006.01) | |
| *A61P 11/02* | (2006.01) | |
| *A61P 27/14* | (2006.01) | |
| *A61P 37/08* | (2006.01) | |

(52) U.S. Cl.
CPC ............ *A61K 31/58* (2013.01); *A61K 9/0043* (2013.01); *A61K 31/335* (2013.01); *A61K 31/573* (2013.01); *A61P 11/02* (2018.01); *A61P 27/14* (2018.01); *A61P 37/08* (2018.01); *A61M 11/007* (2014.02); *A61M 15/08* (2013.01)

(58) Field of Classification Search
CPC .... A61K 31/335; A61K 31/573; A61K 31/58; A61K 9/0043; A61M 11/007; A61M 15/009; A61M 15/08; A61P 11/02; A61P 27/14; A61P 37/08
See application file for complete search history.

(56) References Cited

U.S. PATENT DOCUMENTS

| | | | |
|---|---|---|---|
| 4,871,865 | A | 10/1989 | Lever et al. |
| 4,923,892 | A | 5/1990 | Lever et al. |
| 5,062,549 | A | 11/1991 | Smith et al. |
| 5,837,699 | A | 11/1998 | Sequeira et al. |
| 6,127,353 | A | 10/2000 | Yuen et al. |
| 6,841,146 | B2 | 1/2005 | Haslwanter et al. |
| 7,811,606 | B2 | 10/2010 | Chaudry |
| 7,977,376 | B2 | 7/2011 | Singh et al. |
| 8,399,508 | B2 | 3/2013 | Singh et al. |
| 9,078,923 | B2 | 7/2015 | Dhuppad et al. |
| 2004/0097474 | A1 | 5/2004 | Cagle et al. |
| 2005/0158247 | A1 | 7/2005 | Veronesi et al. |

(Continued)

FOREIGN PATENT DOCUMENTS

| | | |
|---|---|---|
| EP | 2014305 A1 | 1/2009 |
| KR | 101304341 B1 | 9/2013 |

(Continued)

OTHER PUBLICATIONS

Kaiser (Clinical Review, Olopatadine HCl Nasal Spray, 2008). (Year: 2008).*

(Continued)

*Primary Examiner* — Umamaheswari Ramachandran
(74) *Attorney, Agent, or Firm* — Blank Rome LLP

(57) ABSTRACT

The present invention relates to a method of treating allergic rhinitis in a subject (e.g., a pediatric human subject) in need thereof comprising nasally administering to the subject an effective amount of a fixed-dose pharmaceutical composition comprising mometasone or its salt and olopatadine or its salt.

18 Claims, 3 Drawing Sheets

(56) References Cited

U.S. PATENT DOCUMENTS

| | | |
|---|---|---|
| 2006/0110328 A1 | 5/2006 | Cagle et al. |
| 2007/0099883 A1 | 5/2007 | Calis et al. |
| 2007/0233012 A1 | 10/2007 | Lerrick et al. |
| 2008/0058296 A1 | 3/2008 | Chaudry |
| 2010/0276457 A1 | 11/2010 | Petit et al. |
| 2011/0082145 A1 | 4/2011 | Schneider et al. |
| 2011/0257115 A1 | 10/2011 | Leighton |
| 2012/0121653 A1 | 5/2012 | Jenkins et al. |
| 2015/0099725 A1 | 4/2015 | Khairatkar-Joshi et al. |
| 2015/0250718 A1* | 9/2015 | Dhuppad ............... A61K 47/38 514/171 |
| 2016/0287612 A1 | 10/2016 | Dhuppad et al. |
| 2017/0333449 A1 | 11/2017 | Khairatkar-Joshi et al. |
| 2018/0000843 A1 | 1/2018 | Dhuppad et al. |

FOREIGN PATENT DOCUMENTS

| | | |
|---|---|---|
| UA | 124500 C2 | 9/2021 |
| WO | 9222320 A1 | 12/1992 |
| WO | 1995020393 A1 | 8/1995 |
| WO | 2001026658 A1 | 4/2001 |
| WO | 0157079 A2 | 8/2001 |
| WO | 0189984 A1 | 11/2001 |
| WO | 2004043470 A1 | 5/2004 |
| WO | 2004100982 A1 | 11/2004 |
| WO | 2006057769 A2 | 6/2006 |
| WO | 2007026151 A1 | 3/2007 |
| WO | 2009003199 A1 | 12/2008 |
| WO | 2010009028 A1 | 1/2010 |
| WO | 2010025236 A1 | 3/2010 |
| WO | 2011008923 A2 | 1/2011 |
| WO | 2011141929 A2 | 11/2011 |
| WO | 2012094283 A2 | 7/2012 |
| WO | 2014092346 A1 | 6/2014 |
| WO | 2015049665 A1 | 4/2015 |

OTHER PUBLICATIONS

Anonymous, "Product Monograph Including Patient Medication Information—RYALTRIS (olopatadine hydrochloride and mometasone furoate nasal spray)", XP093025504, Retrieved from the Internet: URL: https://pdf.hres.ca/dpd_pm/00067564.PDF, Sep. 21, 2022.
Patel, Piyush, et al., "Effect of olopatadine-mometasone combination nasal spray on seasonal allergic rhinitis symptoms in an environmental exposure chamber study", Ann Allergy Asthma Immunol, 2019, 122:160-166, XP085589177, 8 pages.
Amrol, et al., Intranasal Steroids for Ocular Symptoms in Allergic Rhinitis, http://www.jwatch.org/w201006100000003/2010/06/10/intranasal-steroids-ocular-symptoms allergic.
Aneeza et al., Allergy Rhinol, 2013, 4:e120-e126.
Anolik R., Allergy Asthma Proc, 2009, 30:406-412.
Anolik R., Int Arch Allergy Immunol, 2008, 147:323-330.
Anolik, et al., Clinical Benefits of Combination Treatment with Mometasone Furoate Nasal Spray and Loratadine vs Monotherapy with Mometasone Furoate in the Treatment of Seasonal Allergic Rhinitis, Ann Allergy Asthma Immunol., 2008, 100:264-271.
Anonymous: NCT02631551 on May 18, 2017: Clinical Trials.gov Archive, May 18, 2017 (May 18, 2017), XP055444418, Retrieved from the Internet: URL:https://clinicaltrials.gov/archive/NCT02631551/ 2017 05 18 [retrieved on Jan. 25, 2018].
Anonymous: NCT02870205 on May 3, 2017: ClinicalTrials.gov Archive, May 3, 2017 (May 3, 2017), XP055444415, Retrieved from the Internet: URL:https://clinicaltrials.gov/archive/NCT02870205/ 2017 05 03 [retrieved on Jan. 25, 2018] the whole document.
Anonymous: To Study GSP 301 in Patients With Seasonal Allergic Rhinitis—Study Results—ClinicalTrials.gov, Jun. 28, 2017 (Jun. 28, 2017), XP055445229, Retrieved from the Internet: URL:https://www.clinicaltrials.gov/ct2/show/results/NCT02318303?term=NCT02318303&rank=I =X4370156#othr [retrieved on Jan. 26, 2018] the whole document.
Austin, et al., Mometasone Furoate is a less specific Glucocorticoid than Fluticasone Propionate, European Respiratory Journal, 2002, 20:1386-1392.
Bajaj et al., The Internet Journal of Otohinolaryngology, 2006, vol. 6, No. 1.
Barnes, et al., Effects of Levocetirizine as Add-on Therapy to Fluticasone in Seasonal Allergic Rhinitis, Clinical and Experimental Allergy, 2006, 36:676-684.
Benincasa, et al., Evaluation of Fluticasone Propionate Aqueous Nasal Spray Taken Alone and in Combination with Cetirizine in the Prophylactic Treatment of Seasonal Allergic Rhinitis, Drug Invest. 1994, 8:4:225-233.
Bernstein et al., Respiratory Medicine, 1999, 93:603-612.
Bousquet, et al., Onset of Action of the Fixed Combination Intranasal Azelastine-Fluticasone Propionate in an Allergen Exposure Chamber, J Allergy Clin Immunol Pract, 2018, 1-7.e6 (13 pgs).
Buck, "Intranasal steroids for children with allergic rhinitis", Pediatric Pharmacology, May 2001, vol. 7, No. 5.
ClinicalTrials (Clinicaltrials.gov, firs! posted Aug. 17, 2016, last update posted May 4, 2017).
Derendorf et al., Eur Respir J, 2001, 17:157-158.
Di Lorenzo, et al., Randomized Placebo-controlled Trial Comparing Fluticasone Aqueous Nasal Spray in Mono-therapy, Fluticasone Aqueous Nasal Spray in Mono-therapy, Fluticasone Plus Cetirizine, Fluticasone Plus Montelukast and Cetirizine Plus Montelukast for Seasonal Allergic Rhinitis, Clin Exp Allergy, 2004, 34:259-267.
Dibildox, J Allergy Clin Immunol, 108(1):S54-S58.
E.P. Terekhova, Allergic Rhinitis: Modern Methods of Treatment, 0.21518/2079-701X-2016-17-74-79, 2016, p. 74-79, 7 pages (with partial English translation).
Glenmark Pharmaceuticals: Glenmark Pharmaceuticals Reports Positive Results from a Phase 3 Trial of GSP 301, Mar. 29, 2017 (Mar. 29, 2017), XP055444412, Retrieved from the Internet: URL:https://www.prnewswire.com/news-releases/glenmark-pharmaceuticals-reports-positive-results-from-a-phase-3-trial-of-gsp-301-mometasoneolopatadine-fixed-dose-combination-nasal-spray-in-seasonal-allergic-rhinitis-300431125.html [retrieved on 2018-01-25] the whole document.
Herbert et al., Allergy, 1996, 51:569-576.
International Search Report for International Application No. PCT/IB2015/065035 dated Jan. 9, 2015.
International Search Report for International Application PCT/IB2014/064251, Dated Nov. 14, 2014, pp. 1-13.
International Search Report issued in PCT/IB2019/051465 dated May 21, 2019.
Johnson, M. Ph.D., Development of Fluticasone Propionate and Comparison with other Inhaled Corticosteroids, J. Allergy Clin. Immunol, 1998, 101:4:2:S434-S439.
Juniper, et al., Comparison of Beclomethasone Dipropionate Aqueous Nasal Spray, Astemizole, and the Combination in the Prophylatic Treatment of Ragweed Pollen-induced Rhinoconjunctivits, J Allergy Clin Immunol, 1989, 83:627-33.
Kagawa, et al., Synergetic Effects of Prednisiline and olo[atadine on atopic dermatituts model of hairless mice, Pharmacology, 2010, 85:5:286-294 (English Abstract).
Kaliner et al: Azelastine and olopatadine in the treatment of allergic rhinitis, Annals of Allergy, Asthma & Immunology, Arlington Heights, IL, US, vol. 103, No. 5, Nov. 1, 2009 (Nov. 1, 2009), pp. 373-380, XP026960456, ISSN: 1081-1206 [retrieved on Nov. 1, 2009] the whole document.
LaForce et al., Allergy Asthma Proc, 2010, 31:132-140.
Maiti et al. (J of Pharmacology and Pharmacotherapeutics, Oct.-Dec. 2011, 2(4), 270-276).
Meltzer et al., Ann Allergy Asthma Immunol, 2005, 95:600-606.
Meltzer et al. (J Allergy Clin Immunol, Jul. 1998).
Meltzer et al., J Allergy Clin Immunol, 1999, 104(1):107-114.
Navarro et al., J Investig Allergol Clin Immunol, 2011, 21(5):363-369.
Nsouli, et al., Combination of a Nasal Antihistamine Olopatadine and a Nasal Corticosteroid, Mometasone . . . , International Scientific Conference, Dubai, UAE, Dec. 2010.
Okubo et al. (Current Medical Research and Opinion, 2010, 1657-1665).

(56) References Cited

OTHER PUBLICATIONS

Patel (Annals of Allergy, Asthma & Immunology, vol. 117, Issue 5, Supplement, Nov. 2016, p. S114-115).
PR Newswire (http://www.prnewswire.com/news-releases/glenmark-pharmaceuticals-reports-positive-results-from-a-phase-3-trial-of-gsp-301-mometasoneolopatadine-fixed-dose-combination-nasal-spray-in-seasonal-allergic-rhinitis-300431125.html), Mar. 29, 2017.
Prenner, et al., Mometasone Furoate Nasal Spray Reduces the Ocular Symptoms of Seasonal Allergic Rhinitis, J Allergy Clin Immunol, Jun. 2010, 1247-1253.
Prescribing information for Nasonex® (Jan. 2011).
Prescribing information for Patanase® (Feb. 2012).
Ratner et al., J Fam Pract. 1998, 47(2): 118-25.
Ratner, et al., Ann. Allergy Asthma Immunol, 2005, 95:474-479.
Roland, Expert Opin Pharmacother, 2010, 11(9), 1559-1567.
Simpson, Ann Allergy, 1994, 73:497-502.
Supplementary European Search Report issued in EP18823894 on Apr. 8, 2019.
U.S. Appl. No. 14/483,837, filed Sep. 11, 2014.
"NASONEX®", [Online publication]. URL: https://web.archive.org/web/20170210075036/https://www.accessdata.fda.gov/drugsatfda_docs/label/2004/20762s007lbl.pdf.

\* cited by examiner

TREATMENT OF ALLERGIC RHINITIS USING A COMBINATION OF MOMETASONE AND OLOPATADINE

This patent application is a continuation application of U.S. patent application Ser. No. 17/003,584, filed Aug. 26, 2020, which is a continuation of U.S. patent application Ser. No. 15/903,597, filed Feb. 23, 2018, which is a continuation-in-part application of U.S. patent application Ser. No. 15/842,063, filed Dec. 14, 2017, which is a continuation-in-part application of U.S. patent application Ser. No. 15/716,661, filed Sep. 27, 2017, which is a continuation-in-part of U.S. patent application Ser. No. 15/691,500, flied Aug. 30, 2017, which is a continuation-in-part of U.S. patent application Ser. No. 15/636,120, filed Jun. 28, 2017, which is a continuation-in-part of U.S. patent application Ser. No. 14/682,001, filed Apr. 8, 2015, which is a continuation-in-part of U.S. patent application Ser. No. 14/506,122, filed Oct. 3, 2014, which claims the benefit of Indian Provisional Patent Application number 3174/MUM/2013, filed Oct. 4, 2013, each of which is hereby incorporated by reference in its entirety.

TECHNICAL FIELD OF THE INVENTION

The present patent application relates to a method of treating allergic rhinitis in a subject (preferably a human) by administering a combination of mometasone or its salt and olopatadine or its salt.

BACKGROUND OF THE INVENTION

Allergic rhinitis is a medical term for inflammation and irritation of the mucous membrane inside the nose. It generally occurs when an allergen such as pollen, dust, or animal dander (particles of shed skin and hair) is inhaled by an individual with a sensitized immune system. Allergic rhinitis may cause additional symptoms such as rhinorrhea (excess nasal secretion), sneezing, nasal itching, nasal congestion and obstruction, coughing, headache, fatigue and malaise. Symptoms may vary in severity between individuals.

Many treatment options are available for treating allergic rhinitis such as, for example, antihistamines (e.g., cetirizine and loratadine), steroids (e.g., triamcinolone), deconges- tants, and leukotriene receptor antagonists (e.g., montelu- kast). These treatments are generally administered orally or nasally and some are associated with unpleasant taste and smell (e.g., Dymista® nasal spray, which is a combination of azelastine and fluticasone propionate).

Olopatadine hydrochloride, an antihistamine, is chemically described as (Z)-11-[3-(dimethylamino)propylidene]-6,11-dihydrodibenz[b,e]oxepin-2-acetic acid hydrochloride, and is disclosed in U.S. Pat. Nos. 4,871,865 and 4,923,892. It is commercially available in the United States as PATA-NASE® Nasal Spray, which contains 0.6% w/v olopatadine (base) in a non-sterile aqueous solution. It is indicated for the relief of the symptoms of seasonal allergic rhinitis (SAR) in adults and children 6 years of age and older. PATA-NASE® was found to have an onset of action of 30 minutes after dosing in the environmental exposure unit (Ref: USFDA approved label for Patanase).

Mometasone furoate is a glucocorticosteroid used topically to reduce inflammation of the skin or in the airways. Mometasone furoate monohydrate is commercially available in the United States as NASONEX®, a nasal spray indicated for (i) the treatment of nasal symptoms of allergic rhinitis in patients ≥2 years of age, (ii) the treatment of nasal congestion associated with seasonal allergic rhinitis in patients ≥2 years of age, (iii) the prophylaxis of seasonal allergic rhinitis in patients ≥12 years of age, and (iv) the treatment of nasal polyps in patients ≥18 years of age. It is available as 50 mcg in a metered-dose, manual pump spray unit containing an aqueous suspension of mometasone furoate monohydrate equivalent to 0.05% w/w mometasone furoate (calculated on the anhydrous basis).

International Publication No. WO 2011/141929 discloses an aqueous nasal spray solution comprising fluticasone and olopatadine.

U.S. Pat. No. 6,127,353 discloses a pharmaceutical composition of mometasone furoate monohydrate.

U.S. Pat. Nos. 7,977,376 and 8,399,508 disclose a topical formulation of olopatadine hydrochloride.

International Publication No. WO 2011/008923 discloses a nasal spray regimen of olopatadine for children.

International Publication No. WO 1995/020393 discloses the use of mometasone furoate for treating airway passage and lung diseases.

International Publication No. WO 2010/025236 discloses a combination of a nasal steroid and a nasal antihistamine for the treatment of viral upper respiratory tract infections, upper respiratory infections, and common colds.

Allergic rhinitis is an uncomfortable ailment and affects the quality of life of allergy sufferers. A fast onset of action would be highly desirable to provide quick relief from the symptoms of allergic rhinitis. There exists a need for therapies which provide a fast onset of action, preferably in less than 30 minutes.

SUMMARY OF THE INVENTION

The present invention relates to a fixed dose combination of mometasone or its salt and olopatadine or its salt and its use for the treatment of rhinitis in a subject in need thereof. The inventors have surprisingly found that mometasone furoate and olopatadine hydrochloride act synergistically in the treatment of allergic rhinitis and the combination is more effective and provides better therapeutic value than treatment with either active ingredient alone.

The inventors have also surprisingly found that nasal administration of a pharmaceutical composition of mometasone or a salt thereof (such as mometasone furoate) and olopatadine or a salt thereof (such as olopatadine hydrochloride) provides a faster onset of action of relief of symptoms associated with allergic rhinitis, such as seasonal allergic rhinitis or perennial allergic rhinitis, when compared to olopatadine hydrochloride monotherapy or mometasone fuorate monotherapy. In particular, the pharmaceutical composition provides faster relief of nasal symptoms, such as nasal congestion, rhinorrhea, itching and sneezing. The pharmaceutical composition may also provide a faster onset of action of ocular symptoms, such as ocular itching, tearing/watery eyes and ocular redness. The onset of action may be less than 30 minutes, such as within about 15 minutes, such as within about 10 minutes. In an embodiment, the present invention relates to a method of treating allergic rhinitis in a subject (e.g., a human) in need thereof comprising nasally administering to the subject an effective amount of a fixed-dose pharmaceutical composition comprising mometasone or its salt and olopatadine or its salt. Preferably, the composition is nasally administered as 1 or 2 sprays per nostril of the subject at least once daily. Each spray preferably comprises mometasone or its salt and olopatadine or its salt in a weight ratio of about 1:5 to about 1:60, such as in a weight ratio of from about 1:12 to about 1:53, from about 1:13.3 to about 1:50, or from about 1:18 to about 1:40 (based on the equivalent weight of olopatadine free base). In one embodiment, the fixed-dose pharmaceutical composition is a suspension wherein the mometasone or its salt is present in particulate form and the olopatadine or its salt is present in dissolved form.

In another embodiment, the present invention relates to a method of treating allergic rhinitis in a subject (e.g., a human) in need thereof comprising nasally administering to the subject an effective amount of a fixed-dose pharmaceutical composition comprising mometasone furoate monohydrate and olopatadine hydrochloride. In one preferred embodiment, the composition is nasally administered as 1 or 2 sprays per nostril of the subject at least once daily. Each spray of the pharmaceutical composition may comprise olopatadine hydrochloride equivalent to about 300 mcg, about 450 mcg, about 600 mcg, about 750 mcg, or about 900 mcg of olopatadine, and about 12.5 mcg, about 25 mcg, about 37.5 mcg, about 50 mcg, or about 62.5 mcg of mometasone furoate. In one embodiment, each spray comprises olopatadine hydrochloride equivalent to about 600 mcg of olopatadine and about 25 mcg of mometasone furoate. In another embodiment, each spray comprises olopatadine hydrochloride equivalent to about 600 mcg of olopatadine and about 50 mcg of mometasone furoate.

Allergic rhinitis in the context of present invention includes, but is not limited to, inflammation and irritation of the mucous membrane inside the nose, and nasal and/or non-nasal symptoms associated therewith. It includes, for example, persistent allergic rhinitis, perennial allergic rhinitis, seasonal allergic rhinitis, chronic rhinitis, rhinitis medicamentosa, vasomotor rhinitis, infective rhinitis, autonomic rhinitis, hormonal rhinitis, drug-induced rhinitis, atrophic rhinitis, and gustatory rhinitis. Preferably, the allergic rhinitis is selected from perennial allergic rhinitis, persistent allergic rhinitis, seasonal allergic rhinitis, and nasal and/or non-nasal symptoms associated therewith.

In the context of the present invention, symptoms associated with rhinitis includes rhinorrhea, nasal congestion, nasal itching, sneezing, itching/burning eyes, tearing/watering eyes, redness of eyes, itching of ears or palate, coughing, ocular pruritus, excess lacrimation, headache, fatigue and malaise.

In another embodiment, of the present invention relates to a method of treating allergic rhinitis in a subject (e.g., a human) in need thereof, the method comprising nasally administering to the subject an effective amount of a fixed-dose pharmaceutical composition comprising mometasone or its salt and olopatadine or its salt in a weight ratio of about 1:5 to about 1:60 or from about 1:12 to about 1:53, wherein (i) the composition is nasally administered as 1 or 2 sprays per nostril, once or twice daily, and (ii) each spray comprises olopatadine hydrochloride equivalent to about 600 mcg of olopatadine and about 25 mcg to about 50 mcg of mometasone furoate. In one embodiment, the composition is administered for about 1 week. In another aspect of the embodiment, the composition is administered for about 2 weeks.

In one embodiment, the total nasal symptoms score (TNSS) of the human subject is reduced by at least 40%, preferably by at least 50% from baseline after 1 or 2 weeks treatment. In another embodiment, the total ocular symptom score (TOSS) of the human subject is reduced by at least 30%, preferably by at least 40% from baseline after 1 or 2 weeks treatment. In an aspect of the invention, the total nasal symptoms score (TNSS) and the total ocular symptom score (TOSS) can be observed as instantaneous or reflective or both.

Yet another embodiment is a method of treating symptoms associated with allergic rhinitis in a human subject in need thereof comprising nasally administering twice daily, two sprays per nostril of a fixed-dose pharmaceutical composition comprising mometasone or its salt (e.g., mometasone furoate) and olopatadine its salt (e.g., olopatadine hydrochloride). Each spray may comprise mometasone or its salt and olopatadine or its salt in a weight ratio of about 1:5 to about 1:60 (such as a weight ratio of about 1:12 to about 1:53, about 1:13.3 to about 1:50, or from about 1:18 to about 1:40) (based on the equivalent weight of olopatadine free base) (for example, each spray comprises about 12.5 mcg, about 25 mcg, about 37.5 mcg, about 50 mcg, or about 62.5 mcg of mometasone or its salt (such as about 50 mcg mometasone furoate) and olopatadine hydrochloride equivalent to about 300 mcg, about 450 mcg, about 600 mcg, about 750 mcg, or about 900 mcg of olopatadine (such as about 665 mcg olopatadine hydrochloride)). The administration may provide relief from one or more symptoms of allergic rhinitis (such as nasal symptoms or ocular symptoms) faster (e.g., an onset of action in less than 30 minutes, such as within about 15 minutes, such as within 10 minutes) than nasal administration of the mometasone or its salt or the olopatadine or its salt alone. In another embodiment, the administration may provide relief from one or more symptoms of allergic rhinitis (such as nasal symptoms) in a subject exposed to an environmental exposure chamber (EEC) (such as one with ragweed pollen at a concentration of 3500±500 particles/m$^3$ for 6 hours) faster (e.g., an onset of action in less than 15 minutes, such as within about 10 minutes) than nasal administration of the mometasone or its salt or the olopatadine or its salt alone.

Yet another embodiment is a method for providing faster onset of relief of symptoms associated with allergic rhinitis in a human subject in need thereof comprising nasally administering twice daily, two sprays per nostril of a fixed-dose pharmaceutical composition comprising mometasone or its salt (e.g., mometasone furoate) and olopatadine its salt (e.g., olopatadine hydrochloride). This method may provide faster onset of relief of one or more symptoms compared to administration of the mometasone or its salt alone or olopatadine or its salt alone. Each spray may comprise mometasone or its salt and olopatadine or its salt in a weight ratio of about 1:5 to about 1:60 (such as a weight ratio of about 1:12 to about 1:53, about 1:13.3 to about 1:50, or from about 1:18 to about 1:40) (based on the equivalent weight of olopatadine free base) (for example, each spray comprises about 12.5 mcg, about 25 mcg, about 37.5 mcg, about 50 mcg, or about 62.5 mcg of mometasone or its salt (such as about 50 mcg mometasone furoate) and olopatadine hydrochloride equivalent to about 300 mcg, about 450 mcg, about 600 mcg, about 750 mcg, or about 900 mcg of olopatadine (such as about 665 mcg olopatadine hydrochloride)). The administration may provide relief from one or more symptoms within 30 minutes, such as within 15 minutes or 10 minutes. In another embodiment, the administration may provide relief from one or more symptoms of allergic rhinitis (such as nasal symptoms) in a subject exposed to an environmental exposure chamber (EEC) (such as one with ragweed pollen at a concentration of 3500±500 particles/m3 for 6 hours) in less than 15 minutes, such as within about 10 minutes.

The human subject may previously been treated with mometasone or its salt alone or olopatadine or its salt alone.

In such human subjects, the methods described herein may include the step of discontinuing treatment with the monotherapy of mometasone or its salt or olopatadine or its salt prior to initiating nasal administration of the fixed dose pharmaceutical composition of mometasone or its salt and olopatadine or its salt.

In one embodiment, the methods herein provide faster onset of action for relief of nasal symptoms in the subject. In another embodiment, the methods herein provide faster onset of action for relief of ocular symptoms in the subject.

In one preferred embodiment, the method comprises nasally administering to a human subject twice daily, two sprays per nostril of a fixed-dose pharmaceutical composition comprising 25 mcg mometasone furoate and 665 mcg olopatadine hydrochloride.

In one embodiment, the pharmaceutical composition provides faster onset of action for relief of nasal symptoms in the subject. In another embodiment, the pharmaceutical composition provides faster onset of action for relief of ocular symptoms in the subject.

Yet another embodiment is a method of treating a human subject suffering from allergic rhinitis comprising the step of administering to the subject a pharmaceutical composition for twice daily nasal administration of two sprays per nostril, wherein (i) the pharmaceutical composition provides an onset of action within 15 minutes for the treatment of allergic rhinitis and (ii) each spray of the pharmaceutical composition comprises about 25 mcg of mometasone furoate and about 665 mcg of olopatadine hydrochloride.

Yet another embodiment is a method of treating a human subject suffering from allergic rhinitis comprising the steps of:
  (a) prescribing to a subject (e.g., a human subject) a fixed-dose pharmaceutical composition for twice daily nasal administration of two sprays per nostril, wherein the fixed-dose pharmaceutical composition comprises mometasone or its salt (such as mometasone furoate) and olopatadine or its salt (such as olopatadine hydrochloride), and each spray comprises mometasone or its salt and olopatadine or its salt in a weight ratio of about 1:5 to about 1:60 (such as a weight ratio of about 1:12 to about 1:53, about 1:13.3 to about 1:50, or from about 1:18 to about 1:40) (based on the equivalent weight of olopatadine free base) (for example, each spray comprises about 12.5 mcg, about 25 mcg, about 37.5 mcg, about 50 mcg, or about 62.5 mcg of mometasone or its salt (such as about 50 mcg mometasone furoate) and olopatadine hydrochloride equivalent to about 300 mcg, about 450 mcg, about 600 mcg, about 750 mcg, or about 900 mcg of olopatadine (such as about 665 mcg olopatadine hydrochloride)),
  the prescribing being performed in response to (i) marketing of the pharmaceutical composition as (A) providing faster onset of action (such as an onset of action within less than 30 minutes, such as within 15 minutes, such as within 10 minutes) for relief of one or more symptoms (e.g., nasal symptoms) of allergic rhinitis than nasal administration of mometasone or its salt (such as 25 or 50 mcg mometasone furoate) or olopatadine or its salt (such as 665 mcg olopatadine hydrochloride) alone, (B) providing relief of one or more symptoms of allergic rhinitis within 15 minutes (or 30 minutes), and (ii) diagnosis of the human subject as suffering from allergic rhinitis, or (C) providing faster onset of action (such as within 15 minutes, such as within about 10 minutes) for relief of one or more symptoms (e.g., nasal symptoms) of allergic rhinitis in subjects exposed to an environmental exposure chamber (EEC) (such as one with ragweed pollen at a concentration of 3500±500 particles/$m^3$ for 6 hours) than nasal administration of the mometasone or its salt or the olopatadine or its salt alone. (D) providing relief from one or more symptoms of allergic rhinitis (such as nasal symptoms) in subjects exposed to an environmental exposure chamber (EEC) (such as one with ragweed pollen at a concentration of 3500±500 particles/$m^3$ for 6 hours) within 15 minutes, such as within about 10 minutes; and
  (b) administering the prescribed pharmaceutical composition to the subject. In one preferred embodiment, each spray of the fixed-dose pharmaceutical composition provides 25 mcg mometasone furoate and 665 mcg olopatadine hydrochloride.

Yet another embodiment is a method of treating a human subject suffering from allergic rhinitis (such as seasonal allergic rhinitis or perennial allergic rhinitis) comprising the step of administering to the subject a prescribed fixed-dose pharmaceutical composition for twice daily nasal administration of two sprays per nostril, where the fixed-dose pharmaceutical composition comprises mometasone or its salt (such as mometasone furoate) and olopatadine or its salt (such as olopatadine hydrochloride), and each spray comprises mometasone or its salt and olopatadine or its salt in a weight ratio of about 1:5 to about 1:60 (such as a weight ratio of about 1:12 to about 1:53, about 1:13.3 to about 1:50, or from about 1:18 to about 1:40) (based on the equivalent weight of olopatadine free base) (for example, each spray comprises about 12.5 mcg, about 25 mcg, about 37.5 mcg, about 50 mcg, or about 62.5 mcg of mometasone or its salt (such as about 50 mcg mometasone furoate) and olopatadine hydrochloride equivalent to about 300 mcg, about 450 mcg, about 600 mcg, about 750 mcg, or about 900 mcg of olopatadine (such as about 665 mcg olopatadine hydrochloride)). The pharmaceutical composition is prescribed in response to (a) marketing of the pharmaceutical composition as (A) providing faster onset of action (such as an onset of action within less than 30 minutes, such as within 15 minutes, such as within 10 minutes) for relief of symptoms (e.g., nasal symptoms) of allergic rhinitis than nasal administration of mometasone or its salt (such as 50 mcg mometasone furoate) or olopatadine or its salt (such as 665 mcg olopatadine hydrochloride) alone or (B) providing relief of one or more symptoms of allergic rhinitis within 15 minutes (or 30 minutes), and (b) a diagnosis of the subject as suffering from allergic rhinitis. In one preferred embodiment, each spray of the fixed-dose pharmaceutical composition provides 25 mcg mometasone furoate and 665 mcg olopatadine hydrochloride.

In one embodiment of any of the methods described herein, the allergic rhinitis is selected from perennial allergic rhinitis, persistent allergic rhinitis, seasonal allergic rhinitis, and nasal and/or non-nasal symptoms associated therewith. In one preferred embodiment, of any of the methods described herein, the allergic rhinitis is seasonal allergic rhinitis. In another preferred embodiment, of any of the methods described herein, the allergic rhinitis is perennial allergic rhinitis.

In one embodiment, the subject suffers from persistent allergic rhinitis and is treated for 4 or 6 weeks.

In another embodiment, the subject exhibits a positive skin prick test to an allergen. Alternately, the subject may also exhibit positive blood tests showing an allergy.

In yet another embodiment, the method involves no significant treatment-related adverse effects in the subject after 1 or 2 weeks treatment.

In another embodiment, the present invention relates to a method of treating seasonal allergic rhinitis and/or nasal symptoms associated with seasonal allergic rhinitis in a subject (e.g., a human) in need thereof comprising nasally administering to the subject a combination (e.g., synergistic combination) comprising mometasone furoate and olopatadine hydrochloride, wherein the combination is in the form of a pharmaceutical composition comprising mometasone furoate and olopatadine hydrochloride in a weight ratio of about 1:5 to about 1:60 or from about 1:13.3 to about 1:53.2 (based on the equivalent weight of olopatadine free base). In one embodiment, the present invention relates to a method of treating allergic rhinitis in a human in need thereof comprising nasally administering to the human an effective amount of a fixed-dose pharmaceutical composition comprising mometasone or its salt and olopatadine or its salt, wherein (i) the composition is nasally administered as 1 or 2 sprays per nostril of the human at least once daily, and (ii) each spray comprises mometasone or its salt and olopatadine or its salt in a weight ratio of about 1:5 to about 1:60 or from about 1:13.3 to about 1:53.2 (based on the equivalent weight of olopatadine free base). The method may provide reduction in at least one treatment-related adverse effect (e.g. epistaxis and somnolence) relative to the use of the mometasone or olopatadine alone. For example, the method may provide effective treatment of seasonal allergic rhinitis and/or nasal symptoms associated with seasonal allergic rhinitis in a subject with a reduced incidence of drowsiness and nose bleeds. In another embodiment, the method may provide effective treatment of seasonal allergic rhinitis and/or nasal symptoms associated with seasonal allergic rhinitis in a subject without significant drowsiness and/or inducing nose bleeds.

In another embodiment, the present invention relates to a method of treating perennial allergic rhinitis and/or nasal symptoms associated with perennial allergic rhinitis in a subject (e.g., a human) in need thereof comprising nasally administering to the subject a combination (e.g., synergistic combination) comprising mometasone furoate and olopatadine hydrochloride, wherein the combination is in the form of a pharmaceutical composition comprising mometasone furoate and olopatadine hydrochloride in a weight ratio of about 1:5 to about 1:60 or from about 1:13.3 to about 1:53.2 (based on the equivalent weight of olopatadine free base).

In one aspect of this embodiment, each spray comprises about 25 mcg or about 50 mcg mometasone furoate and olopatadine hydrochloride equivalent to about 600 mcg olopatadine. In one aspect of this embodiment, the pharmaceutical composition is a suspension comprising mometasone or its salt in particulate form and olopatadine or its salt in solution. In one aspect of this embodiment, the composition is administered for a period of at least 1 week as—(i) 1 spray per nostril once daily or twice daily, or (ii) 2 sprays per nostril once daily or twice daily. In yet another aspect of this embodiment, the allergic rhinitis is selected from perennial allergic rhinitis, persistent allergic rhinitis, seasonal allergic rhinitis, and nasal and/or non-nasal symptoms associated therewith. In a preferred aspect, the allergic rhinitis is seasonal allergic rhinitis and/or nasal symptoms associated therewith. In yet another aspect of this embodiment, (i) the total nasal symptoms score (TNSS) of the human is reduced by at least 50% from baseline after 2 weeks treatment, and/or (ii) total ocular symptom score (TOSS) of the human is reduced by at least 40% from baseline after 2 weeks treatment, and/or (iii) no significant treatment-related adverse effects are observed in the human after 2 weeks treatment. In one aspect of the said embodiment, the human exhibits a positive skin prick test to an allergen. In one embodiment, the treatment-related adverse effects include somnolence or epistaxis or a combination thereof.

The fixed-dose pharmaceutical composition comprising mometasone or its salt and olopatadine or its salt may be administered to the subject according to one of the following regimens:

a) the composition is nasally administered as 1 spray per nostril once daily for a period of at least 1 week;
b) the composition is nasally administered as 2 sprays per nostril once daily for a period of at least 1 week;
c) the composition is nasally administered as 1 spray per nostril twice daily for a period of at least 1 week;
d) the composition is nasally administered as 2 sprays per nostril twice daily for a period of at least 1 week;
e) the composition is nasally administered as 1 spray per nostril once daily for a period of 2 weeks;
f) the composition is nasally administered as 2 sprays per nostril once daily for a period of 2 weeks;
g) the composition is nasally administered as 1 spray per nostril twice daily for a period of 2 weeks; or
h) the composition is nasally administered as 2 sprays per nostril twice daily for a period of 2 weeks.

In another embodiment of any of the methods described herein, the subject is a pediatric subject (e.g., ≥2 to <12 years of age, such as ≥6 to <12 years of age or ≥6 months to <6 years of age) and the fixed-dose pharmaceutical composition is nasally administered 1 spray per nostril twice daily. In one embodiment, each spray of the fixed-dose pharmaceutical composition provides 665 mcg olopatadine hydrochloride and 25 mcg mometasone furoate (e.g., with the formulation of Example 9). In yet another embodiment, the composition is nasally administered for a period of at least 1 week, such as for a period of at least 2 weeks, for a period of at least 4 weeks, for a period of at least 8 weeks or for a period of at least 12 weeks. In one embodiment, the subject is 2 to under 12 years of age. In another embodiment, the subject is 6 to under 12 years of age. In yet another embodiment, the subject is 2 to under 6 years of age.

Yet another embodiment is a method of treating symptoms associated with allergic rhinitis in a pediatric human subject (e.g., ≥2 to <12 years of age, such as ≥6 to <12 years of age or ≥6 months to <6 years of age) in need thereof comprising twice daily nasal administration of a single dose of a pharmaceutical composition comprising mometasone furoate and olopatadine hydrochloride, where a single dose of the composition provides about 1330 mcg olopatadine hydrochloride and about 50 mcg mometasone furoate. In one preferred embodiment, a single dose comprises one spray per nostril of a pharmaceutical composition, where each spray provides 665 mcg olopatadine hydrochloride and 25 mcg mometasone furoate (e.g., with the formulation of Example 9). The allergic rhinitis can be, for example, seasonal allergic rhinitis or perennial allergic rhinitis. In one embodiment, the subject is 2 to under 12 years of age. In another embodiment, the subject is 6 to under 12 years of age. In yet another embodiment, the subject is 2 to under 6 years of age.

Yet another embodiment is a method of treating symptoms associated with allergic rhinitis in a pediatric human subject (e.g., ≥2 to <12 years of age, such as ≥6 to <12 years of age or ≥6 months to <6 years of age) in need thereof comprising nasally administering twice daily, one spray per nostril of a fixed-dose pharmaceutical composition comprising mometasone furoate and olopatadine hydrochloride, where each spray provides 665 mcg olopatadine hydrochloride and 25 mcg mometasone furoate (e.g., with the formulation of Example 9). The allergic rhinitis can be, for example, seasonal allergic rhinitis or perennial allergic rhinitis. In one embodiment, the subject is 2 to under 12 years of age. In another embodiment, the subject is 6 to under 12 years of age. In yet another embodiment, the subject is 2 to under 6 years of age.

In another embodiment, the present invention relates to a method of treating seasonal allergic rhinitis and/or nasal symptoms associated with seasonal allergic rhinitis in a human in need thereof comprising nasally administering to the human a combination (e.g., synergistic combination) comprising mometasone furoate and olopatadine hydrochloride, wherein the combination is in the form of a pharmaceutical composition comprising mometasone furoate in particulate form and olopatadine hydrochloride in solution in a weight ratio of about 1:13.3 to about 1:53.2 (based on the equivalent weight of olopatadine free base), and wherein the composition is administered as 1 or 2 sprays per nostril of the human, at least once daily for a period of at least 1 week wherein the method provides reduction of at least one treatment-related adverse effect.

In one aspect of this embodiment, the composition is administered once daily or twice daily for a period of 2 weeks. In another aspect of this embodiment, each spray comprises about 25 mcg or about 50 mcg of mometasone furoate and about 665 mcg of olopatadine hydrochloride. In yet another aspect of this embodiment, (i) the total nasal symptoms score (TNSS) of the human is reduced by at least 50% from baseline after 2 weeks treatment, and/or (ii) total ocular symptom score (TOSS) of the human is reduced by at least 40% from baseline after 2 weeks treatment, and/or (iii) no significant treatment-related adverse effects are observed in the human after 2 weeks treatment. In one aspect of the said embodiment, the human exhibits a positive skin prick test to an allergen. Preferably, the treatment-related adverse effects include somnolence or epistaxis or a combination thereof.

In an aspect of the invention, the fixed-dose pharmaceutical composition may be administered for a period of about 1 week, 2 weeks, 4 weeks, 6 weeks or 8 weeks. Preferably, the fixed-dose pharmaceutical composition, is administered as 1 or 2 sprays per nostril of the subject (e.g., a human), once daily or twice daily for a period of 1 week or 2 weeks. In another aspect of the embodiment, each spray of the composition comprises olopatadine hydrochloride equivalent to about 600 mcg of olopatadine and about 25 mcg to about 50 mcg of mometasone furoate. Preferably, each spray of the composition comprises about 665 mcg of olopatadine hydrochloride (equivalent to about 600 mcg of olopatadine) and about 25 mcg or about 50 mcg of mometasone furoate. In yet another aspect, the composition does not have unpleasant odor and taste. In yet another aspect of the embodiment, the total nasal symptoms score (TNSS) of the human subject is reduced by at least 40% or at least 50% from baseline after 1 or 2 weeks treatment. In yet another aspect of the embodiment, the total ocular symptom score (TOSS) of the human is reduced by at least 30% or at least 40% from baseline after 1 or 2 weeks treatment. In yet another aspect of the embodiment, the said method provides reduction in one or more treatment-related adverse effects. Preferably, the treatment-related adverse effects include somnolence or epistaxis or a combination thereof. In yet another aspect of the embodiment, the human subject is a patient exhibiting a positive skin prick test to an allergen.

In one aspect the present invention relates to the use of mometasone or its salt and olopatadine or its salt in a weight ratio of about 1:5 to about 1:60 or from about 1:12 to about 1:53 for the manufacture of a fixed-dose pharmaceutical composition of the invention for the treatment of allergic rhinitis in a subject (e.g., a human) in need thereof. In an aspect, the fixed-dose pharmaceutical composition is a suspension wherein mometasone or its salt is present in particle form (e.g., having a mean particle size of from about 1 to about 20 μm, or from about 1 to about 15 μm) and olopatadine or its salt is present in dissolved form. In yet another aspect the composition does not have unpleasant odor and taste.

In a separate embodiment the present invention relates to a method of reducing symptoms associated with rhinitis in a subject (e.g. a human) in need thereof, the method comprising nasally administering to the subject an effective amount of a fixed dose pharmaceutical composition comprising mometasone or its salt and olopatadine or its salt in a weight ratio of about 1:5 to about 1:60 or from about 1:12 to about 1:53 for about 1 or 2 weeks.

In yet another embodiment, the present invention relates to a method of reducing symptoms associated with allergic rhinitis in a human in need thereof comprising nasally administering to the human an effective amount of a fixed-dose pharmaceutical composition comprising mometasone or its salt and olopatadine or its salt, wherein (i) the composition is nasally administered as 1 or 2 sprays per nostril of the human at least once daily, and (ii) each spray comprises mometasone or its salt and olopatadine or its salt in a weight ratio of about 1:5 to about 1:60 or from about 1:12 to about 1:53 for about 1 or 2 weeks (based on the equivalent weight of olopatadine free base) and wherein the composition is administered as 1 or 2 sprays per nostril of the human, at least once daily for a period of at least 1 week, wherein the method provides reduction of at least one adverse event. In one aspect of this embodiment, each spray comprises about 25 mcg or about 50 mcg mometasone furoate and olopatadine hydrochloride equivalent to about 600 mcg olopatadine. In one aspect of this embodiment, the pharmaceutical composition is a suspension comprising mometasone or its salt in particulate form and olopatadine or its salt in solution. In one aspect of this embodiment, the composition is administered for a period of at least 1 week as—(i) 1 spray per nostril once daily or twice daily, or (ii) 2 sprays per nostril once daily or twice daily. In yet another aspect of this embodiment, the allergic rhinitis is selected from perennial allergic rhinitis, persistent allergic rhinitis, seasonal allergic rhinitis, and nasal and/or non-nasal symptoms associated therewith. In a preferred aspect, the allergic rhinitis is seasonal allergic rhinitis and/or nasal symptoms associated therewith. In yet another aspect of this embodiment, (i) the total nasal symptoms score (TNSS) of the human is reduced by at least 50% from baseline after 2 weeks treatment, and/or (ii) total ocular symptom score (TOSS) of the human is reduced by at least 40% from baseline after 2 weeks treatment, and/or (iii) no significant treatment-related adverse effects are observed in the human after 2 weeks treatment. In one aspect of the said embodiment, the human exhibits a positive skin prick test to an allergen. In one aspect of the said embodiment, the symptoms includes rhinorrhea, nasal congestion, nasal itching, sneezing, itching/burning eyes, tearing/watering eyes, redness of eyes, itching of ears or palate, coughing, ocular pruritus, excess lacrimation, headache, fatigue and malaise.

In yet another aspect of the embodiment, the treatment-related adverse effects include somnolence or epistaxis or a combination thereof.

Another embodiment relates to a method of reducing eosinophil count in the nasal lavage of a subject by nasally administering an effective amount of a fixed-dose pharmaceutical composition comprising mometasone or its salt and olopatadine or its salt in a weight ratio of about 1:5 to about 1:60 (based on the equivalent weight of olopatadine free base), wherein the method provides a greater reduction in eosinophil count than that provided by mometasone or its salt or olopatadine or its salt when administered as a monotherapy. The eosinophil count can be measured by any known technique, such as with a hemocytometer.

Yet another embodiment relates to a method of reducing total cell count in the nasal lavage by nasally administering an effective amount of a fixed-dose pharmaceutical composition comprising mometasone or its salt and olopatadine or its salt in a weight ratio of about 1:5 to about 1:60 (based on the equivalent weight of olopatadine free base) wherein the method provides a greater reduction in total cell count than that provided by mometasone or its salt or olopatadine or its salt when administered as a monotherapy.

In another aspect, the present invention relates to a stable fixed dose, aqueous pharmaceutical composition for nasal administration to a human. The composition comprises mometasone or its salt and olopatadine or its salt. The pharmaceutical composition may be contained within a container suitable for nasal administration. In one embodiment, the pharmaceutical composition is contained within a spray bottle (such as a sprayer). The spray bottle may include a container for storing the pharmaceutical composition and a pump for spraying the pharmaceutical composition intranasally. In one embodiment, the container is capable of storing 30, 56, 60, or 120, or 240 doses. For example, a container storing 240 doses can provide a 1 month supply of the pharmaceutical composition (2 sprays per nostril twice daily (8 sprays per day) for 30 days). A container storing 56 doses can provide a 1 week supply of the pharmaceutical composition (2 sprays per nostril twice daily (8 sprays per day) for 7 days). In one embodiment, the container may be suitable for containing 9-10 mL (e.g., 9 mL or 56 doses), 18-19 mL of the pharmaceutical composition (e.g., 18 mL or 120 doses), or 29-30 mL (e.g., 29 mL or 240 doses) of the pharmaceutical composition.

One embodiment is a stable fixed dose, aqueous pharmaceutical composition (e.g., contained in a container) for nasal administration to a human, where the composition comprises about 0.001% w/w to about 0.075% w/w mometasone or its salt and about 0.5% w/w to about 0.8% w/w olopatadine or its salt. The pharmaceutical composition may be in the form of a solution or a suspension, but preferably the composition is in the form of a suspension (more preferably, a single phase suspension), wherein mometasone or its salt is present in particle form and olopatadine or its salt is present in dissolved form. In one aspect, the mometasone or its salt and olopatadine or its salt are present in a weight ratio of about 1:3 to about 1:106, or from about 1:5 to about 1:53, or preferably from about 1:5 to about 1:36.

The composition preferably also includes a hydrocolloid. In one embodiment, the composition is a suspension and includes a hydrocolloid in a sufficient amount to prevent or inhibit phase separation (i.e., separation of the particles and solution) after 3 or 6 months of storage at 25±2° C. and 60%±5% relative humidity (RH) or at 40±2° C. and 75%±5% RH. In one embodiment, the aqueous pharmaceutical composition is a single phase suspension which remains a single phase suspension even after 3 or 6 months of storage at 25±2° C. and 60%±5% RH or at 40±2° C. and 75%±5% RH.

Another embodiment is a stable fixed dose, aqueous pharmaceutical composition (e.g., contained in a container) for nasal administration to a human, where the composition comprises about 0.001% w/w to about 0.075% w/w mometasone furoate monohydrate and about 0.5 w/w to about 0.8% w/w olopatadine hydrochloride.

Yet another embodiment is a stable fixed dose, aqueous pharmaceutical suspension composition (e.g., contained in a container) for nasal administration to a human, where the composition comprises about 0.025% w/w to about 0.05% w/w mometasone or its salt, about 0.6% w/w to about 0.7% w/w olopatadine or its salt and a hydrocolloid.

Yet another embodiment is a stable fixed dose, aqueous pharmaceutical suspension composition (e.g., contained in a container) for nasal administration to a human, where the composition comprises about 0.025% w/w to about 0.05% w/w mometasone or its salt, about 0.6% w/w to about 0.7% w/w olopatadine or its salt and a hydrocolloid which includes carboxymethylcellulose sodium and xanthan gum. The hydrocolloid may be present at a concentration of at least about 0.1% w/w of the composition.

One embodiment is a stable fixed dose, aqueous pharmaceutical suspension composition (e.g., contained in a container) for nasal administration to a human, comprising about 0.025% w/w to about 0.05% w/w mometasone furoate, about 0.6% w/w to about 0.7% w/w olopatadine hydrochloride and a hydrocolloid, where the hydrocolloid is xanthan gum. The xanthan gum may be present at a concentration of at least about 0.1% w/w, or preferably between about 0.1% w/w to about 3% w/w of the composition.

Another embodiment is a stable fixed dose, aqueous pharmaceutical suspension composition (e.g., contained in a container) for nasal administration to a human, comprising about 0.025% w/w to about 0.05% w/w mometasone furoate, about 0.6% w/w to about 0.7% w/w olopatadine hydrochloride and a hydrocolloid, where the hydrocolloid comprises sodium carboxymethyl cellulose. The sodium carboxymethyl cellulose may be present at a concentration of at least about 0.1% w/w, or preferably between about 0.1% w/w to about 3% w/w of the composition.

Yet another embodiment is a stable fixed dose aqueous pharmaceutical composition in the form of suspension (e.g., contained in a container) for nasal administration to a human, comprising mometasone or its pharmaceutically acceptable salt, olopatadine or its pharmaceutically acceptable salt, a hydrocolloid at a concentration of at least about 0.1% w/w of the composition and a pharmaceutical acceptable excipient.

Suitable pharmaceutical acceptable excipients include, but are not limited to, chelating agents, preservatives, buffers, surfactants, isotonicity agents, taste masking agents, antioxidants, humectants, pH adjusting agents, and mixtures thereof.

In one embodiment, the pharmaceutical composition has a pH between about 3.3 and about 4.1, or between about 3.5 and about 3.9, or between about 3.5 to about 3.7. The inventors discovered that the olopatadine hydrochloride crystallizes out of the fixed dose combination aqueous suspension at a pH of 5 to 5.5. The olopatadine hydrochloride, however, remains dissolved in the aqueous suspension at a pH of about 3.3 to about 4.1.

The aqueous pharmaceutical composition preferably is substantially free of crystals of olopatadine hydrochloride. In one embodiment, the aqueous pharmaceutical composition contains less than 2%, less than 1%, less than 0.5%, less than 0.2%, or less than 0.1% of crystalline olopatadine hydrochloride, based on the 100% total weight of olopatadine hydrochloride in the composition. In another embodiment, the aqueous pharmaceutical composition is substantially free of crystals of olopatadine hydrochloride after 3 or 6 months of storage at 25±2° C. and 60%±5% RH or at 40±2° C. and 75%±5% RH. In yet another embodiment, the aqueous pharmaceutical composition contains less than 2%, less than 1%, less than 0.5%, less than 0.2%, or less than 0.1% of crystalline olopatadine hydrochloride, based on the 100% total weight of olopatadine hydrochloride in the composition, after 3 or 6 months of storage at 25±2° C. and 60%±5% RH or at 40±2° C. and 75%±5% RH.

The osmolality of the pharmaceutical composition may range between about 200 mOsm/kg to about 400 mOsm/kg, or about 250 mOsm/kg to about 350 mOsm/kg.

The viscosity of the pharmaceutical composition may range from about 10 cps to about 200 cps or preferably from about 20 cps to about 150 cps. In one embodiment, the composition has a viscosity of from about 60 to about 150 cps, such as from about 90 to about 150 cps or from about 100 to about 150 cps. In another embodiment, the composition has a viscosity of from about 20 to about 60 cps.

In yet another aspect, the pharmaceutical composition is in the form of suspension and contains mometasone furoate in particles having a mean particle size in the range of from about 1 μm to about 20 μm, or preferably from about 1 μm to about 15 μm. In an aspect, the suspension pharmaceutical composition of the present invention has mean particle size of less than 15 μm when determined by microscopy technique.

In yet another aspect, the pharmaceutical composition, upon nasal administration (e.g., as a nasal spray) of a dose equivalent to 200 mcg of mometasone or its salt to a human, results in (a) an area under the curve $(AUC)_{0-\infty}$ for mometasone or its salt of about 50 pg·hr/mL to about 140 pg·hr/mL, preferably from about 68 pg·hr/mL to about 124 pg·hr/mL, (b) a $C_{max}$ for mometasone or its salt of about 6.5 pg/mL to about 16 pg/ml, preferably from about 8.6 pg/mL to about 12.9 pg/ml, (c) a $T_{max}$ for mometasone or its salt of about 15 minutes to about 120 minutes, or (d) any combination of any of the foregoing. In yet another aspect, the pharmaceutical composition, upon nasal administration (e.g., as a nasal spray) of a dose equivalent to 2400 mcg of olopatadine or its salt to a human, results in (a) an $AUC_{0-\infty}$ for olopatadine or its salt of about 42.5 ng·hr/mL to about 116.5 ng·hr/mL, preferably from about 56.7 ng·hr/mL to about 99.8 ng·hr/mL, (b) a $C_{max}$ for olopatadine or its salt of about 10.3 ng/mL to about 24.1 ng/ml, preferably from about 13.8 ng/mL to about 20.7 ng/ml, (c) a $T_{max}$ of about 15 minutes to about 120 minutes, or (d) any combination of any of the foregoing.

In yet another aspect, the pharmaceutical composition, upon nasal administration (e.g., as a nasal spray) of a dose equivalent to 100 mcg of mometasone or its salt (e.g., mometasone furoate) to a human for the first time, results in (a) an area under the curve $(AUC)_{tau}$ for mometasone or its salt of about 12 pg·hr/mL to about 73 pg·hr/mL, preferably from about 20 pg·hr/mL to about 36 pg·hr/mL, (b) a $C_{max}$ for mometasone or its salt of about 3 pg/mL to about 13 pg/ml, preferably from about 5 pg/mL to about 9 pg/ml, (c) a $T_{max}$ for mometasone or its salt of about 15 minutes to about 120 minutes, or (d) any combination of any of the foregoing. In yet another aspect, the pharmaceutical composition, upon nasal administration (e.g., as a nasal spray) of a dose equivalent to 100 mcg of mometasone or its salt (e.g., mometasone furoate) to a human at steady state (e.g., after 8 days of twice daily administration of 100 mcg of mometasone or its salt), results in (a) an area under the curve $(AUC)_{tau}$ for mometasone or its salt of about 26 pg·hr/mL to about 124 pg·hr/mL, preferably from about 40 pg·hr/mL to about 80 pg·hr/mL, (b) a $C_{max}$ for mometasone or its salt of about 4 pg/mL to about 16 pg/ml, preferably from about 8 pg/mL to about 12 pg/ml, (c) a $T_{max}$ for mometasone or its salt of about 15 minutes to about 120 minutes, or (d) any combination of any of the foregoing.

In yet another aspect, the pharmaceutical composition, when delivered as a nasal spray has spray characteristics comprising a spray pattern having a longest axis of about 15-75 mm, a shortest axis of about 10-65 mm, and an ellipticity of about 1-2.

Another embodiment is a stable fixed dose pharmaceutical composition in the form of a suspension (e.g., contained in a container) for nasal administration to a human, comprising mometasone furoate monohydrate, olopatadine hydrochloride and a hydrocolloid which comprises xanthan gum at a concentration of about 0.3% w/w of the composition, wherein the composition has a pH between about 3.5 to about 3.9.

Yet another embodiment is a stable fixed dose pharmaceutical composition in the form of suspension (e.g., contained in a container) for nasal administration to a human, comprising mometasone furoate monohydrate, olopatadine hydrochloride and a hydrocolloid which comprises sodium carboxymethyl cellulose at a concentration of about 0.5% w/w of the composition, wherein the composition has a pH between about 3.5 to about 3.9.

In a further embodiment, the stable fixed dose, aqueous pharmaceutical composition is contained in a sprayer, and on delivering a spray of the composition to a human nose results in a spray pattern having a longest axis of 15-75 mm, a shortest axis of 10-65 mm, and an ellipticity of 1-2.

One embodiment is a stable fixed dose, aqueous pharmaceutical composition comprising mometasone furoate monohydrate, olopatadine hydrochloride and optionally a hydrocolloid contained in a sprayer, wherein each spray of the aqueous pharmaceutical composition provides (i) mometasone furoate monohydrate equivalent to about 50 mcg of mometasone furoate and (ii) olopatadine hydrochloride equivalent to about 600 mcg olopatadine.

Yet another embodiment is a stable fixed dose, aqueous pharmaceutical composition comprising mometasone furoate monohydrate, olopatadine hydrochloride and optionally a hydrocolloid contained in a sprayer, wherein each spray of the aqueous pharmaceutical composition provides (i) mometasone furoate monohydrate equivalent to about 25 mcg of mometasone furoate and (ii) olopatadine hydrochloride equivalent to about 600 mcg olopatadine.

In an embodiment, the present invention relates to a stable fixed dose pharmaceutical aqueous suspension composition (e.g., contained in a container) for nasal administration to a human, where the composition comprises (1) about 0.025% w/w mometasone furoate monohydrate, (2) about 0.665% w/w olopatadine hydrochloride, (3) a hydrocolloid selected from about 0.3% w/w of xanthan gum and about 0.5% w/w carboxymethyl cellulose sodium (4) about 0.02% w/w benzalkonium chloride, (5) about 0.4% w/w sodium chloride, (6) about 0.01% w/w di-sodium edetate, (7) about 0.94% w/w sodium phosphate heptahydrate, and (8) about 0.01% w/w polysorbate 80.

Another embodiment is a stable fixed dose pharmaceutical aqueous suspension composition (e.g., contained in a container) for nasal administration to a human, where the composition comprises (1) about 0.050% w/w mometasone furoate monohydrate, (2) about 0.665% w/w olopatadine hydrochloride, (3) a hydrocolloid selected from about 0.3% w/w of xanthan gum and about 0.5% w/w carboxymethyl cellulose sodium, (4) about 0.02% w/w benzalkonium chloride, (5) about 0.4% w/w sodium chloride, (6) about 0.01% w/w di-sodium edetate, (7) about 0.94% w/w sodium phosphate heptahydrate, and (8) about 0.01% w/w polysorbate 80.

Yet another embodiment is a stable fixed dose pharmaceutical aqueous suspension composition (e.g., contained in a container) for nasal administration to a human, where the composition comprises (1) about 0.025% w/w mometasone furoate monohydrate, (2) about 0.665% w/w olopatadine hydrochloride, (3) a hydrocolloid selected from about 0.3% w/w of xanthan gum and about 0.5% w/w carboxymethyl cellulose sodium, (4) about 1% w/w to about 1.2% w/w mixture of microcrystalline cellulose and carboxymethyl cellulose sodium, (5) about 0.02% w/w benzalkonium chloride, (6) about 0.4% w/w sodium chloride, (7) about 0.01% w/w di-sodium edetate, (8) about 0.94% w/w sodium phosphate heptahydrate, and (9) about 0.01% w/w polysorbate 80.

Yet another embodiment is a stable fixed dose pharmaceutical aqueous suspension composition (e.g., contained in a container) for nasal administration to a human, where the composition comprises (1) about 0.050% w/w mometasone furoate monohydrate, (2) about 0.665% w/w olopatadine hydrochloride, (3) a hydrocolloid selected from about 0.3% w/w of xanthan gum and about 0.5% w/w carboxymethyl cellulose sodium, (4) about 1% w/w to about 1.2% w/w mixture of microcrystalline cellulose and carboxymethyl cellulose sodium, (5) about 0.02% w/w benzalkonium chloride, (6) about 0.4% w/w sodium chloride, (7) about 0.01% w/w di-sodium edetate, (8) about 0.94% w/w sodium phosphate heptahydrate, and (9) about 0.01% w/w polysorbate 80.

Yet another embodiment is a stable suspension suitable for nasal administration to a human, comprising (a) an aqueous solvent, (b) particles of mometasone furoate suspended in the solvent, the particles having a mean particle size of from about 1 to about 20 μm, (c) olopatadine hydrochloride dissolved in the solvent, and (d) a hydrocolloid, the suspension having a viscosity in the range of about 20 cps to about 150 cps. In one preferred embodiment, the suspension has a pH of about 3.5-3.9, and osmolality in the range of about 250 mOsm/kg to about 350 mOsm/kg. In one embodiment, the suspension further comprises a chelating agent, a preservative, a buffer, a surfactant, an isotonicity agent, and optionally a pH adjusting agent.

Preferably, the suspensions of the present invention have only one phase (i.e., they are preferably a single phase suspension).

In a further embodiment, the present invention relates to a stable fixed dose, aqueous pharmaceutical composition (e.g., contained in a container) for nasal administration comprising about 0.025% w/w to about 0.05% w/w mometasone or its salt and about 0.5 w/w to about 0.8% w/w olopatadine or its salt for the treatment of rhinitis in a human in need thereof.

Any of the aforementioned pharmaceutical compositions comprising mometasone or a salt thereof and olopatadine (or a salt thereof may be used in the aforementioned methods, such as method of treating allergic rhinitis.

In a further embodiment, the present invention relates to a kit comprising a stable fixed dose, aqueous pharmaceutical composition contained in a container, for nasal administration and a package insert containing instructions about the use of the pharmaceutical composition.

DETAILED DESCRIPTION OF THE INVENTION

Definitions

Figure 1:
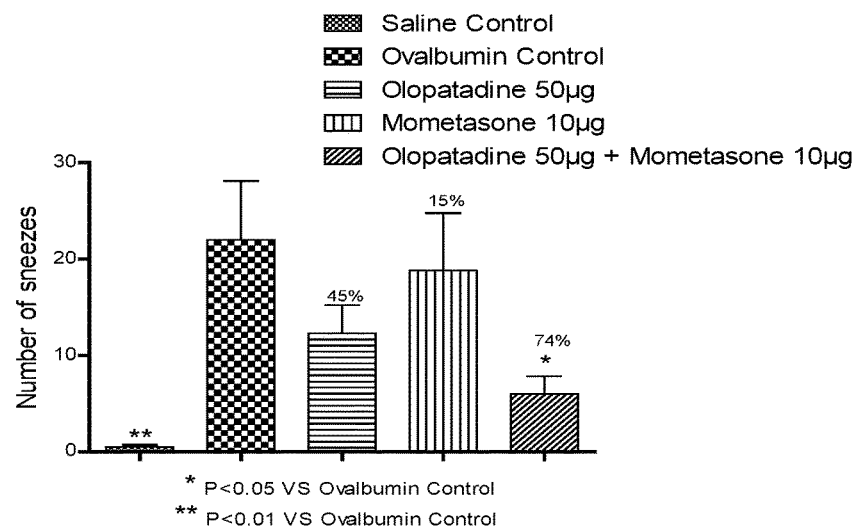
FIG. 1 is a bar graph depicting the effect of a saline control, ovalbumin control, olopatadine hydrochloride (equivalent to 50 μg olopatadine base), mometasone furoate (10 μg), and a combination of mometasone furoate (10 μg) and olopatadine hydrochloride (equivalent to 50 μg olopatadine base) on the sneezing response in guinea pigs as described in Example 1.

The terms used herein are defined as follows. If a definition set forth in the present application and a definition set forth earlier in a provisional application from which the present applications claims priority are in conflict, the definition in the present application shall control the meaning of the terms.

The "onset of action" is the point at which patients might reasonably expect to see a meaningful decrease in their allergic rhinitis symptoms (such as a meaningful decrease in reflective total nasal symptom score (rTNSS), instantaneous total nasal symptom score (iTNSS) or reflective total ocular symptom score (rTOSS)). Statistically, it is the first time point after initiation of treatment when the drug demonstrates a change greater than the placebo treatment from baseline in the primary efficacy endpoint. This statistically significant difference between drug and placebo is maintained for some period (e.g., for 4 hours) from this point onward. See "Guidance for Industry, Allergic Rhinitis: Clinical Development Programs for Drug Products", U.S. Department of Health and Human Services, Food and Drug Administration, Center for Drug Evaluation and Research (CDER), April 2000.

The term "faster onset of action" refers, in one embodiment, to a statistically significant faster reduction in one or more parameters associated with the treatment of allergic rhinitis in a subject, such as a statistically significant faster reduction in reflective total nasal symptom score (rTNSS), instantaneous total nasal symptom score (iTNSS) or reflective total ocular symptom score (rTOSS) of the subject.

The term "advertising" refers to notifying, informing, and/or apprising one or more individuals of information (e.g., the efficacy or time for onset of action of a pharmaceutical product for treating or reducing an indication), such as by mass media, including, but not limited to, newspaper, magazine, and internet advertisements, television commercials, and billboard signs. The term "advertising" as used herein also includes including a statement that the pharmaceutical product can treat or reduce the indication in the labeling for the pharmaceutical product.

The term "marketing" refers to the act or process of selling a product, including, but not limited to, any offer for sale or sale of a product, as well as advertising.

The term "effective amount" or "therapeutically effective amount" denotes an amount of an active ingredient that, when administered to a subject for treating allergic rhinitis, produces an intended therapeutic benefit in a subject. The term "active ingredient" (used interchangeably with "active" or "active substance" or "drug") as used herein includes mometasone or its salt and olopatadine or its salt.

By "salt" or "pharmaceutically acceptable salt", it is meant those salts and esters which are, within the scope of sound medical judgment, suitable for use in contact with the tissues of humans and lower animals without undue toxicity, irritation, and allergic response, commensurate with a reasonable benefit to risk ratio, and effective for their intended use. Representative acid additions salts include, but are not limited to, hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, furoate, succinate, tartrate, ascorbate, glucoheptonate, lactobionate, and lauryl sulphate salts. Representative alkali or alkaline earth metal salts include, but are not limited to, sodium, calcium, potassium and magnesium salts. Preferably, the mometasone salt is mometasone furoate (e.g., mometasone furoate monohydrate) and the olopatadine salt is olopatadine hydrochloride.

As used herein, the term "mometasone and its salt" also includes hydrates of mometasone and its salts, such as a monohydrate, for example mometasone furoate monohydrate.

All references to the weight of, or a weight ratio including, "olopatadine or its salt" or "olopatadine or its salts" are based on the equivalent weight of olopatadine free base, unless otherwise specified.

The term "treating" or "treatment" as used herein also covers the prophylaxis, mitigation, prevention, amelioration, or suppression of a disorder.

The term "synergistic" or "synergy" as used herein refers to a combination exhibiting an effect greater than would be expected from the sum of the effects of the individual components of the combination alone. The term "synergistic" or "synergy" with regard to the combination of mometasone or its salt with olopatadine or its salt which is used in the treatment allergic rhinitis (for example, in the form of a pharmaceutical composition, a combination product or a kit according to the invention) refers to an efficacy for the treatment of the allergic rhinitis that is greater than would be expected from the sum of their individuals effects. The advantages for the synergistic combinations of the present invention include, but are not limited to, exhibiting enhanced efficacy compared to each of the ingredients when used alone, lowering the required dose of one or more of the active ingredients of the combination, reducing the side effects of one or more of the active compounds of the combination and/or rendering one or more of the active ingredients more tolerable to the subject in need of treatment of the allergic rhinitis.

By "pharmaceutically acceptable excipients", it is meant any of the components of a pharmaceutical composition other than the actives and which are approved by regulatory authorities or are generally regarded as safe for human or animal use.

The term "subject" includes mammals like humans and other animals, such as domestic animals (e.g., household pets including cats and dogs) and non-domestic animals (such as wildlife). Preferably, the subject is a human. The human patient can be of any age. In one embodiment, the human subject is at least 2 years of age, at least 12 years of age, or at least 18 years of age. In another embodiment, the human subject is 18 to 65 years of age.

The term "allergic rhinitis" as used herein refers to an allergic and/or inflammatory disease of nasal mucosa, and includes, but is not limited to, inflammation and irritation of the mucous membrane inside the nose, and nasal and/or non-nasal symptoms associated therewith. Typically the allergic rhinitis includes persistent allergic rhinitis, perennial allergic rhinitis, seasonal allergic rhinitis, chronic rhinitis, rhinitis medicamentosa, vasomotor rhinitis, infective rhinitis, autonomic rhinitis, hormonal rhinitis, drug-induced rhinitis, atrophic rhinitis, and gustatory rhinitis. Preferably, the allergic rhinitis includes perennial allergic rhinitis, persistent allergic rhinitis, seasonal allergic rhinitis, and nasal and/or non-nasal symptoms associated therewith. More preferably, the allergic rhinitis includes seasonal allergic rhinitis, and nasal and/or non-nasal symptoms associated therewith.

In the context of present invention, the nasal and/or non-nasal symptoms associated with allergic rhinitis include, for example, sneezing, nasal itching, rhinorrhea (runny nose or excess nasal secretion), nasal congestion, coughing, ocular pruritus, excess lacrimation, headache, fatigue, and malaise.

Methods of Treatment

The present invention relates to use of a fixed dose combination of mometasone or its salt and olopatadine or its salt for the treatment of allergic rhinitis in a subject in need thereof. The inventors have surprisingly found that mometasone furoate and olopatadine hydrochloride act synergistically in the treatment of allergic rhinitis and their combination is more effective and provides better therapeutic value than treatment with either active ingredient alone.

In an embodiment, the present invention relates to a method of treating allergic rhinitis in a subject (e.g., a human) in need thereof comprising nasally administering to the subject, an effective amount of a fixed-dose pharmaceutical composition comprising mometasone or its salt and olopatadine or its salt. Preferably, the composition is nasally administered as 1 or 2 sprays per nostril of the subject at least once daily. Each spray may comprise mometasone or its salt and olopatadine or its salt in a weight ratio of about 1:5 to about 1:60, from about 1:10 to about 1:55 or from about 1:12 to about 1:53 or from about 1:13.3 to about 1:50. Preferably, the weight ratio of mometasone or its salt to olopatadine or its salt ranges from about 1:18 to about 1:40 or from about 1:24 to about 1:26.6. In an embodiment, the fixed-dose pharmaceutical composition is a suspension wherein mometasone or its salt is present in particulate form and the olopatadine or its salt is present in dissolved form.

Another embodiment relates to a method of treating allergic rhinitis in a subject (e.g., a human) in need thereof comprising nasally administering to the subject an effective amount of a fixed-dose pharmaceutical composition comprising mometasone furoate monohydrate and olopatadine hydrochloride. The composition may be nasally administered as 1 or 2 sprays per nostril of the subject at least once daily. Each spray of the pharmaceutical composition may comprise olopatadine hydrochloride equivalent to about 300 mcg, about 450 mcg, about 600 mcg, about 750 mcg, or about 900 mcg of olopatadine, and about 12.5 mcg, about 25 mcg, about 37.5 mcg, about 50 mcg, or about 62.5 mcg of mometasone furoate. In one embodiment, each spray comprises olopatadine hydrochloride equivalent to about 600 mcg of olopatadine and about 25 mcg of mometasone furoate. In another embodiment, each spray comprises olopatadine hydrochloride equivalent to about 600 mcg of olopatadine and about 50 mcg of mometasone furoate. Preferably, each spray comprises about 665 mcg of olopatadine hydrochloride (equivalent to about 600 mcg of olopatadine) and about 25 mcg or about 50 mcg of mometasone furoate.

Allergic rhinitis in the context of present invention includes, but is not limited to, inflammation and irritation of the mucous membrane inside the nose, and nasal and/or non-nasal symptoms associated therewith. It includes, for example, persistent allergic rhinitis, perennial allergic rhinitis, seasonal allergic rhinitis, chronic rhinitis, rhinitis medicamentosa, vasomotor rhinitis, infective rhinitis, autonomic rhinitis, hormonal rhinitis, drug-induced rhinitis, atrophic rhinitis, and gustatory rhinitis. Preferably, the allergic rhinitis is selected from perennial allergic rhinitis, persistent allergic rhinitis, seasonal allergic rhinitis, and nasal and/or non-nasal symptoms associated therewith.

In the context of the present invention, symptoms associated with rhinitis includes rhinorrhea, nasal congestion, nasal itching, sneezing, itching/burning eyes, tearing/watering eyes, redness of eyes, itching of ears or palate, coughing, ocular pruritus, excess lacrimation, headache, fatigue and malaise.

In another embodiment, the present invention relates to a method of treating allergic rhinitis in a subject in need thereof comprising nasally administering to the human, a fixed-dose pharmaceutical composition comprising mometasone or its salt and olopatadine or its salt in a weight ratio of about 1:5 to about 1:60 or from about 1:12 to about 1:53 or from about 1:13.3 to about 1:50, or from about 1:18 to about 1:40, wherein the composition is nasally administered as 1 or 2 sprays per nostril, once or twice daily. Each spray may comprise olopatadine hydrochloride equivalent to about 600 mcg of olopatadine and about 25 mcg to about 50 mcg of mometasone furoate. In an aspect of the embodiment, the composition is administered for about 1 week. In another aspect of the embodiment, the composition is administered for about 2 weeks.

In one embodiment, the total nasal symptoms score (TNSS) of the human subject is reduced by at least 40%, preferably by at least 50% from baseline after 1 or 2 weeks treatment. In another embodiment, the total ocular symptom score (TOSS) of the human subject is reduced by at least 30%, preferably by at least 40% from baseline after 1 or 2 weeks treatment. In an aspect of the invention, the total nasal symptoms score (TNSS) and the total ocular symptom score (TOSS) can be observed as instantaneous or reflective or both.

In the context of present invention, evaluation of total nasal symptoms scores (TNSS) include the sum of scores of nasal congestion, rhinorrhea, itching and sneezing from baseline to the end of treatment (e.g., 1 or 2 weeks). Further evaluation of the total ocular symptoms scores (TOSS) includes ocular itching, tearing/watery eyes and ocular redness from baseline to the end of treatment.

In one embodiment, the subject suffers from persistent allergic rhinitis and is treated for 4 or 6 weeks.

In another embodiment, the subject exhibits a positive skin prick test to an allergen. Alternately, the subject may also exhibit positive blood tests showing an allergy.

In yet another embodiment, the method involves no significant treatment-related adverse effects in the subject after 1 or 2 weeks treatment.

In another embodiment the present invention relates to a method of treating seasonal allergic rhinitis and/or nasal symptoms associated with seasonal allergic rhinitis in a subject (e.g., a human) in need thereof comprising nasally administering to the subject a synergistic combination comprising mometasone furoate and olopatadine hydrochloride, wherein the combination is in the form of a pharmaceutical composition comprising mometasone furoate and olopatadine hydrochloride in a weight ratio of about 1:5 to about 1:60 or from about 1:13.3 to about 1:53.2 (based on the equivalent weight of olopatadine free base).

In one embodiment, the present invention related to a method of treating allergic rhinitis in a human in need thereof comprising nasally administering to the human an effective amount of a fixed-dose pharmaceutical composition comprising mometasone or its salt and olopatadine or its salt, wherein (i) the composition is nasally administered as 1 or 2 sprays per nostril of the human at least once daily, and (ii) each spray comprises mometasone or its salt and olopatadine or its salt in a weight ratio of about 1:5 to about 1:60 or from about 1:13.3 to about 1:53.2 (based on the equivalent weight of olopatadine free base). The method may provide reduction of at least one treatment-related adverse effect (e.g. epistaxis and somnolence) relative to the use of the mometasone or olopatadine alone. For example, the method may provide effective treatment of seasonal allergic rhinitis and/or nasal symptoms associated with seasonal allergic rhinitis in a subject with a reduced incidence of drowsiness and nose bleeds. In another embodiment, the method may provide effective treatment of seasonal allergic rhinitis and/or nasal symptoms associated with seasonal allergic rhinitis in a subject without significant drowsiness and/or inducing nose bleeds.

In another embodiment, the present invention relates to a method of treating perennial allergic rhinitis and/or nasal symptoms associated with perennial allergic rhinitis in a subject (e.g., a human) in need thereof comprising nasally administering to the subject a combination (e.g., a synergistic combination) comprising mometasone furoate and olopatadine hydrochloride, wherein the combination is in the form of a pharmaceutical composition comprising mometasone furoate and olopatadine hydrochloride in a weight ratio of about 1:5 to about 1:60 or from about 1:13.3 to about 1:53.2 (based on the equivalent weight of olopatadine free base).

In one aspect of this embodiment, each spray comprises about 25 mcg or about 50 mcg mometasone furoate and olopatadine hydrochloride equivalent to about 600 mcg olopatadine. In one aspect of this embodiment, the pharmaceutical composition is a suspension comprising mometasone or its salt in particulate form and olopatadine or its salt in solution. In one aspect of this embodiment, the composition is administered for a period of at least 1 week as—(i) 1 spray per nostril once daily or twice daily, or (ii) 2 sprays per nostril once daily or twice daily. In yet another aspect of this embodiment, the allergic rhinitis is selected from perennial allergic rhinitis, persistent allergic rhinitis, seasonal allergic rhinitis, and nasal and/or non-nasal symptoms associated therewith. In a preferred aspect, the allergic rhinitis is seasonal allergic rhinitis and/or nasal symptoms associated therewith. In yet another aspect of this embodiment, (i) the total nasal symptoms score (TNSS) of the human is reduced by at least 50% from baseline after 2 weeks treatment, and/or (ii) total ocular symptom score (TOSS) of the human is reduced by at least 40% from baseline after 2 weeks treatment, and/or (iii) no significant treatment-related adverse effects are observed in the human after 2 weeks treatment. In one aspect of the said embodiment, the human exhibits a positive skin prick test to an allergen. In one aspect of the said embodiment, the treatment-related adverse effects include somnolence or epistaxis or a combination thereof.

Another embodiment is a method of treating allergic rhinitis in a subject, wherein the subject exhibits a positive skin prick test to an allergen. The skin prick test can be performed by pricking the skin with a needle or pin containing a small amount of ragweed allergen. In one embodiment, prior to administration of a combination of olopatadine and mometasone as described herein, the skin prick test was performed on the subject and resulted in a wheal diameter of at least 3 mm greater than a negative control such as saline.

The methods of treatment described herein can be administered to a subject without the subject exhibiting any significant treatment-related adverse effects, for example, after 1 or 2 weeks treatment.

The treatment related adverse effects in the context of the present invention may include, but are not limited to, eye disorders (e.g., conjunctivitis), gastrointestinal disorders (e.g., abdominal distension, diarrhoea, dyspepsia, dysphagia and gastric ulcer, haemorrhoidal haemorrhage, hyperchlorhydria, nausea and vomiting, and toothache), general disorders (e.g., fatigue, local swelling, peripheral oedema, pain and pyrexia), infections and infestations (e.g., oral herpes and upper respiratory tract infection), injury, poisoning and procedural complications, musculoskeletal and connective tissue disorders (e.g., arthralgia), nervous system disorders (e.g., disturbance in attention, dizziness, dysgeusia, somnolence and headache), reproductive system and breast disorder (e.g., dysmenorrhea) respiratory, thoracic and mediastinal disorders (e.g., epistaxis, dry throat, dyspnea, epistaxis, nasal congestion, nasal discomfort, respiratory tract haemorrhage, rhinorrhea, throat irritation, and upper-airway cough syndrome), skin and subcutaneous tissue disorders (e.g., rash and urticaria).

In another embodiment, the present invention relates to a method of treating seasonal allergic rhinitis and/or nasal symptoms associated with seasonal allergic rhinitis in a subject (e.g., a human) in need thereof comprising nasally administering to the subject a synergistic combination comprising mometasone furoate and olopatadine hydrochloride, wherein the combination is in the form of a pharmaceutical composition comprising mometasone furoate and olopatadine hydrochloride in a weight ratio of about 1:5 to about 1:60 or from about 1:13.3 to about 1:53.2 (based on the equivalent weight of olopatadine free base).

Synergistic effects for the combination of mometasone furoate and olopatadine hydrochloride can be evaluated by various methods. One method for evaluating the efficacy of an agent for treating allergic rhinitis is the ovalbumin induced rhinitis model in guinea pigs. In such models, the effect of the treatment is studied in animals sensitized and challenged with ovalbumin, followed by detailed analysis of their sneezing response using whole body plethysmography and the total number of eosinophils in a nasal lavage sample.

The fixed-dose pharmaceutical composition comprising mometasone or its salt and olopatadine or its salt may be administered to the subject according to one of the following regimens:

a) the composition is nasally administered as 1 spray per nostril once daily for a period of at least 1 week;
b) the composition is nasally administered as 2 sprays per nostril once daily for a period of at least 1 week;
c) the composition is nasally administered as 1 spray per nostril twice daily for a period of at least 1 week;
d) the composition is nasally administered as 2 sprays per nostril twice daily for a period of at least 1 week;
e) the composition is nasally administered as 1 spray per nostril once daily for a period of 2 weeks;
f) the composition is nasally administered as 2 sprays per nostril once daily for a period of 2 weeks;
g) the composition is nasally administered as 1 spray per nostril twice daily for a period of 2 weeks; or
h) the composition is nasally administered as 2 sprays per nostril twice daily for a period of 2 weeks.

In another embodiment, the present invention relates to a method of treating seasonal allergic rhinitis and/or nasal symptoms associated with seasonal allergic rhinitis in a human in need thereof comprising nasally administering to the human a synergistic combination comprising mometasone furoate and olopatadine hydrochloride, wherein the combination is in the form of a pharmaceutical composition comprising mometasone furoate in particulate form and olopatadine hydrochloride in solution in a weight ratio of about 1:13.3 to about 1:53.2 (based on the equivalent weight of olopatadine free base), and wherein the composition is administered as 1 or 2 sprays per nostril of the human, at least once daily for a period of at least 1 week wherein the method provides reduction of at least one adverse event. In one aspect of this embodiment, the composition is administered once daily or twice daily for a period of 2 weeks. In another aspect of this embodiment, each spray comprises about 25 mcg or about 50 mcg of mometasone furoate and about 665 mcg of olopatadine hydrochloride. In yet another aspect of this embodiment, (i) the total nasal symptoms score (TNSS) of the human is reduced by at least 50% from baseline after 2 weeks treatment, and/or (ii) total ocular symptom score (TOSS) of the human is reduced by at least 40% from baseline after 2 weeks treatment, and/or (iii) no significant treatment-related adverse effects are observed in the human after 2 weeks treatment. In one aspect of the said embodiment, the human exhibits a positive skin prick test to an allergen. Preferably, the treatment-related adverse effects include somnolence or epistaxis or a combination thereof.

In an aspect of the invention, the fixed-dose pharmaceutical composition may be administered for a period of about 1 week, 2 weeks, 4 weeks, 6 weeks or 8 weeks. Preferably, the fixed-dose pharmaceutical composition, is administered as 1 or 2 sprays per nostril of the subject (e.g., a human), once daily or twice daily for a period of 1 week or 2 weeks. In another aspect of the embodiment, each spray of the composition comprises olopatadine hydrochloride equivalent to about 600 mcg of olopatadine and about 25 mcg to about 50 mcg of mometasone furoate. Preferably, each spray of the composition comprises about 665 mcg of olopatadine hydrochloride (equivalent to about 600 mcg of olopatadine) and about 25 mcg or about 50 mcg of mometasone furoate. In yet another aspect, the composition does not have unpleasant odor and taste. In yet another aspect of the embodiment, the total nasal symptoms score (TNSS) of the human subject is reduced by at least 40% or at least 50% from baseline after 1 or 2 weeks treatment. In yet another aspect of the embodiment, the total ocular symptom score (TOSS) of the human is reduced by at least 30% or at least 40% from baseline after 1 or 2 weeks treatment. In yet another aspect of the embodiment, the said method provides reduction in treatment-related adverse effects. Preferably, the treatment-related adverse effects include somnolence or epistaxis or a combination thereof. In yet another aspect of the embodiment, the human subject is a patient exhibiting a positive skin prick test to an allergen.

In one aspect the present invention relates to the use of mometasone or its salt and olopatadine or its salt in a weight ratio of about 1:5 to about 1:60 or from about 1:12 to about 1:53 for the manufacture of a fixed-dose pharmaceutical composition of the invention for the treatment of allergic rhinitis in a subject (e.g., a human) in need thereof. In an aspect, the fixed-dose pharmaceutical composition is a suspension wherein mometasone or its salt is present in particle form (e.g., having a mean particle size of from about 1 to about 20 μm, or from about 1 to about 15 μm) and olopatadine or its salt is present in dissolved form. In yet another aspect, the composition does not have unpleasant odor and taste.

In a separate embodiment the present invention relates to a method of reducing symptoms associated with rhinitis in a subject (e.g. a human) in need thereof, the method comprising nasally administering to the subject an effective amount of a fixed dose pharmaceutical composition comprising mometasone or its salt and olopatadine or its salt in a weight ratio of about 1:5 to about 1:60 or from about 1:12 to about 1:53 for about 1 or 2 weeks.

In yet another embodiment, the present invention relates to a method of reducing symptoms associated with allergic rhinitis in a human in need thereof comprising nasally administering to the human an effective amount of a fixed-dose pharmaceutical composition comprising mometasone or its salt and olopatadine or its salt, wherein (i) the composition is nasally administered as 1 or 2 sprays per nostril of the human at least once daily, and (ii) each spray comprises mometasone or its salt and olopatadine or its salt in a weight ratio of about 1:5 to about 1:60 or from about 1:12 to about 1:53 for about 1 or 2 weeks. (based on the equivalent weight of olopatadine free base) and wherein the composition is administered as 1 or 2 sprays per nostril of the human, at least once daily for a period of at least 1 week, wherein the method provides reduction of at least one adverse event. In one aspect of this embodiment, each spray comprises about 25 mcg or about 50 mcg mometasone furoate and olopatadine hydrochloride equivalent to about 600 mcg olopatadine. In one aspect of this embodiment, the pharmaceutical composition is a suspension comprising mometasone or its salt in particulate form and olopatadine or its salt in solution. In one aspect of this embodiment, the composition is administered for a period of at least 1 week as—(i) 1 spray per nostril once daily or twice daily, or (ii) 2 sprays per nostril once daily or twice daily. In yet another aspect of this embodiment, the allergic rhinitis is selected from perennial allergic rhinitis, persistent allergic rhinitis, seasonal allergic rhinitis, and nasal and/or non-nasal symptoms associated therewith. In a preferred aspect, the allergic rhinitis is seasonal allergic rhinitis and/or nasal symptoms associated therewith. In yet another aspect of this embodiment, (i) the total nasal symptoms score (TNSS) of the human is reduced by at least 50% from baseline after 2 weeks treatment, and/or (ii) total ocular symptom score (TOSS) of the human is reduced by at least 40% from baseline after 2 weeks treatment, and/or (iii) no significant treatment-related adverse effects are observed in the human after 2 weeks treatment. In one aspect of the said embodiment, the human exhibits a positive skin prick test to an allergen. In one aspect of the said embodiment, the symptoms include rhinorrhea, nasal congestion, nasal itching, sneezing, itching/burning eyes, tearing/watering eyes, redness of eyes, itching of ears or palate, coughing, ocular pruritus, excess lacrimation, headache, fatigue and malaise. In yet another aspect of the embodiment, the treatment-related adverse effects include somnolence or epistaxis or a combination thereof.

The administration of the pharmaceutical composition may provide relief from one or more symptoms of allergic rhinitis (such as nasal symptoms or ocular symptoms) in a subject faster (e.g., an onset of action in less than 30 minutes, such as within about 15 minutes, such as within 10 minutes) than nasal administration of the mometasone or its salt or the olopatadine or its salt alone. In another embodiment, the administration may provide relief from one or more symptoms of allergic rhinitis (such as nasal symptoms) in a subject exposed to an environmental exposure chamber (EEC) (such as one with ragweed pollen at a concentration of 3500±500 particles/m$^3$ for 6 hours) faster (e.g., an onset of action in less than 15 minutes, such as within about 10 minutes) than nasal administration of the mometasone or its salt or the olopatadine or its salt alone.

Yet another embodiment is a method for providing faster onset of relief of symptoms associated with allergic rhinitis in a human subject in need thereof comprising nasally administering twice daily, two sprays per nostril of a fixed-dose pharmaceutical composition comprising mometasone or its salt (e.g., mometasone furoate) and olopatadine its salt (e.g., olopatadine hydrochloride). This method may provide faster onset of relief of one or more symptoms compared to administration of the mometasone or its salt alone or olopatadine or its salt alone. Each spray may comprise mometasone or its salt and olopatadine or its salt in a weight ratio of about 1:5 to about 1:60 (such as a weight ratio of about 1:12 to about 1:53, about 1:13.3 to about 1:50, or from about 1:18 to about 1:40) (based on the equivalent weight of olopatadine free base) (for example, each spray comprises about 12.5 mcg, about 25 mcg, about 37.5 mcg, about 50 mcg, or about 62.5 mcg of mometasone or its salt (such as about 50 mcg mometasone furoate) and olopatadine hydrochloride equivalent to about 300 mcg, about 450 mcg, about 600 mcg, about 750 mcg, or about 900 mcg of olopatadine (such as about 665 mcg olopatadine hydrochloride)). The administration may provide relief from one or more symptoms within 30 minutes, such as within 15 minutes or within 10 minutes. In another embodiment, the administration may provide relief from one or more symptoms of allergic rhinitis (such as nasal symptoms) in a subject exposed to an environmental exposure chamber (EEC) (such as one with ragweed pollen at a concentration of 3500±500 particles/m³ for 6 hours) in less than 15 minutes, such as within about 10 minutes.

Yet another embodiment is a method of treating a human subject suffering from allergic rhinitis comprising the step of administering to the subject a pharmaceutical composition for twice daily nasal administration of two sprays per nostril, wherein (i) the pharmaceutical composition provides an onset of action within 15 minutes for the treatment of allergic rhinitis and (ii) each spray of the pharmaceutical composition comprises about 25 mcg of mometasone furoate and about 665 mcg of olopatadine hydrochloride.

Yet another embodiment is a method of treating a human subject suffering from allergic rhinitis comprising the steps of:
(a) prescribing to a subject (e.g., a human subject) a fixed-dose pharmaceutical composition for twice daily nasal administration of two sprays per nostril, wherein the fixed-dose pharmaceutical composition comprises mometasone or its salt (such as mometasone furoate) and olopatadine or its salt (such as olopatadine hydrochloride), and each spray comprises mometasone or its salt and olopatadine or its salt in a weight ratio of about 1:5 to about 1:60 (such as a weight ratio of about 1:12 to about 1:53, about 1:13.3 to about 1:50, or from about 1:18 to about 1:40) (based on the equivalent weight of olopatadine free base) (for example, each spray comprises about 12.5 mcg, about 25 mcg, about 37.5 mcg, about 50 mcg, or about 62.5 mcg of mometasone or its salt (such as about 50 mcg mometasone furoate) and olopatadine hydrochloride equivalent to about 300 mcg, about 450 mcg, about 600 mcg, about 750 mcg, or about 900 mcg of olopatadine (such as about 665 mcg olopatadine hydrochloride)),
the prescribing being performed in response to (i) marketing of the pharmaceutical composition as (A) providing faster onset of action (such as an onset of action within less than 30 minutes, such as within 15 minutes, such as within 10 minutes) for relief of one or more symptoms (e.g., nasal symptoms) of allergic rhinitis than nasal administration of mometasone or its salt (such as 25 or 50 mcg mometasone furoate) or olopatadine or its salt (such as 665 mcg olopatadine hydrochloride) alone, (B) providing relief of one or more symptoms of allergic rhinitis within 15 minutes (or 30 minutes), and (ii) diagnosis of the human subject as suffering from allergic rhinitis, or (C) providing faster onset of action (such as within 15 minutes, such as within about 10 minutes) for relief of one or more symptoms (e.g., nasal symptoms) of allergic rhinitis in subjects exposed to an environmental exposure chamber (EEC) (such as one with ragweed pollen at a concentration of 3500±500 particles/m³ for 6 hours) than nasal administration of the mometasone or its salt or the olopatadine or its salt alone. (D) providing relief from one or more symptoms of allergic rhinitis (such as nasal symptoms) in subjects exposed to an environmental exposure chamber (EEC) (such as one with ragweed pollen at a concentration of 3500±500 particles/m³ for 6 hours) within 15 minutes, such as within about 10 minutes; and
(b) administering the prescribed pharmaceutical composition to the subject. In one preferred embodiment, each spray of the fixed-dose pharmaceutical composition provides 25 mcg mometasone furoate and 665 mcg olopatadine hydrochloride.

Yet another embodiment is a method of treating a human subject suffering from allergic rhinitis (such as seasonal allergic rhinitis or perennial allergic rhinitis) comprising the step of administering to the subject a prescribed fixed-dose pharmaceutical composition for twice daily nasal administration of two sprays per nostril, where the fixed-dose pharmaceutical composition comprises mometasone or its salt (such as mometasone furoate) and olopatadine or its salt (such as olopatadine hydrochloride), and each spray comprises mometasone or its salt and olopatadine or its salt in a weight ratio of about 1:5 to about 1:60 (such as a weight ratio of about 1:12 to about 1:53, about 1:13.3 to about 1:50, or from about 1:18 to about 1:40) (based on the equivalent weight of olopatadine free base) (for example, each spray comprises about 12.5 mcg, about 25 mcg, about 37.5 mcg, about 50 mcg, or about 62.5 mcg of mometasone or its salt (such as about 50 mcg mometasone furoate) and olopatadine hydrochloride equivalent to about 300 mcg, about 450 mcg, about 600 mcg, about 750 mcg, or about 900 mcg of olopatadine (such as about 665 mcg olopatadine hydrochloride)). The pharmaceutical composition is prescribed in response to (a) marketing of the pharmaceutical composition as (A) providing faster onset of action (such as an onset of action within less than 30 minutes, such as within 15 minutes, such as within 10 minutes) for relief of symptoms (e.g., nasal symptoms) of allergic rhinitis than nasal administration of mometasone or its salt (such as 50 mcg mometasone furoate) or olopatadine or its salt (such as 665 mcg olopatadine hydrochloride) alone or (B) providing relief of one or more symptoms of allergic rhinitis within 15 minutes (or 30 minutes), and (b) a diagnosis of the subject as suffering from allergic rhinitis. In one preferred embodiment, each spray of the fixed-dose pharmaceutical composition provides 25 mcg mometasone furoate and 665 mcg olopatadine hydrochloride.

Another embodiment relates to a method of reducing eosinophil count in the nasal lavage of a subject by nasally administering an effective amount of a fixed-dose pharmaceutical composition comprising mometasone or its salt and olopatadine or its salt in a weight ratio of about 1:5 to about 1:60 (based on the equivalent weight of olopatadine free base), wherein the method provides a greater reduction in eosinophil count than that provided by mometasone or its salt or olopatadine or its salt when administered as a monotherapy. The eosinophil count can be measured by any known technique, such as with a hemocytometer.

Yet another embodiment relates to a method of reducing total cell count in the nasal lavage by nasally administering an effective amount of a fixed-dose pharmaceutical composition comprising mometasone or its salt and olopatadine or its salt in a weight ratio of about 1:5 to about 1:60 (based on the equivalent weight of olopatadine free base) wherein the method provides a greater reduction in total cell count than that provided by mometasone or its salt or olopatadine or its salt when administered as a monotherapy.

In the context of the present invention, eosinophil count and total cell count can be measured using various instruments such as a hemocytometer. Sneezing response can be determined using instruments such as a whole body plethysmography (Buxco Research Systems, Wilmington, NC, USA).

In the context of the present invention, the fixed dose pharmaceutical composition comprising mometasone or its salt, olopatadine or its salt are preferably supplied in the form of nasal spray with one or more pharmaceutical acceptable excipients (e.g., chelating agents, preservatives, buffer, surfactants, isotonic agent, taste masking agents, suspending agents, humectants, antioxidants and diluents) in a container and a kit providing directions on its usage and administration. The pharmaceutical composition may, for example, have any one of the formulations described in International Patent Application No. PCT/IB2014/064251, filed Sep. 4, 2014, U.S. patent application Ser. No. 14/483,837, filed Sep. 11, 2014, U.S. patent application Ser. No. 14/662,128, filed Mar. 18, 2015, U.S. patent application Ser. No. 15/183,534, filed Jun. 15, 2016, and U.S. patent application Ser. No. 15/210,692, filed Jul. 14, 2016, each of which is hereby incorporated by reference in its entirety.

The pharmaceutical composition can be nasally administered with a nasal spray device (e.g., one capable of delivery a mist spray in the nostrils of a subject for local action on nasal mucosa).

Pharmaceutical Compositions

The pharmaceutical composition can contain an effective amount of mometasone or a salt thereof and olopatadine or a salt thereof. The effective amount of mometasone or its salt can range from about 0.01 mg to about 10 mg or preferably from about 0.02 mg to about 5 mg. The effective amount of olopatadine or its salt in the pharmaceutical composition can range from about 0.05 mg to about 20 mg, or preferably from about 0.1 mg to about 15 mg.

For daily administration by the nasal route, the effective amount of mometasone or its salt in the pharmaceutical composition can range from about 10 mcg to about 500 mcg, or preferably from about 20 mcg to about 400 mcg, and that for olopatadine or its salt can ranges from about 50 mcg to about 7000 mcg, or preferably from about 100 mcg to about 5400 mcg.

The term "average particle size" (or synonymously, "mean particle size") as used herein refers to the distribution of particles, wherein about 50 volume percent of all the particles measured have a size less than the defined average particle size value and about 50 volume percent of all particles measured have a particle size greater than the defined average particle size value. This can be identified by the term "$D_{50}$" or "$d_{(0.5)}$". The average particle size can be measured using various techniques such as microscopy, laser diffraction, photon correlation spectroscopy (PCS) and Coulter's principle.

The term "$C_{max}$" is the maximum concentration of a drug (e.g., mometasone or olopatadine) in the blood plasma.

The term "$T_{max}$" is the time at which the peak (maximum) blood plasma drug concentration is achieved.

The term "$AUC_{0-\infty}$" is the mean area under the plasma concentration-time curve extrapolated to infinity. It is calculated as the arithmetic mean of the area under the plasma concentration-time curve from time 0 extrapolated to infinity.

The term $AUC_{tau}$" is the area under the curve for a plasma, serum or blood concentration versus time curve of a drug reached by a given dose over one dosing interval at steady state. The area under the curve is measured for a time tau at steady state, where tau is the length of the dosing interval.

The term "hydrocolloid" refers to a colloid system wherein hydrophilic colloid particles (e.g., hydrophilic polymers) are dispersed in water. The hydrocolloid system can exist in gel state or sol (liquid) state. In suspension compositions, the hydrocolloids function as thickening, stabilizing and suspending agents. Non-limiting examples of hydrocolloids include xanthan gum, gum arabic, guar gum, locust bean gum, alginate, starch, agar-agar, carrageenan, gelatin, a mixture of microcrystalline cellulose (MCC) and sodium carboxymethyl cellulose (sodium CMC) (e.g., Avicel RC591® (available from FMC Biopolymer, Philadelphia, PA), a mixture of MCC and sodium CMC with a sodium CMC content of 8.3-13.8%), and cellulose derivatives (e.g., carboxymethyl cellulose sodium). Preferably, the hydrocolloid includes xanthan gum or carboxymethylcellulose sodium.

Some embodiments of the present invention provide compositions comprising carboxymethylcellulose sodium. In some embodiments, the compositions comprise from about 0.08 to about 2% carboxymethylcellulose sodium. In some embodiments, the compositions comprise from about 0.1% w/w to about 1.5% w/w carboxymethylcellulose sodium. In some embodiments, the compositions comprise from about 0.12% w/w to about 1% w/w carboxymethylcellulose sodium. In some embodiments, the compositions comprise from about 0.15% w/w to about 0.75% w/w carboxymethylcellulose sodium. In some embodiments, the compositions comprise about 0.083% w/w carboxymethylcellulose sodium. In some embodiments, the compositions comprise 0.0830% w/w carboxymethylcellulose sodium. In some embodiments, the compositions comprise about 0.1% w/w carboxymethylcellulose sodium. In some embodiments, the compositions comprise 0.0996% w/w carboxymethylcellulose sodium. In some embodiments, the compositions comprise about 0.7% w/w carboxymethylcellulose sodium. In some embodiments, the compositions comprise 0.6656% w/w carboxymethylcellulose sodium.

The term "container" refers to single unit-dose container or multi-dose container. Suitable single unit-dose containers or multi-dose containers include, but are not limited to, glass, aluminum, polypropylene or high density polyethylene, for example, high density polyethylene containers produced using a blow-fill-seal manufacturing technique. In one embodiment, the container is a sprayer which delivers the pharmaceutical composition in the form of a fine mist. A sprayer generally includes a container containing a pharmaceutical composition, a pump sealed (e.g., hermetically engaged) with the container, an actuator removably receiving a top portion of the pump, and a cap removably engaged with the container and the actuator.

One embodiment is a stable fixed dose, aqueous pharmaceutical composition (e.g., contained in a container) for nasal administration to a human, where the composition comprises about 0.001% w/w to about 0.075% w/w mometasone or its salt and about 0.5% w/w to about 0.8% w/w olopatadine or its salt.

The pharmaceutical composition may be in the form of a solution or a suspension, but preferably the composition is in the form of a suspension (more preferably, a single phase suspension), wherein mometasone or its salt is present in particle form and olopatadine or its salt is present in dissolved form. The mometasone or its salt and olopatadine or its salt may be present at a weight ratio of about 1:3 to about 1:106, or from about 1:5 to about 1:53 or preferably from about 1:5 to about 1:36. In one embodiment, the weight ratio of mometasone or its salt and olopatadine or its salt in the composition is from about 1:10 to about 1:53 or from about 1:12 to about 1:30.

The composition preferably also includes a hydrocolloid. In one embodiment, the composition is a suspension and includes a hydrocolloid in a sufficient amount to prevent phase separation (i.e., separation of the particles and solution) after 3 or 6 months of storage at 25±2° C. and 60%±5% relative humidity (RH) or at 40±2° C. and 75%±5% RH. In one embodiment, the aqueous pharmaceutical composition is a single phase suspension which remains a single phase suspension even after 3 or 6 months of storage at 25±2° C. and 60%±5% RH or at 40±2° C. and 75%±5% RH.

Another embodiment is an aqueous pharmaceutical composition comprising (a) mometasone or its salt, (b) olopatadine or its salt, and (c) a fibrillar network comprising a cellulosic material. The fibrillar network may have interfibrillar spaces. In one embodiment, the interfibrillar spaces contain one or more mometasone particles. In some embodiments, the mometasone or its salt is present in particulate form having an average particle size of less than about 15 µm. In further embodiments, the mometasone particles are equidistantly, or substantially equidistantly, spaced within the fibrillar network. The average distance between adjacent mometasone particles may be spaced sufficiently to provide consistent delivery of a fixed amount (or an effective amount) of both the mometasone (or its salt) and olopatadine (or its salt), for example, for 30, 56, 60, 120, or 240 doses (e.g., by nasal spray administration). In some embodiments, the fibrillar network is at least partially responsible for the ability of the compositions of the present invention to provide consistent dosing of a fixed amount, or an effective amount, of the active ingredients to the target site. The olopatadine or its salt in such compositions may be in dissolved form.

The term 'stable' as used in connection with aqueous suspensions refers to a composition when shaken and then stored for at least 24 hours at ambient condition does not show phase separation on visual inspection. Preferably, such stable composition does not show phase separation for a period of at least 3 days, or at least 5 days, or at least 7 days. In one aspect, the 'stable' composition of the present invention shows, upon shaking (e.g., for 1 minute) and visual inspection, no lump formation and a total impurity content of no more than 1.0% after storage at ambient conditions (at about 25° C. and a relative humidity of about 60%) for a period of at least 6 months.

In the context of the present invention, the drug content and impurities can be determined by various analytical techniques such as HPLC, LC-MS, TLC and the like.

It was observed that when various pharmaceutical compositions for nasal administration comprising mometasone or its salt and olopatadine or its salt were prepared, the compositions generally showed physical separation in the suspension composition. This physical instability further leads to lack of dose uniformity. Surprisingly, it was found that addition of a hydrocolloid at certain concentrations (e.g. at a concentration of at least about 0.1% w/w) in the suspension composition yielded a physically stable composition (with no separation) suitable for nasal administration.

Another embodiment is a stable fixed dose, aqueous pharmaceutical suspension composition (e.g., contained in a container) for nasal administration to a human, where the composition comprises about 0.025% w/w to about 0.05% w/w mometasone or its salt, about 0.6% w/w to about 0.7% w/w olopatadine or its salt and a hydrocolloid.

Yet another embodiment is a stable fixed dose, aqueous pharmaceutical suspension composition (e.g., contained in a container) for nasal administration to a human, where the composition comprises about 0.025% w/w to about 0.05% w/w mometasone or its salt, about 0.6% w/w to about 0.7% w/w olopatadine or its salt and a hydrocolloid which includes carboxymethylcellulose sodium and xanthan gum. The hydrocolloid may be present at a concentration of at least about 0.1% w/w of the composition.

Yet another embodiment is a stable fixed dose, aqueous pharmaceutical suspension composition (e.g., contained in a container) for nasal administration to a human, comprising about 0.025% w/w to about 0.05% w/w mometasone furoate, about 0.6% w/w to about 0.7% w/w olopatadine hydrochloride and a hydrocolloid which comprises xanthan gum. The xanthan gum may be present at a concentration of at least about 0.1% w/w, or preferably between about 0.3% w/w to about 3% w/w of the composition.

Yet another embodiment is a stable fixed dose, aqueous pharmaceutical suspension composition (e.g., contained in a container) for nasal administration to a human, comprising about 0.025% w/w to about 0.05% w/w mometasone furoate, about 0.6% w/w to about 0.7% w/w olopatadine hydrochloride and a hydrocolloid which comprises sodium carboxymethyl cellulose. The sodium carboxymethyl cellulose may be present at a concentration of at least about 0.1% w/w, or preferably between about 0.1% w/w to about 3% w/w of the composition.

Yet another embodiment is a stable fixed dose aqueous pharmaceutical composition in the form of suspension (e.g., contained in a container) for nasal administration to a human, comprising mometasone or its pharmaceutically acceptable salt, olopatadine or its pharmaceutically acceptable salt, a hydrocolloid (e.g., at a concentration of at least about 0.1% w/w of the composition) and a pharmaceutical acceptable excipient.

It will also be appreciated to the skilled artisan that in order to improve the physical properties, appearances, or smells of the composition of the present invention, one or more further pharmaceutically acceptable excipients may be added as desired. Suitable pharmaceutical acceptable excipients include, but are not limited to, chelating agents, preservatives, buffers, surfactants, isotonicity agents, taste masking agents, antioxidants, humectants, pH adjusting agents, and any combination of any of the foregoing.

Suitable surfactants which can be used for preparing aqueous nasal spray composition may include one or more of anionic, cationic, non-ionic or zwitterionic surfactants.

Examples of suitable surfactants which can be employed in the aqueous nasal spray suspension may be selected from, but not limited to, polyethoxylated sorbitan derivatives such as polysorbates, their ether ethoxylates, produced by reaction of sorbitan esters with ethylene oxide, polyoxyethylene alkyl phenol, polyoxyethylene cetyl ether, polyoxyethylene alkyl-aryl ether, polyoxyethylene monolaurate, polyoxyethylene vegetable oil, polyoxyethylene sorbitan monolaurate, polyoxyethylene esters or mixed fatty and resin acids, polyoxyethylene sorbitol lanolin derivative, polyoxyethylene tridecylether, polyoxyethylene sorbitan esters of mixed fatty and resin acids, polyoxyethylene sorbitan monostearate, polyoxyethylene sorbitan monooleate, polyoxyethylene monostearate, polyoxyethylene stearyl ether, polyoxyethylene oleyl ether, polyoxyethylene tridecyl ether, polyoxyethylene fatty alcohol, polyoxyethylene alkyl amine, polyoxyethylene glycol monopalmitate, polyoxyethylene sorbitan monopalmitate, polyoxyethylene cetyl ether, polyoxyethylene oxypropylene stearate, polyoxyethylene lauryl ether, polyoxyethylene lanolin derivative, sodium oleate, quaternary ammonium derivative, potassium oleate, N-cetyl N-ethyl morpholinium ethosulfate, sodium lauryl sulfate or mixtures thereof. Preferred surfactants are polyethoxylated sorbitan derivatives (such as polysorbate 80). The amount of surfactant may range from about 0.001% to about 1% w/w relative to the total weight of the composition.

In order to improve the ability of the aqueous nasal spray suspension to be tolerated on administration to the nasal mucous membrane, it is advantageous to formulate it as isotonic. The osmolality can be set by variation of the amounts of the substances present in the aqueous nasal spray suspension besides mometasone, olopatadine and any further substances present, and/or by addition of an isotonicity agent, preferably a physiologically tolerated salt, such as, for example, sodium chloride or potassium chloride, or a physiologically tolerated polyol, such as, for example, a sugar alcohol, in particular sorbitol or glycerol, in the concentration necessary for rendering isotonic.

Examples of suitable preservatives which can be employed in the aqueous nasal spray suspension include, but are not limited to, benzyl alcohol, quaternary ammonium halides, phenylcarbinol, thimerosal, and disodium edetate. Quaternary ammonium halide preservatives are preferred. Suitable quaternary ammonium halide preservatives include polyquaternium-1 and benzalkonium halides. Preferred benzalkonium halides include benzalkonium chloride and benzalkonium bromide. The amount of the preservative present in the aqueous nasal spray suspension may range from about 0.005 to about 0.2% w/w relative to the total weight of the composition. Preferably, the preservative is present at a concentration of about 0.02% w/w relative to the total weight of the composition.

Examples of suitable chelating agents which can be employed in the aqueous nasal spray suspension include, but are not limited to, edetate disodium (EDTA), edetate trisodium, edetate tetrasodium, and diethyleneamine pentaacetate, preferably EDTA. The amount of the chelating agent present in the aqueous nasal spray suspension of the present invention may range from about 0.0002 to about 0.5% w/w relative to the total weight of the composition.

Examples of suitable buffers which can be employed in the aqueous nasal spray suspension include, but are not limited to, citric acid, acetic acid, fumaric acid, hydrochloric acid, malic acid, nitric acid, phosphoric acid, propionic acid, sulfuric acid, tartaric acid, phosphate salts (e.g., dibasic sodium phosphate, such as dibasic sodium phosphate heptahydrate), or combinations thereof. The suspension of the present invention may comprise an amount of a buffer sufficient to maintain the pH of the composition to from about 3 to about 6. Preferably, the amount of buffer ranges from about 0.005% to about 1% w/w relative to the total weight of the composition.

Examples of suitable sweetener/taste masking agents which can be employed in the aqueous nasal spray suspension include, but are not limited to, sucralose, thaumatin (e.g., Talin®), sucrose, saccharin (including salt forms such as sodium and calcium salts), fructose, glucose, dextrose, corn syrup, aspartame, acesulfame-K, xylitol, sorbitol, erythritol, ammonium glycyrrhizinate, neotame, mannitol, *eucalyptus* oil, camphor, and natural or artificial flavors or flavoring agents (for example menthol, mints, vanilla, orange, etc.), or combinations of two or more of such agents. A particularly preferred taste masking agent is sucralose. The amount of the sweetener/taste masking agent present in the aqueous nasal spray suspension may range from about 0.01% to about 1% w/w relative to the total weight of the composition.

Examples of suitable antioxidants which can be employed in the aqueous nasal spray suspension include, but are not limited to, ascorbic acid, alpha-tocopherol (vitamin-E), butylated hydroxyanisole, butylated hydroxytoluene, glutathione, and any combination of any of the foregoing. The amount of the antioxidants present in the aqueous nasal spray composition may range from about 0.0002% to about 0.5% w/w relative to the total weight of the composition.

Examples of suitable humectants which can be employed in the aqueous nasal spray suspension include, but are not limited to, glycerin, sorbitol, polyethylene glycol, propylene glycol or mixtures thereof, which are mixed with a suitable humectant vehicle such as water. The amount of humectant present in the aqueous nasal spray suspension may range from about 0.0002% to about 0.5% w/w relative to the total weight of the composition.

Suitable pH adjusting agents include, but are not limited to, sodium hydroxide and hydrochloric acid.

In the context of present invention, the pharmaceutical stable fixed dose suspension composition for nasal administration may have a pH of between about 3.3 and about 4.1, or between about 3.5 and about 3.9. The inventors discovered that the olopatadine hydrochloride crystallizes out of the fixed dose combination aqueous suspension at a pH of 5 to 5.5. The olopatadine hydrochloride, however, remains dissolved in the aqueous suspension at a pH of about 3.3 to about 4.1.

The aqueous pharmaceutical composition preferably is substantially free of crystals of olopatadine hydrochloride. In one embodiment, the aqueous pharmaceutical composition contains less than 2%, less than 1%, less than 0.5%, less than 0.2%, or less than 0.1% of crystalline olopatadine hydrochloride, based on the 100% total weight of olopatadine hydrochloride in the composition. In another embodiment, the aqueous pharmaceutical composition is substantially free of crystals of olopatadine hydrochloride after 3 or 6 months of storage at 25±2° C. and 60%±5% RH or at 40±2° C. and 75%±5% RH. In yet another embodiment, the aqueous pharmaceutical composition contains less than 2%, less than 1%, less than 0.5%, less than 0.2%, or less than 0.1% of crystalline olopatadine hydrochloride, based on the 100% total weight of olopatadine hydrochloride in the composition, after 3 or 6 months of storage at 25±2° C. and 60%±5% RH or at 40±2° C. and 75%±5% RH.

The osmolality of the composition may range between about 200 mOsm/kg and about 400 mOsm/kg, or about 250 mOsm/kg and about 350 mOsm/kg. The viscosity of the composition may be about 10 cps to about 200 cps or preferably from about 20 cps to about 150 cps.

In yet another aspect, the pharmaceutical composition in the form of suspension and contains mometasone furoate in particles having mean particle size in the range of from about 1 μm to about 20 μm, or preferably from about 1 μm to about 15 μm. In an aspect, the suspension pharmaceutical composition of the present invention has mean particle size of less than 15 μm when determined by microscopy technique.

In yet another aspect, the pharmaceutical composition, upon nasal administration (e.g., as a nasal spray) of a dose equivalent to 200 mcg of mometasone or its salt to a human, results in (a) an area under the curve $(AUC)_{0-\infty}$ for mometasone or its salt of about 50 pg·hr/mL to about 140 pg·hr/mL, preferably from about 68 pg·hr/mL to about 124 pg·hr/mL, (b) a $C_{max}$ for mometasone or its salt of about 6.5 pg/mL to about 16 pg/ml, preferably from about 8.6 pg/mL to about 12.9 pg/ml, (c) a $T_{max}$ for mometasone or its salt of about 15 minutes to about 120 minutes, or (d) any combination of any of the foregoing.

In yet another aspect, the pharmaceutical composition, upon nasal administration (e.g., as a nasal spray) of a dose equivalent to 2400 mcg of olopatadine or its salt to a human, results in (a) an $AUC_{0-\infty}$ for olopatadine or its salt of about 42.5 ng·hr/mL to about 116.5 ng·hr/mL, preferably from about 56.7 ng·hr/mL to about 99.8 ng·hr/mL, (b) a $C_{max}$ for olopatadine or its salt of about 10.3 ng/mL to about 24.1 ng/ml, preferably from about 13.8 ng/mL to about 20.7 ng/ml, (c) a $T_{max}$ of about 15 minutes to about 120 minutes, or (d) any combination of any of the foregoing.

In yet another aspect, the pharmaceutical composition, upon nasal administration (e.g., as a nasal spray) of a dose equivalent to 100 mcg of mometasone or its salt (e.g., mometasone furoate) to a human for the first time, results in (a) an area under the curve $(AUC)_{tau}$ for mometasone or its salt of about 12 pg·hr/mL to about 73 pg·hr/mL, preferably from about 20 pg·hr/mL to about 36 pg·hr/mL, (b) a $C_{max}$ for mometasone or its salt of about 3 pg/mL to about 13 pg/ml, preferably from about 5 pg/mL to about 9 pg/ml, (c) a $T_{max}$ for mometasone or its salt of about 15 minutes to about 120 minutes, or (d) any combination of any of the foregoing. In yet another aspect, the pharmaceutical composition, upon nasal administration (e.g., as a nasal spray) of a dose equivalent to 100 mcg of mometasone or its salt (e.g., mometasone furoate) to a human at steady state (e.g., after 8 days of twice daily administration of 100 mcg of mometasone or its salt), results in (a) an area under the curve $(AUC)_{tau}$ for mometasone or its salt of about 26 pg·hr/mL to about 124 pg·hr/mL, preferably from about 40 pg·hr/mL to about 80 pg·hr/mL, (b) a $C_{max}$ for mometasone or its salt of about 4 pg/mL to about 16 pg/ml, preferably from about 8 pg/mL to about 12 pg/ml, (c) a $T_{max}$ for mometasone or its salt of about 15 minutes to about 120 minutes, or (d) any combination of any of the foregoing.

In yet another aspect, the pharmaceutical composition, when delivered as a nasal spray has a spray pattern having a longest axis of about 15-75 mm, a shortest axis of about 10-65 mm, and an ellipticity of about 1-2.

In the context of present invention, the viscosity can be determined by various known instruments such as a Dynamic stress rheometer or Brookfield viscometer. In a preferred embodiment, the viscosity is determined by a Brookfield viscometer by measuring torque transmission through a sample using a rotating spindle.

In another embodiment, the present invention relates to a stable fixed dose, aqueous pharmaceutical composition (e.g., contained in a container) for nasal administration to a human, where the composition comprises about 0.001% w/w to about 0.075% w/w mometasone furoate monohydrate and about 0.5% w/w to about 0.8% w/w olopatadine hydrochloride.

Another embodiment is a stable fixed dose pharmaceutical composition in the form of suspension (e.g., contained in a container) for nasal administration to a human, comprising mometasone furoate monohydrate, olopatadine hydrochloride and a hydrocolloid which comprises xanthan gum at a concentration of about 0.3% w/w of the composition, wherein the composition has a pH between about 3.5 and about 3.9.

Yet another embodiment is a stable fixed dose pharmaceutical composition in the form of suspension (e.g., contained in a container) for nasal administration to a human, comprising mometasone furoate monohydrate, olopatadine hydrochloride and a hydrocolloid which comprises sodium carboxymethyl cellulose at a concentration of about 0.5% w/w of the composition, wherein the composition has a pH between about 3.5 and about 3.9.

Yet another embodiment is a stable fixed dose pharmaceutical aqueous suspension composition (e.g., contained in a container) for nasal administration to a human, where the composition comprises (1) about 0.025% w/w mometasone furoate monohydrate, (2) about 0.665% w/w olopatadine hydrochloride, (3) a hydrocolloid selected from about 0.3% w/w of xanthan gum and about 0.5% w/w carboxymethyl cellulose sodium, (4) about 0.02% w/w benzalkonium chloride, (5) about 0.4% w/w sodium chloride, (6) about 0.01% w/w di-sodium edetate, (7) about 0.94% w/w sodium phosphate heptahydrate, and (8) about 0.01% w/w polysorbate 80.

Yet another embodiment is a stable fixed dose pharmaceutical aqueous suspension composition (e.g., contained in a container) for nasal administration to a human, where the composition comprises (1) about 0.050% w/w mometasone furoate monohydrate, (2) about 0.665% w/w olopatadine hydrochloride, (3) a hydrocolloid selected from about 0.3% w/w of xanthan gum and about 0.5% w/w carboxymethyl cellulose sodium, (4) about 0.02% w/w benzalkonium chloride, (5) about 0.4% w/w sodium chloride, (6) about 0.01% w/w di-sodium edetate, (7) about 0.94% w/w sodium phosphate heptahydrate, and (8) about 0.01% w/w polysorbate 80.

Yet another embodiment is a stable fixed dose pharmaceutical aqueous suspension composition (e.g., contained in a container) for nasal administration to a human, where the composition comprises (1) about 0.025% w/w mometasone furoate monohydrate, (2) about 0.665% w/w olopatadine hydrochloride, (3) a hydrocolloid selected from about 0.3% w/w of xanthan gum and about 0.5% w/w carboxymethyl cellulose sodium, (4) about 1% w/w to about 1.2% w/w mixture of microcrystalline cellulose and carboxymethyl cellulose sodium, (5) about 0.02% w/w benzalkonium chloride, (6) about 0.4% w/w sodium chloride, (7) about 0.01% w/w di-sodium edetate, (8) about 0.94% w/w sodium phosphate heptahydrate, and (9) about 0.01% w/w polysorbate 80.

Yet another embodiment is a stable fixed dose pharmaceutical aqueous suspension composition (e.g., contained in a container) for nasal administration to a human, where the composition comprises (1) about 0.050% w/w mometasone furoate monohydrate, (2) about 0.665% w/w olopatadine hydrochloride, (3) a hydrocolloid selected from about 0.3% w/w of xanthan gum and about 0.5% w/w carboxymethyl cellulose sodium, (4) about 1% w/w to about 1.2% w/w mixture of microcrystalline cellulose and carboxymethyl cellulose sodium, (5) about 0.02% w/w benzalkonium chloride, (6) about 0.4% w/w sodium chloride, (7) about 0.01% w/w di-sodium edetate, (8) about 0.94% w/w sodium phosphate heptahydrate, and (9) about 0.01% w/w polysorbate 80.

Yet another embodiment is a stable suspension suitable for nasal administration to a human, comprising (a) an aqueous solvent, (b) particles of mometasone furoate suspended in the solvent, the particles having a mean particle size of from about 1 to about 20 μm, (c) olopatadine hydrochloride dissolved in the solvent, and (d) a hydrocolloid, the suspension having a viscosity in the range of about 20 cps to about 150 cps. In one preferred embodiment, the suspension has a pH of about 3.5-3.9, and osmolality in the range of about 250 mOsm/kg to about 350 mOsm/kg. In one embodiment, the suspension further comprises a chelating agent, a preservative, a buffer, a surfactant, an isotonicity agent, and optionally a pH adjusting agent.

Preferably, the suspensions of the present invention have only one phase (i.e., they are preferably a single phase suspension).

In a further embodiment, the present invention relates to kit comprising a stable fixed dose, aqueous pharmaceutical composition of the present invention contained in a container for nasal administration and a package insert containing instructions about the use of said pharmaceutical composition. In one preferred embodiment, the container is part of a sprayer which has an actuator. When the actuator is actuated, the composition is delivered in the form of a spray.

In a further embodiment, the pharmaceutical composition is contained in a sprayer, and has, on deliver a spray of the composition to a human nose, a spray pattern having a longest axis of 15-75 mm, a shortest axis of 10-65 mm, and an ellipticity of 1-2.

In the context of present invention, the pharmaceutical composition when delivered as a nasal spray using a sprayer yields a specific spray pattern and spray droplet size. The spray pattern can be determined by various known techniques such as with an ADSA with NSPUA set up (Innova System) and the spray droplet size distribution can be determined by various known techniques such as with a Malvern Spraytec with NSPUA set up (Innova System).

The following describes a typical procedure for characterizing droplet size distribution of the spray—The sprayer is loaded with a composition as described above and primed by an actuating pump via an actuator until a fine mist appears out of the nozzle of the sprayer. A commercially available laser diffraction instrument is arranged so that the nozzle is about 3 cm or 6 cm below the laser beam of the laser diffraction instrument. The pump is actuated with a conventional mechanical actuator using a constant force. The resulting spray of the composition crosses the laser beam. Data are collected for $D_{10}$, $D_{50}$, $D_{90}$, SPAN, and % Volume <10 μm. The average values for each of these parameters for three sprays are calculated.

One embodiment is a stable fixed dose, aqueous pharmaceutical composition comprising mometasone furoate monohydrate, olopatadine hydrochloride and optionally a hydrocolloid contained in a sprayer, wherein each spray of the aqueous pharmaceutical composition provides (i) mometasone furoate monohydrate equivalent to about 50 mcg of mometasone furoate and (ii) olopatadine hydrochloride equivalent to about 600 mcg olopatadine.

Yet another embodiment is a stable fixed dose, aqueous pharmaceutical composition comprising mometasone furoate monohydrate, olopatadine hydrochloride and optionally a hydrocolloid contained in a sprayer, wherein each spray of the aqueous pharmaceutical composition provides (i) mometasone furoate monohydrate equivalent to about 25 mcg of mometasone furoate and (ii) olopatadine hydrochloride equivalent to about 600 mcg olopatadine.

The stable aqueous nasal spray suspension of mometasone and olopatadine may comprise one or more additional pharmaceutical active agent/s selected from the therapeutic category of, but not limited to, non-steroidal anti-inflammatory agents, decongestants, and any combination of any of the foregoing.

The aqueous nasal spray suspension can be administered as a drop or any other form suitable for topical administration. The composition may also be administered using a nasal tampon or a nasal sponge.

In a preferred embodiment, the aqueous suspension is provided in the form of nasal spray wherein the suspension is administered in a single unit-dose container or multi-dose container. Suitable single unit-dose containers or multi-dose containers include, but are not limited to, glass, aluminum, polypropylene or high density polyethylene, for example, high density polyethylene containers produced using a blow-fill-seal manufacturing technique.

In one embodiment, the pharmaceutical composition is contained within a spray bottle (such as a sprayer). The spray bottle may include a container for storing the pharmaceutical composition and a pump for spraying the pharmaceutical composition intranasally. In one embodiment, the container is capable of storing 30, 56, 60, or 120, or 240 doses. For example, a container storing 240 doses can provide a 1 month supply of the pharmaceutical composition (2 sprays per nostril twice daily (8 sprays per day) for 30 days). A container storing 56 doses can provide a 1 week supply of the pharmaceutical composition (2 sprays per nostril twice daily (8 sprays per day) for 7 days). In one embodiment, the container may be suitable for containing 9-10 mL (e.g., 9 mL or 56 doses), 18-19 mL of the pharmaceutical composition (e.g., 18 mL or 120 doses), or 29-30 mL (e.g., 29 mL or 240 doses) of the pharmaceutical composition.

In certain additional embodiments, the invention provides a multi dosage composition of matter, comprising: (a) a multi-unit dosage of a pharmaceutical composition of the present invention; and (b) a container comprising: (i) a squeezable chamber holding the multi dosage of the composition and having an opening wherein the dosage exits the opening when the squeezable chamber is squeezed; and (ii) a closure mechanism removably attached to the opening of the squeezable chamber. In certain embodiments, the multi dosage container is made of a moldable polymer.

In such embodiments, suitable polymers include, but are not limited to, polyethylene, polypropylene (PP), polystyrene (PS), nylon (Ny), polyvinyl chloride (PVC), polyethylene terephthalate (PET), polycarbonate (PC), polyoxymethylene (POM), polysulfon (PSF), polyethersulfon (PES), polyacrylate (PAR), and polyamid (PA). In certain embodiments, polymers include polyethylene, particularly medium-density polyethylene (MDPE) (or branched polyethylene) or high density polyethylene (HDPE) (or linear, polyethylene). In one embodiment, the multi dose container is made of high density polyethylene (HDPE).

Other means for delivering the nasal spray, such as inhalation via a metered dose inhaler (MDI), may also be used. Several types of MDIs are regularly used for administration by inhalation. These types of devices can include breath-actuated MDIs, spacer/holding chambers in combination with MDIs, and nebulizers. The term "MDI" as used herein refers to an inhalation delivery system comprising, for example, a canister containing a mixture of an active agent and a propellant optionally with one or more excipients, a metered dose valve, an actuator, and a mouthpiece. The canister is usually filled with a suspension of an active agent, such as the nasal spray composition, and a propellant, such as one or more hydrofluoroalkanes [e.g. 1,1,1,2-tetrafluoroethane (HFA-134a) and 1, 1,1,2,3,3,3-heptafluoropropane (HFA-227)], chlorofluorocarbons, and alcohols such as ethanol, isopropanol, butanol, propanol or mixtures thereof. When the actuator is depressed a metered dose of the suspension is aerosolized for inhalation. Particles comprising the active agent are propelled towards the mouthpiece where they may then be inhaled by a subject.

A further embodiment is a stable fixed dose, aqueous pharmaceutical composition (e.g., contained in a container) for nasal administration comprising about 0.025% w/w to about 0.05% w/w mometasone or its salt and about 0.5 w/w to about 0.8% w/w olopatadine or its salt for the treatment of rhinitis in a human in need thereof.

The following examples are provided to enable one skilled in the art to practice the invention and these are merely illustrative of the invention and should not be read as limiting the scope of the invention.

EXAMPLES

Example 1

Effect of Mometasone and Olopatadine and their Combination on Ovalbumin Induced Rhinitis Model in Male Guinea Pigs Male Dunkin Hartley guinea pigs were actively sensitized with a subcutaneous injection of 1.5 mg of ovalbumin and 20 mg of aluminum hydroxide gel on days 0 and 7. Guinea pigs were sensitized intranasally with 2% ovalbumin from days 14-17. On day 28, the animals were challenged with 6% ovalbumin intranasally.

Animal Grouping

Actively sensitized animals were randomly assigned to one of the following 5 groups during the experiment (see Table 1).

A: Saline Control (vehicle treated/saline challenged),
B: Ovalbumin Control (vehicle treated/ovalbumin challenged),
C: Olopatadine hydrochloride 50 µg (based on the equivalent weight of olopatadine free base) (olopatadine hydrochloride 50 µg treated/ovalbumin challenged),
D: Mometasone furoate 10 µg (mometasone furoate 10 µg treated/ovalbumin challenged) and
E: Combination (mometasone furoate 10 µg+olopatadine hydrochloride 50 µg (based on the equivalent weight of olopatadine free base) treated/ovalbumin challenged).

Compound Administration

Mometasone furoate 10 µg was given intranasally 24 hours and 1 hour prior to the final ovalbumin challenge. Olopatadine hydrochloride was given intranasally 1 hour before the final ovalbumin challenge. The dosing volume was 40 µl/animal. The saline control group and ovalbumin control group received vehicle (40 µl, 0.1% Tween 80 in distilled water).

TABLE 1

Animal Groups

| Group | Group Code | Treatment | Ovalbumin Challenge | Animals/group |
|---|---|---|---|---|
| A | Saline Control | Vehicle | − | 6 |
| B | Ovalbumin Control | Vehicle | + | 7 |
| C | Olopatadine 50 µg | Olopatadine Hydrochloride 50 µg | + | 7 |
| D | Mometasone 10 µg | Mometasone Furoate 10 µg | + | 6 |
| E | Combination | Olopatadine Hydrochloride 50 µg + Mometasone Furoate 10 µg | + | 7 |

In Vivo Evaluation

Measurement of Sneezing Response

Sneezing response was determined by using whole body plethysmography (Buxco Research Systems, USA) for 50 minutes after final saline or ovalbumin challenge.

Nasal Lavage

Nasal lavage was performed at 4 hours after challenge of animals with saline or ovalbumin on day 28. Animals were anesthetized with an overdose of urethane, the trachea was exposed and nasal lavage was performed using 2 mL pre-warmed normal saline. The collected nasal lavage was taken for total cell count using a hemocytometer. The nasal lavage was centrifuged, and the cell pellet resuspended in 15 µL guinea pig serum and used for preparation of smears. Slides were stained with Leishman's stain and a differential cell count of 100 cells based on standard morphology was performed manually.

Calculations

The total number of eosinophils in each nasal lavage sample was calculated using the formula:

$$\text{Total No. of eosinophils (in nasal lavage)} = \frac{\text{Total cell count} \times 10^5/\text{mL} \times \text{Percent eosinophils}}{100}$$

Percent inhibition of eosinophils was calculated using the following formula:

$$\% \text{ Inhibition of eosinophils} = \frac{\text{Avg. eosinophils}_{(Ovalbumin\ control)} - \text{eosinophils}_{(compound)}}{\text{Avg. eosinophils}_{(Ovalbumin\ control)} - \text{Avg. eosinophils}_{(Saline\ Control)}} \times 100$$

Data Analysis

Data was statistically analyzed using one way ANOVA followed by Dunnett's multiple comparison tests.

Results

Figure 2:
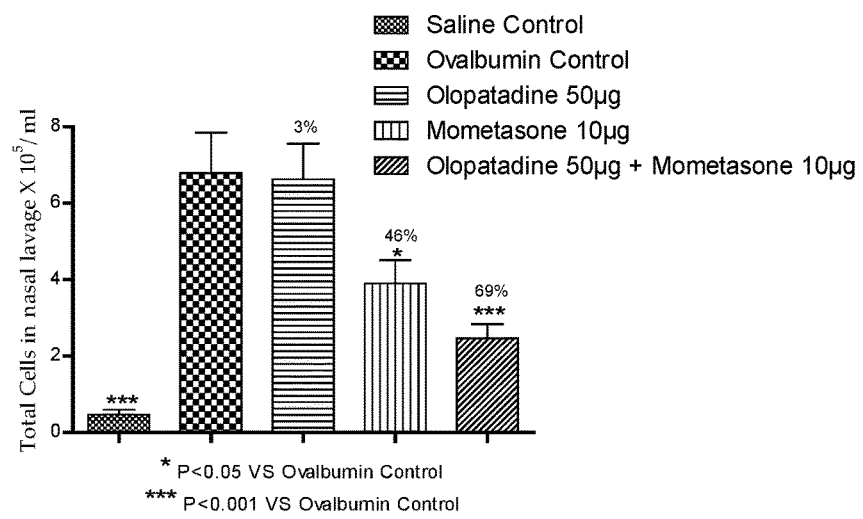
FIG. 2 is a bar graph depicting the effect of a saline control, ovalbumin control, olopatadine hydrochloride (equivalent to 50 μg olopatadine base), mometasone furoate (10 μg), and a combination of mometasone furoate (10 μg) and olopatadine hydrochloride (equivalent to 50 μg olopatadine base) on total cell count in the nasal lavage of guinea pigs as described in Example 1.
Figure 3:
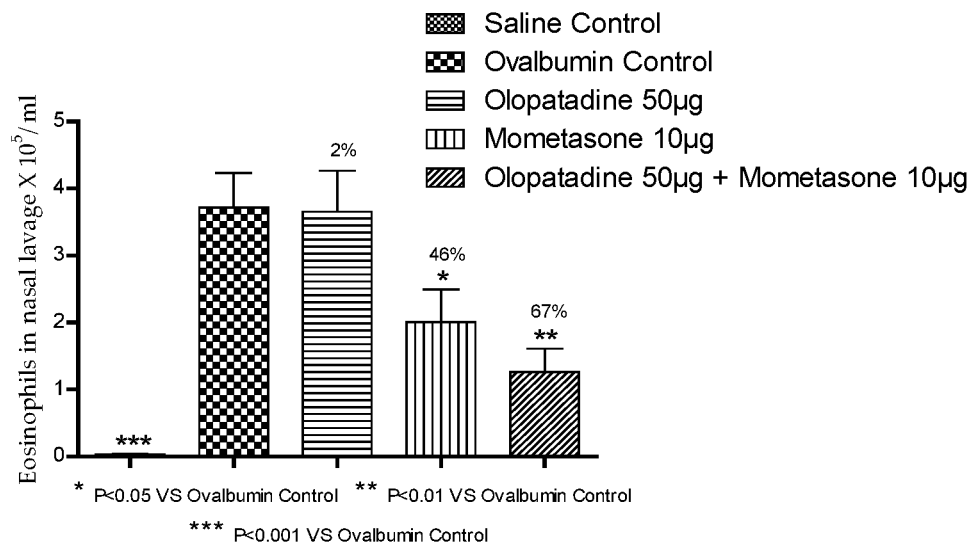
FIG. 3 is a bar graph depicting the effect of a saline control, ovalbumin control, olopatadine hydrochloride (equivalent to 50 μg olopatadine base), mometasone furoate (10 μg), and a combination of mometasone furoate (10 μg) and olopatadine hydrochloride (equivalent to 50 μg olopatadine base) on the number of eosinophils in the nasal lavage of guinea pigs as described in Example 1.

Mometasone furoate monotherapy showed significant inhibition of total cell and eosinophils in nasal lavage but was not effective in inhibiting sneezing response. Olopatadine hydrochloride monotherapy did not show significant inhibition of any of the parameters in this model. The combination of mometasone furoate with olopatadine hydrochloride showed synergy for inhibition of sneezing response (FIG. 1), cellular infiltration in nasal lavage (FIG. 2) and nasal eosinophilia (FIG. 3) as compared to respective monotherapy arms (see Table 2).

TABLE 2

Summary of the effects of a combination of mometasone furoate and olopatadine hydrochloride on ovalbumin induced rhinitis model in guinea pigs.

| Treatment | Saline control | Ovalbumin control | Olopatadine Hydrochloride (OH) | Mometasone Furoate (MF) | Combination (OH & MF)) |
|---|---|---|---|---|---|
| Dose (µg per animal) | — | — | 50 | 10 | 50 (OH) & 10 (MF) |
| Number of Sneeze (0-50 min) | 0.5** | 22 | 12.29 | 18.83 | 6* |
| Percent inhibition of sneeze | — | — | 45 | 15 | 74 |
| Total cell count × $10^5$/ml nasal lavage | 0.48*** | 6.79 | 6.63 | 3.90* | 2.46*** |
| Percent inhibition of total cell count | — | — | 3 | 46 | 69 |

TABLE 2-continued

Summary of the effects of a combination of mometasone furoate and olopatadine hydrochloride on ovalbumin induced rhinitis model in guinea pigs.

| Treatment | Saline control | Ovalbumin control | Olopatadine Hydrochloride (OH) | Mometasone Furoate (MF) | Combination (OH & MF) |
|---|---|---|---|---|---|
| Eosinophils × $10^5$/ml nasal lavage | 0.03*** | 3.71 | 3.64 | 2.00* | 1.26** |
| % inhibition of eosinophils | — | — | 2 | 46 | 67 |

*$P < 0.05$ vs. Ovalbumin Control,
**$P < 0.01$ vs. Ovalbumin Control,
***$P < 0.001$ vs. Ovalbumin control The combination of mometasone furoate and olopatadine hydrochloride showed a beneficial effect greater than the individual monotherapies. The combination of mometasone furoate and olopatadine hydrochloride showed synergy in the treatment of allergic rhinitis in this model.

Example 2

Effect of Mometasone and Olopatadine and their Combination on Ovalbumin Induced Rhinitis Model in Male Guinea Pigs The procedure in Example 1 was repeated except 120 μg of olopatadine hydrochloride (based on the equivalent weight of olopatadine free base) was used. The animal groups in Table 3 below were used during this experiment.

TABLE 3

Animal Groups

| Group | Group Code | Treatment | Ovalbumin Challenge | Animals/group |
|---|---|---|---|---|
| A | Saline Control | Vehicle | − | 9 |
| B | Ovalbumin Control | Vehicle | + | 10 |
| C | Olopatadine 120 μg | Olopatadine Hydrochloride 120 μg | + | 10 |
| D | Mometasone 10 μg | Mometasone Furoate 10 μg | + | 9 |
| E | Combination | Olopatadine Hydrochloride 120 μg + Mometasone Furoate 10 μg | + | 10 |

Compound administration was performed as in Example 1, except the dosing volume was 60 μl/animal. The saline control group and ovalbumin control group received vehicle (60 μl, 0.1% Tween 80 in distilled water). In vivo evaluations were performed as in Example 1.

Results

Figure 4:
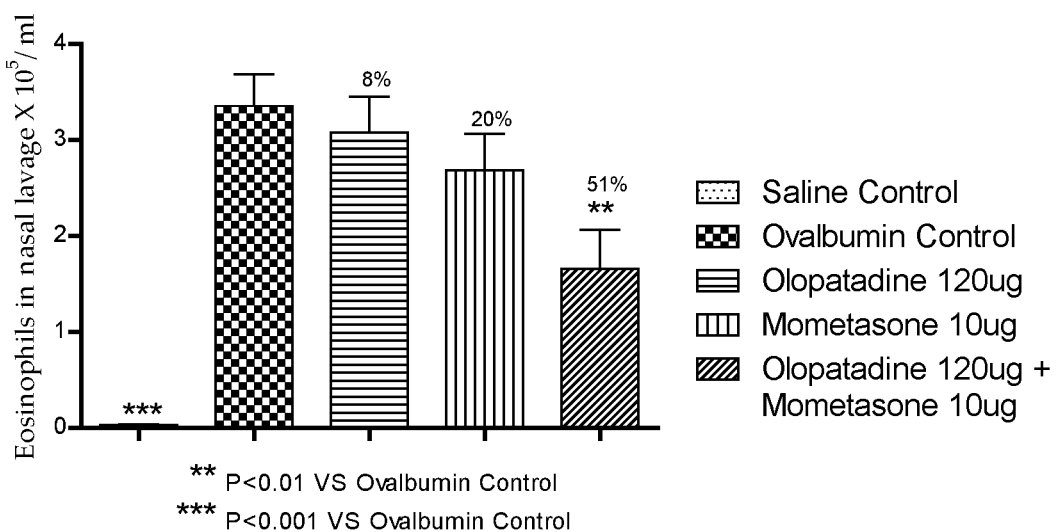
FIG. 4 is a bar graph depicting the effect of a saline control, ovalbumin control, olopatadine hydrochloride (equivalent to 120 μg olopatadine base), mometasone furoate (10 μg), and a combination of mometasone furoate (10 μg) and olopatadine hydrochloride (equivalent to 120 μg olopatadine base) on the number of eosinophils in the nasal lavage of guinea pigs as described in Example 2.
Figure 5:
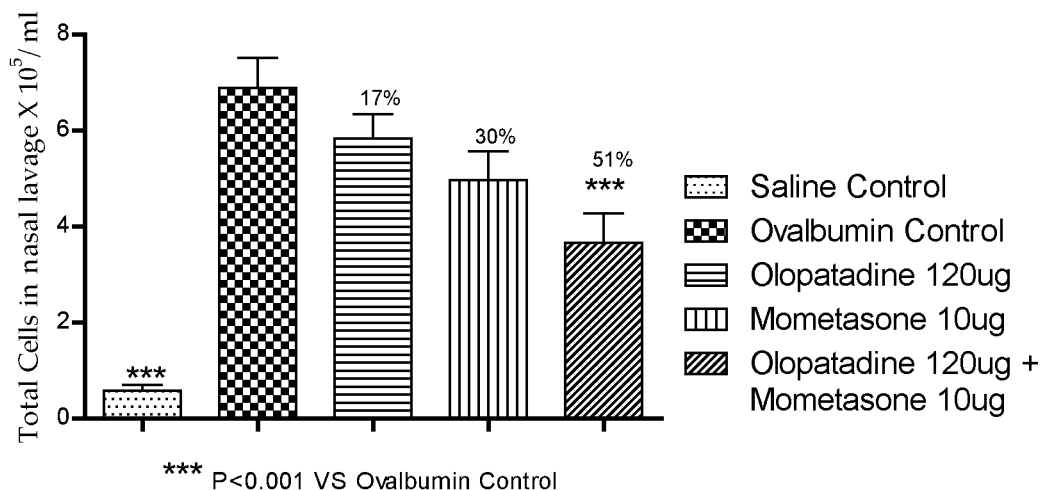
FIG. 5 is a bar graph depicting the effect of a saline control, ovalbumin control, olopatadine hydrochloride (equivalent to 120 μg olopatadine base), mometasone furoate (10 μg), and a combination of mometasone furoate (10 μg) and olopatadine hydrochloride (equivalent to 120 μg olopatadine base) on the total cell count in the nasal lavage of guinea pigs as described in Example 2.
Figure 6:
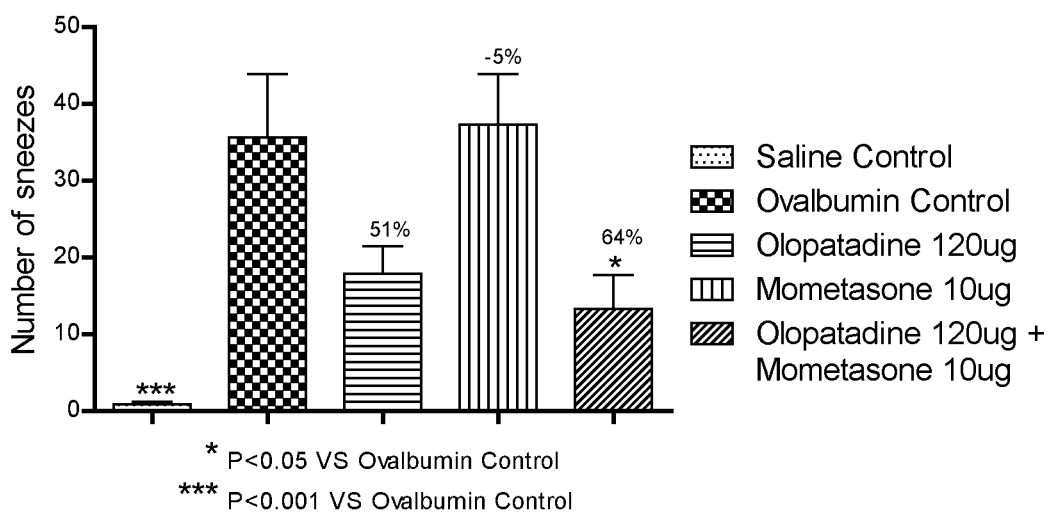
FIG. 6 is a bar graph depicting the effect of a saline control, ovalbumin control, olopatadine hydrochloride (equivalent to 120 μg olopatadine base), mometasone furoate (10 μg), and a combination of mometasone furoate (10 μg) and olopatadine hydrochloride (equivalent to 120 μg olopatadine base) on the sneezing response in guinea pigs as described in Example 2.

Mometasone monotherapy showed significant inhibition of total cell and eosinophils in nasal lavage but was not effective in inhibiting sneezing response. Olopatadine monotherapy did not show significant inhibition of any of the parameter in this model. The combination of mometasone with olopatadine showed synergy for the inhibition of nasal eosinophilia, cellular infiltration in nasal lavage and sneezing response as compared to the respective monotherapies (see FIGS. 4-6 and Table 4).

TABLE 4

Summary of the effects of combination of mometasone and olopatadine on ovalbumin induced rhinitis model in guinea pigs

| Treatment | Saline control | Ovalbumin control | Olopatadine Hydrochloride (OH) | Mometasone Furoate (MF) | Combination (OH & MF) |
|---|---|---|---|---|---|
| Dose (μg per animal) | — | — | 120 | 10 | 120 (OH) & 10 (MF) |
| Number of Sneeze (0-50 min) | 0.89*** | 35.70 | 17.90 | 37.33 | 13.30* |
| Percent inhibition of sneeze | — | — | 51 | −5 | 64 |
| Total cell count × $10^5$/ml nasal lavage | 0.58*** | 6.88 | 5.83 | 4.96 | 3.66*** |
| Percent inhibition of total cell count | — | — | 17 | 30 | 51 |
| Eosinophils × $10^5$/ml nasal lavage | 0.03*** | 3.36 | 3.08 | 2.69 | 1.66** |

TABLE 4-continued

Summary of the effects of combination of mometasone and olopatadine on ovalbumin induced rhinitis model in guinea pigs

| Treatment | Saline control | Ovalbumin control | Olopatadine Hydrochloride (OH) | Mometasone Furoate (MF) | Combination (OH & MF) |
|---|---|---|---|---|---|
| % inhibition of eosinophils | — | — | 8 | 20 | 51 |

\*P < 0.05 vs. Ovalbumin Control,
\*\*P < 0.01 vs. Ovalbumin Control,
\*\*\*P < 0.001 vs. Ovalbumin Control The combination of mometasone furoate and olopatadine hydrochloride showed a beneficial effect greater than the individual monotherapies. The combination of mometasone and olopatadine showed synergy in this guinea pig rhinitis model.

Example 3

Clinical Study of Fixed Dose Combination of Mometasone and Olopatadine Nasal Spray in Human Patients The study was a single-centre, double blind, double-dummy, randomized, parallel-group, comparative Environmental Exposure Chamber (EEC) study to evaluate the efficacy, safety and tolerability of (i) two fixed dose combination products of mometasone furoate and olopatadine hydrochloride nasal spray, (ii) a fixed dose combination of azelastine hydrochloride and fluticasone propionate nasal spray (DYMISTA®), (iii) olopatadine nasal spray (PATANASE®), and (iv) a placebo nasal spray in patients with seasonal allergic rhinitis (SAR).

Key Objectives
  To evaluate the efficacy of two strengths of the fixed dose combination (FDC) of mometasone furoate and olopatadine hydrochloride nasal spray when compared with a placebo nasal spray.
  To evaluate the comparative efficacy of (i) two regimens of FDC products containing mometasone furoate and olopatadine hydrochloride nasal spray, (ii) a fixed dose combination of azelastine hydrochloride and fluticasone propionate nasal spray (DYMISTA®), and (iii) Olopatadine nasal spray (PATANASE®).
  To compare the efficacy of (i) a fixed dose combination of azelastine hydrochloride and fluticasone propionate nasal spray and (ii) olopatadine nasal spray, when compared with a placebo nasal spray.
  To compare the onset of action between active treatments groups after the first dose defined as "the first time point after initiation of treatment when the drug demonstrates a significant reduction in instantaneous TNSS compared to the placebo treatment that proves durable from this point."
  To compare the EEC-Quality of Life Questionnaire (QoLQ) and tolerability and acceptability between a fixed dose combination of mometasone furoate and olopatadine hydrochloride once daily and a fixed dose combination of mometasone furoate and olopatadine hydrochloride twice daily.
  To evaluate the comparative safety between the various treatment arms.

Sample Size
  A total of 36 patients per treatment arm were randomized in the study. The total number of randomized subjects throughout the five treatment arms was 180.

Patient Population
  Subjects suffering from seasonal allergic rhinitis for the last two years that require treatment either with intranasal antihistamines and/or intranasal steroids were included in the study.

Key Subject Selection Criteria
  1. Patients age ≥18 and ≤65 years inclusive of either sex;
  2. Patient with a known clinical history of seasonal allergic rhinitis (for at least 2 years) and exhibiting a positive skin prick test (wheal diameter at least 3 mm greater than saline control) to one of the regional allergens;
  3. Patients with the ability to understand and sign a written informed consent form, which must have been obtained prior to screening; and
  4. Patients willing to comply with the protocol requirements.

Study Design
  Patients were randomized to treatment in a 1:1:1:1:1 ratio to the following five treatment arms, at one study site:
  1. Fixed dose combination of olopatadine hydrochloride 665 mcg and mometasone furoate 25 mcg twice daily (BID)
  2. Fixed dose combination of olopatadine hydrochloride 665 mcg and mometasone furoate 50 mcg once daily (QD)
  3. DYMISTA® nasal spray (azelastine hydrochloride 137 mcg+fluticasone propionate 50 mcg) Spray twice daily (BID)
  4. PATANASE® nasal spray (olopatadine hydrochloride 665 mcg) twice daily (BID)
  5. Placebo nasal spray The double-dummy design including four masked nasal spray bottles (two for evening dosing and two for morning dosing) were utilized for this study (see Table A).

TABLE A

Treatment Administration Using Four Masked Bottles of Nasal Sprays

| | Morning | | Evening | |
|---|---|---|---|---|
| Treatment Arm | 1st bottle | 2nd bottle | 1st bottle | 2nd bottle |
| 1 TP-1: Fixed dose combination of mometasone furoate 25 mcg + olopatadine hydrochloride 665 mcg twice daily (BID) | Active | Active | Active | Active |

TABLE A-continued

Treatment Administration Using Four Masked Bottles of Nasal Sprays

| Treatment Arm | Morning | | Evening | |
| --- | --- | --- | --- | --- |
| | 1st bottle | 2nd bottle | 1st bottle | 2nd bottle |
| 2 TP-2: Fixed dose combination of mometasone furoate 50 mcg + olopatadine hydrochloride 665 mcg once daily (QD) | Active | Active | Placebo | Placebo |
| 3 DYMISTA ® twice daily (BID) | Placebo | Active | Placebo | Active |
| 4 PATANASE ® twice daily (BID) | Active | Active | Active | Active |
| 5 Placebo | Placebo | Placebo | Placebo | Placebo |

This study consisted of five visits to the study site and a 12 day at-home dosing period (and 2 days of onsite dosing—a total of 14 days of dosing). Assessment of efficacy endpoints were done out of season, in an EEC facility. After the initial screening visit (Visit 1), patients who met all study criteria (including the main criteria for inclusion: a positive skin prick test (SPT) and a 2 year medical history of allergic rhinitis (AR) to ragweed allergen) underwent further screening/priming in the EEC (Visit 2). During the EEC session patients were exposed to ragweed pollen at a concentration of 3500±500 particles/m$^3$ for 6 hours. Patients used an electronic diary (ePDAT™) to rate their ocular and nasal symptoms every 30 minutes in the EEC Patients who met a minimum qualifying TNSS of 6/12, including a score of at least 2 for nasal congestion on two consecutive diary entries continued in the study. At Visit 3, on the following day (Day 1), patients who met the minimum criteria returned to the EEC for a second consecutive EEC session. Patients were exposed to allergen for approximately 10 hours during this visit. During the first 6 hours, patients used the electronic diary to complete symptom assessments every 30 minutes and met the minimum qualifying symptom score in order to continue. Those who met the minimum qualifying symptom score were randomized to receive one of the five study drugs after the 6 hours time point in the EEC. After dosing (at approximately noon), patients were asked to complete symptom assessments at 5 minute, 10 minutes, 15 minutes, 25 minutes, 30 minute, 45 minutes, 60 minutes and then every 30 minutes for the remainder of the visit Post-treatment symptom assessments in the EEC were used to determine onset of action for study treatments. Patients were then sent home with their study medication to continue at-home BID dosing starting from the evening dose for Day 1. Patients continued at-home dosing for a period of 12 days. Following the 12 days (Days 2-13) of at-home dosing, patients returned to the EEC on Day 14 (Visit 4) for a post-treatment 6-hour priming EEC session. Patients were dosed with the morning dose of study drug one hour prior to entering the EEC. Symptoms were assessed every 30 minutes in the EEC Patients took their last dose of study treatment at midnight on the same day, and returned on the following morning (Day 15, Visit 5) for a 6 hour EEC session Over a period of 6 hours, patients used the electronic diary to complete symptom assessments every 30 minutes. In addition to collection of nasal and ocular symptoms, the electronic diary was used to collect EEC-Quality-of-Life Questionnaires (EEC-QoLQ) at Visits 2, 3, 4 and 5, and acceptability and tolerability at Visit 5. Visit 5 was the final visit for the study.

Priming

Fulfillment of the following criteria on each of two consecutive diary cards reading at priming visit: minimum TNSS of 6 out of 12, including a score of at least 2 for nasal congestion.

Randomization

Patients meeting these same criteria at both priming visits of 3 hours chamber duration in order to proceed to the treatment visit (Visit 3).

At the treatment visit (Visit 3), a minimum TNSS of 6 out of 12 (including a score of at least 2 for nasal congestion).

Drug Formulations

The test product formulations used in the study were as follows:

Test Product 1 (TP-1)

Mometasone Furoate Monohydrate and Olopatadine Hydrochloride Nasal Spray (25 mcg+600 mcg)

Each spray delivered mometasone furoate monohydrate equivalent to 25 mcg mometasone furoate and olopatadine hydrochloride equivalent to 600 mcg olopatadine.

Test Product 2 (TP-2)

Mometasone Furoate Monohydrate and Olopatadine Hydrochloride Nasal Spray (50 mcg+600 mcg)

Each spray delivered mometasone furoate monohydrate equivalent to 50 mcg mometasone furoate and olopatadine hydrochloride equivalent to 600 mcg olopatadine.

Dosage Regimen

1. Investigational Products

TP-1: Fixed dose combination of Olopatadine hydrochloride (665 mcg) and Mometasone furoate (25 mcg) Nasal Spray: 2 sprays per nostril were delivered Twice daily (BID) for two weeks.

TP-2: Fixed dose combination of Olopatadine hydrochloride (665 mcg) and Mometasone furoate (50 mcg) Nasal Spray: 2 sprays per nostril were delivered once daily (QD) for two weeks 2. Reference Therapies Olopatadine hydrochloride Nasal Spray (PATANASE® 0.6%): 2 sprays per nostril were delivered twice daily for two weeks.

DYMISTA® (azelastine hydrochloride+fluticasone propionate) 137 mcg/50 mcg Nasal Spray: 1 spray per nostril was delivered twice daily for two weeks.

Placebo Nasal Spray (based on vehicle of Investigational product): 2 sprays per nostril were delivered twice daily for two weeks.

Key Evaluation Criteria (Clinical Endpoints)

Change from baseline in mean post-treatment Total Nasal Symptoms Score (TNSS) over placebo for fixed dose combination of mometasone furoate and olopatadine hydrochloride. Mean TNSS were calculated over 6 hours in the EEC for post-treatment at Visit 5 (over hours 18 to 24 after the first dosing on Day 14) and matched baseline TNSS in the EEC at Visit 3 (over 6 hours prior to first dosing).

Change from baseline in mean post-treatment TNSS for two regimens of fixed dose combination of mometasone furoate and olopatadine hydrochloride with reference products: DYMISTA® nasal spray and PATANASE® nasal spray. Mean TNSS were calculated over 6 hours in the EEC for post-treatment at Visit 5 (over hours 18 to 24 after the first dosing on Day 14) and matched baseline TNSS in the EEC at Visit 3 (over 6 hours prior to first dosing).

Change from baseline in mean post-treatment TNSS for two regimens of fixed dose combination of mometasone furoate and olopatadine hydrochloride, DYMISTA® nasal spray and PATANASE® nasal spray. Mean post-treatment TNSS were calculated over 6 hours in the EEC for post-treatment at Visit 4 (over hours 1 to 7 after first dosing on Day 14) and matched baseline TNSS in the EEC at Visit 2 (over 6 hours).

Change from baseline in mean post-treatment TNSS for two regimens of fixed dose combination of mometasone furoate and olopatadine hydrochloride compared with reference products: DYMISTA® nasal spray and PATANASE® nasal spray. Mean TNSS were calculated over 12 hours in the EEC for post-treatment (at Visit 4 over 1 to 7 hours after first dosing on Day 14, and at Visit 5 over 18 to 24 hours after first dosing on Day 14) and matched baseline TNSS in the EEC at Visit 2 and Visit 3 (over 12 hours prior to first dosing).

Onset of Action for each treatment of fixed dose combination of mometasone furoate and olopatadine hydrochloride, DYMISTA® and PATANASE® were assessed by comparing change from baseline in post-treatment TNSS between each active treatment and placebo at every time point after the first treatment. Change from baseline in TNSS were calculated at every time point after the first dose of study treatment in the EEC at Visit 3 (i.e., over the last four hours in the EEC at Visit 3) with baseline (Visit 3) defined as the average of the last two time points pre-dosing.

Change from baseline in mean post-treatment Total Symptoms Score (TSS), Individual Nasal Symptoms Scores (NSS, four nasal symptoms of rhinorrhea, pruritus, sneezing and nasal congestion) and TOSS over 6 hours in the EEC at Visit 5 and matched baseline at Visit 3 (over 6 hours prior to first dosing).

Change from baseline in mean post-treatment Total Symptoms Score (TSS), Individual Nasal Symptoms Scores (NSS, four nasal symptoms of rhinorrhea, pruritus, sneezing and nasal congestion) and TOSS over the 6 hours in the EEC at Visit 4 and matched baseline at Visit 2 (over the 6 hours in the EEC).

Change from baseline in mean post-treatment Total Symptoms Score (TSS), Individual Nasal Symptoms Scores (NSS, four nasal symptoms of rhinorrhea, pruritus, sneezing and nasal congestion) and TOSS over 12 hours in the EEC at Visit 4 and Visit 5 and matched baseline over 12 hours in the EEC prior to dosing at Visit 2 and Visit 3.

EEC-QoLQ for all treatment arms by comparing 1) pre-EEC-QoLQ at baseline (Visit 2) with pre-EEC at Visit 4; 2) post-EEC at baseline Visit 2 with post-EEC at Visit 4; 3) after 6 hours in the EEC at Visit 3 (prior to first dosing) with post-EEC at Visit 5.

Reflective tolerability and acceptability for treatment arms compared to placebo post-EEC at Visit 5.

Results

Table B shows a summary of the TNSS change from baseline to post-treatment over 6 hours in EEC (ITT Population).

TABLE B

| Parameters | | Placebo | TP-1 | TP-2 | DYMISTA ® ® (Reference) | PATANASE (Reference) |
|---|---|---|---|---|---|---|
| | N | 36 | 36 | 36 | 36 | 36 |
| Baseline EEC | Mean | 7.64 | 8.07 | 8.20 | 8.67 | 8.27 |
| EEC at the end of treatment (2 weeks) | Mean | 6.61 | 3.31 | 3.94 | 4.80 | 6.38 |
| % Change from Baseline | | — | 13.35 | 58.98 | 51.95 | 45.67 | 22.85 |

Table C shows a summary of the TNSS change from baseline to post-treatment over 12 hours in EEC (ITT Population). (The data for NASONEX in Table C is sourced from its U.S. FDA approved label.)

TABLE C

| Parameters | | TP-1 | TP-2 | PATANASE ® (Reference) | NASONEX ®* | DYMISTA ® (Reference) |
|---|---|---|---|---|---|---|
| | N | 36 | 36 | 36 | 176 | 36 |
| Baseline EEC | Mean | 7.58 | 7.85 | 7.90 | 9.60 | 8.25 |
| EEC at the end of treatment (2 weeks) | Mean | 2.85 | 3.36 | 5.72 | — | 4.34 |
| % Change from Baseline | | 62.4 | 57.07 | 27.5 | 27.92 | 48.24 |

*NASONEX ® (mometasone furoate nasal spray) US FDA Approved label (Jan. 19, 2011)

Table D shows a summary of the TOSS change from baseline to post-treatment over 12 hours in EEC (ITT Population).

TABLE D

| | Parameters | TP-1 | TP-2 | PATANASE ® (Reference) | DYMISTA ® (Reference) |
|---|---|---|---|---|---|
| | N | 36 | 36 | 36 | 36 |
| Baseline EEC | Mean | 3.97 | 4.17 | 3.92 | 4.54 |
| EEC at the end of treatment (2 weeks) | Mean | 1.97 | 2.34 | 2.82 | 2.82 |
| % Change from Baseline | — | 50.37 | 43.6 | 28.3 | 37.88 |

The results of the study show that a combination of mometasone furoate and olopatadine hydrochloride, when administered nasally to a human patient, provides an effective treatment of seasonal allergic rhinitis and clinically significant reduction in both nasal and non-nasal symptoms associated therewith. The magnitude of this relief for TNSS was clinically relevant (i.e., greater than 2 units in difference—which is generally considered as clinically relevant—between the Test Products and Placebo). Test Product-1 showed overall better symptom relief as compared to the Reference Products (PATANASE® and DYMISTA®). Onset of action occurred by 10 minutes for TP-1 based on iTNSS change from baseline after the first dose at Visit 3 (−1.26). However, onset of action could not be defined for TP-2, DYMISTA, and PATANASE as statistically significant differences in iTNSS change from baseline between these treatments and placebo treatment were not observed at any 2 consecutive time points.

Example 4

Phase II Clinical Study of Fixed Dose Combination of Mometasone and Olopatadine Nasal Spray in Human Patients The study is a double-blind, randomized, parallel-group, comparative study to evaluate the efficacy, safety and tolerability of two different strengths and regimens of a fixed dose combination of mometasone furoate and olopatadine hydrochloride nasal spray compared with a placebo nasal spray and individual monotherapy formulations of olopatadine hydrochloride nasal spray and mometasone furoate nasal spray, in subjects (12 years of age and older) with seasonal allergic rhinitis (SAR).

Key Objectives

To compare the efficacy of mometasone furoate and olopatadine hydrochloride nasal spray once daily and mometasone furoate and olopatadine hydrochloride nasal spray twice daily with the placebo nasal spray and with the individual constituent monotherapies at the same dose in the same vehicle over 14 days of study treatment.

To compare the onset of action between mometasone furoate and olopatadine hydrochloride nasal spray once daily and mometasone furoate and olopatadine hydrochloride nasal spray twice daily with the placebo and the individual constituent monotherapies at the same dose in the same vehicle, after the first dose of study drug administration.

To assess the safety and tolerability of individual treatment arms.

TABLE E

| Investigational products and their administration | | |
|---|---|---|
| Code | Investigational product(s) | Administration |
| TP-1 | Olopatadine hydrochloride + mometasone furoate (665 µg + 25 µg) nasal sprays | Twice daily (BID) in morning and evening |
| TP-2 | Olopatadine hydrochloride + mometasone furoate (665 µg + 50 µg) nasal spray | Once daily (QD) in morning |
| GO-1 | Olopatadine hydrochloride (665 µg) nasal spray | Once daily (QD) in morning |
| GO-2 | Olopatadine hydrochloride (665 µg) nasal spray | Twice daily (BID) in morning and evening |
| GM-1 | Mometasone furoate (50 µg) nasal spray | Once daily (QD) in morning |
| GM-2 | Mometasone furoate (25 µg) nasal spray | Twice daily (BID) in morning and evening |

Sample Size:

A total of 1,106 randomized subjects (158 subjects per treatment arm) were enrolled in the study.

Key Subject Selection Criteria:

Age ≥12 and older inclusive of either sex.

Documented clinical history of SAR (for at least 2 years preceding the screening visit) with exacerbations (clinical evidence of active symptoms) and exhibiting a documented positive SPT (wheal diameter at least 5 mm greater than control wheal) to mountain cedar allergen.

A 12-hour reflective TNSS ≥8 out of a possible 12 and a congestion score of ≥2 for the AM assessment at the Screening Visit (Visit 1).

Study Design:

Subjects were randomized to treatment in a 1:1:1:1:1:1:1 ratio to the following seven treatment arms, at multiple study sites.

The double-dummy design including two identical nasal spray bottles (one for morning [AM] dosing and one for evening [PM] dosing) are utilized for this study (Table F). The double-dummy design is ensured for adequate blinding considering that treatments being compared vary in dosing frequency (BID compared with QD).

TABLE F

Treatment Administration Using Two Identical Bottles of Nasal Sprays
(2 sprays per nostril, total 4 sprays each bottle, per day)

| Code | Treatment Arm | Morning (AM) 1st bottle | Evening (PM) 2nd bottle |
|------|---------------|-------------------------|-------------------------|
| TP-1 | Olopatadine hydrochloride 665 µg + mometasone furoate 25 µg twice daily (BID) | Active | Active |
| TP-2 | Olopatadine hydrochloride 665 µg + mometasone furoate 50 µg once daily (QD) | Active | Placebo |
| GO-1 | Olopatadine hydrochloride nasal spray (665 µg) once daily (QD) | Active | Placebo |
| GO-2 | Olopatadine hydrochloride nasal spray (665 µg) twice daily (BID) | Active | Active |
| GM-1 | Mometasone furoate nasal spray (50 µg) once daily (QD) | Active | Placebo |
| GM-2 | Mometasone furoate nasal spray (25 µg) twice daily (BID) | Active | Active |
| Pbo | Placebo nasal spray | Placebo | Placebo |

This study consisted of four visits to the study site. After the initial screening visit (Visit 1), subjects who met all study selection criteria were required to undergo a single-blind placebo run-in period for 7-10 days. Following the completion of the run-in period, eligible subjects meeting the randomization criteria were enrolled and randomized to one of the seven treatment arms. Subjects were dispensed medication as per the randomization list. Randomized subjects were required to undergo a 2 week (14 days) treatment period as per the protocol to assess the efficacy and safety of the assigned treatment.

Key Evaluation Criteria (Clinical Endpoints):
Primary Endpoint
  Change from baseline in average AM and PM subject-reported 12-hour rTNSS (reflective TNSS) over the 14-day treatment period.
Secondary Endpoints
  Change from baseline in average AM and PM subject-reported 12-hour iTNSS (instantaneous TNSS) over the 14 day treatment period.
  Change from baseline in average AM and PM subject-reported 12-hour rTOSS (reflective TOSS) over the 14-day treatment period.
  Onset of action for each treatment are assessed by comparing the change from baseline in post-treatment iTNSS between each active treatment and placebo at defined time points (prior to first dose (pre-dose), 15 min, 30 min, 45 min, 60 min, 90 min, 120 min, 150 min, 180 min, 210 min, and 240 min) after the first study treatment for 4 hours.
  Change from baseline in the rhinoconjunctivitis quality of life questionnaire (RQLQ) on day 15 between treatment arms for subjects with impaired quality of life at baseline as defined by the RQLQ Score at the randomization visit (RV) of 3.0 or greater (RQLQ population).
Tertiary Efficacy Endpoints
Nasal Symptoms:
  Change from baseline in AM subject-reported rTNSS over the 14-day treatment period.
  Change from baseline in AM subject-reported iTNSS over the 14-day treatment period.
  Change from baseline in PM subject-reported rTNSS over the 14-day treatment period.
  Change from baseline in PM subject-reported iTNSS over the 14-day treatment period.
  Change from baseline in subject-reported reflective individual nasal symptoms over the 14-day treatment period (AM, PM and average of AM and PM).
  Change from baseline in subject-reported instantaneous individual nasal symptoms over the 14-day treatment period (AM, PM and average of AM and PM).
  Change from baseline in average AM and PM subject-reported rTNSS and iTNSS for each day.
  Change from baseline in AM subject-reported rTNSS and iTNSS for each day.
  Change from baseline in PM subject-reported rTNSS and iTNSS for each day.
Ocular Symptoms:
  Change from baseline in average AM and PM subject-reported iTOSS (instantaneous TOSS) over the 14-day treatment period.
  Change from baseline in AM subject-reported rTOSS over the 14-day treatment period.
  Change from baseline in AM subject-reported iTOSS over the 14-day treatment period.
  Change from baseline in PM subject-reported rTOSS over the 14-day treatment period.
  Change from baseline in PM subject-reported iTOSS over the 14-day treatment period.
  Change from baseline in subject-reported reflective individual ocular symptoms over the 14-day treatment period (AM, PM and average AM and PM).
  Change from baseline in subject-reported instantaneous individual ocular symptoms over the 14-day treatment period (AM, PM and average AM and PM).
  Change from baseline in average of the AM and PM subject-reported rTOSS and iTOSS for each day.
  Change from baseline in AM subject-reported rTOSS and iTOSS for each day.
  Change from baseline in PM subject-reported rTOSS and iTOSS for each day.
The non-nasal symptoms are assessed in a similar manner to the ocular symptoms above.
Physician Assessed Nasal Symptom Score (PNSS) and Rhinoconjuntivitis Quality of Life Questionnaire (RQLQ):
  Physician assessed Nasal Symptom Score (PNSS) and physician assessed individual nasal symptoms at Day 15 (Visit 4).
  Individual domains of the RQLQ at Day 15 (Visit 4) for the RQLQ population (defined as subject with impaired Quality of Life at baseline).
  RQLQ at Day 15 (Visit 4) for the full analysis set (FAS).
Results
  Table G shows a summary of the primary clinical endpoint (rTNSS) and secondary clinical endpoints (iTNSS, rTOSS, onset of action and RQLQ) observed during this Phase II study. For comparison of the combination therapy against a monotherapy, a p-value below 0.05 is considered statistically significant.

TABLE G

| Treatment Arm | Primary Clinical Endpoint rTNSS | Secondary Clinical endpoints | | | | |
|---|---|---|---|---|---|---|
| | | iTNSS | rTOSS | Onset of Action | RQLQ | |
| TP-2 vs Pbo | -1.10* p < 0.001* | -1.10 p < 0.001* | -0.55 p = 0.004* | 150 min. Statistically significant at all time points after 150 min (except 180 min)* | -0.48 p = 0.004* | |
| TP-2 vs GO-1 | -0.77 p = 0.002* | -0.86 p = 0.0003* | -0.36 p = 0.65 | NA | -0.29 p = 0.085 | |
| TP-2 vs GM-1 | -0.35 p = 0.15 | -0.34 p = 0.145 | -0.37 p = 057 | NA | -0.13 p = 0.429 | |
| TP-1 vs Pbo | -1.17* p < 0.001* | -1.10 p < 0.001* | -0.41 p = 0.032 | Not statistically significant at all time points | -0.56 p = 0.0009* | |
| TP-1 vs GO-2 | -0.49 p = 0.048* | -0.45 p = 0.058 | -0.03 p = 0.849 | NA | -0.25 p = 0.135 | |
| TP-1 vs GM-2 | -0.71 p = 0.004* | -0.65 p = 0.006* | -0.40 p = 040* | NA | -0.41 p = 0.014* | |

*indicates statistical significance

As can be seen from Table G, the combination of mometasone fuorate and olopatadine hydrochloride, when administered once daily (TP-2) or twice daily (TP-1) is statistically superior to placebo (p<0.0001) for the primary endpoint, change in rTNSS from baseline. The combination of mometasone fuorate and olopatadine hydrochloride, when administered once daily (TP-2) or twice daily (TP-1) also met secondary clinical endpoints in the trial, supportive of its efficacy in the treatment of seasonal allergic rhinitis (SAR). The combination of mometasone fuorate and olopatadine hydrochloride, when administered twice daily (TP-1) was also statistically superior to the individual monotherapies (GO-2 and GM-2) for both primary (rTNSS) and secondary endpoints (iTNSS).

Table G2 shows the least squares mean difference in individual reflective nasal symptoms scores for TP-1 and TP-2 versus placebo.

TABLE G2

Least Squares Mean Difference in Individual Reflective Nasal Symptom Scores with TP-1 or TP-2 versus Placebo

| | Least squares mean difference (97.5% confidence interval) | P value |
|---|---|---|
| TP-1 | | |
| Rhinorrhea | -0.27 (-0.42, -0.12) | <0.001 |
| Nasal congestion | -0.24 (-0.38, -0.99) | <0.001 |
| Nasal itching | -0.27 (-0.43, -0.11) | <0.001 |
| Sneezing | -0.39 (-0.57, -0.22) | <0.001 |
| TP-2 | | |
| Rhinorrhea | -0.26 (-0.40, -0.11) | <0.001 |
| Nasal congestion | -0.22 (-0.37, -0.08) | <0.001 |
| Nasal itching | -0.26 (-0.42, -0.10) | <0.001 |
| Sneezing | -0.37 (-0.55, -0.20) | <0.001 |

Table H shows a summary of the treatment emergent adverse events (TEAEs) observed during this Phase II study.

TABLE H

| | Pbo (N = 159) | TP-2 (N = 158) | GM-1 (N = 160) | GO-1 (N = 158) | TP-1 (N = 157) | GM-2 (N = 159) | GO-2 (N = 160) |
|---|---|---|---|---|---|---|---|
| At least 1 TEAE | 13 (8.2%) | 15 (9.5%) | 15 (9.4%) | 17 (10.8%) | 17 (10.8%) | 10 (6.3%) | 25 (15.6%) |
| Dysgeusia | 0 | 2 (1.3%) | 0 | 2 (1.3%) | 2 (1.3%) | 0 | 5 (3.1%) |
| Headache | 1 (0.6%) | 6 (3.8%) | 2 (1.3%) | 1 (0.6%) | 0 | 1 (0.6%) | 1 (0.6%) |

All TEAEs were mild to moderate. Dysgeusia (1.3%) and headache (1.9%) were adverse events (AEs) reported for the combination of mometasone fuorate and olopatadine hydrochloride administered twice daily (BID) and once daily (QD), respectively.

Example 5

Phase III Clinical Study of Fixed Dose Combination of Mometasone and Olopatadine Nasal Spray in Human Patients with SAR, Spring Season This study was a double-blind, randomized, parallel-group, comparative study to evaluate the efficacy, safety and tolerability of a fixed dose combination of mometasone furoate and olopatadine hydrochloride nasal spray compared with a placebo nasal spray and individual monotherapy formulations of olopatadine hydrochloride nasal spray and mometasone furoate nasal spray, in subjects (12 years of age and older) with seasonal allergic rhinitis (SAR), spring season.

Study Objectives
To compare the efficacy of mometasone furoate and olopatadine hydrochloride nasal spray twice daily with the placebo nasal spray and with the individual constituent monotherapies at the same dose in the same vehicle over 14 days of study treatment.
To assess the safety and tolerability of individual treatment arms.
To investigate the pharmacokinetics (PK) of mometasone furoate and olopatadine hydrochloride nasal spray twice daily treatment.

TABLE I

Investigational products and their administration

| Code | Investigational product(s) | Administration |
| --- | --- | --- |
| TP-1 | Olopatadine hydrochloride + mometasone furoate (665 µg + 25 µg) nasal spray | Twice daily (BID) in morning and evening |
| GO-2 | Olopatadine hydrochloride (665 µg) nasal spray | Twice daily (BID) in morning and evening |
| GM-2 | Mometasone furoate (25 µg) nasal spray | Twice daily (BID) in morning and evening |

Sample Size:
A total of 1,180 randomized subjects (295 subjects per treatment arm) were enrolled in the study.

Key Subject Selection Criteria:
Age ≥12 and older inclusive of either sex.
Documented clinical history of SAR (for at least 2 years preceding the screening visit) with exacerbations (clinical evidence of active symptoms) during the study season for mountain season pollen and exhibiting a documented positive SPT (wheal diameter at least 5 mm greater than control wheal) to mountain cedar allergen.
A 12-hour reflective TNSS ≥8 out of a possible 12 and a congestion score of ≥2 for the AM assessment at the Screening Visit (Visit 1).

Study Design:
Subjects were randomized to treatment in a 1:1:1:1 ratio to the following four treatment arms, at multiple study sites.

TABLE J

Treatment Administration Using Two Identical Bottles of Nasal Sprays (2 sprays per nostril, total 4 sprays each bottle, per day)

| Code | Treatment Arm | Morning (AM) 1$^{st}$ bottle | Evening (PM) 2$^{nd}$ bottle |
| --- | --- | --- | --- |
| TP-1 | Olopatadine hydrochloride 665 µg + mometasone furoate 25 µg twice daily (BID) | Active | Active |
| GO-2 | Olopatadine hydrochloride nasal spray (665 µg) twice daily (BID) | Active | Active |
| GM-2 | Mometasone furoate nasal spray (25 µg) twice daily (BID) | Active | Active |
| Pbo | Placebo nasal spray | Placebo | Placebo |

This study consisted of four visits to the study site. After the initial screening visit (Visit 1), subjects who met all study selection criteria were required to undergo a single-blind placebo run-in period for 7-10 days. Following the completion of the run-in period, eligible subjects meeting the randomization criteria were enrolled and randomized to one of the four treatment arms. Subjects were dispensed medication as per the randomization list. Randomized subjects were required to undergo a 2 week (14 days) treatment period as per the protocol to assess the efficacy and safety of the assigned treatment. Subjects were instructed to record the symptom scores in a symptom assessment diary. They were also scheduled to have at least two blood samples for PK assessment during the treatment period.

Key Evaluation Criteria (Clinical Endpoints):
Primary Endpoint
   Change from baseline in average AM and PM subject-reported 12-hour rTNSS (reflective TNSS) over the 14-day treatment period.
Secondary Endpoints
   Change from baseline in average AM and PM subject-reported 12-hour iTNSS (instantaneous TNSS) over the 14 day treatment period.
   Change from baseline in average AM and PM subject-reported 12-hour rTOSS (reflective TOSS) over the 14-day treatment period.
   Onset of action for each treatment are assessed by comparing the change from baseline in post-treatment iTNSS between each active treatment and placebo at defined time points (prior to first dose (pre-dose), 15 min, 30 min, 45 min, 60 min, 90 min, 120 min, 150 min, 180 min, 210 min, and 240 min) after the first study treatment for 4 hours.
   Change from baseline in the overall Rhinoconjunctivitis Quality of Life questionnaire (RQLQ)-Standardized Activities (RQLQ(S)) score on Day 15 (Visit 4) for the Full Analysis Set (FAS).
Pharmacokinetic Endpoints
   Plasma PK: Maximum plasma concentration ($C_{max}$), time to attain $C_{max}$ ($T_{max}$), and area under the plasma concentration-time curve over the dosing interval ($AUC_{tau}$) will be estimated for mometasone furoate and olopatadine on Day 1 and Day 8 based on the pharmacokinetic analysis set (PKAS).
Tertiary Efficacy Endpoints
Nasal Symptoms:
   Change from baseline in AM subject-reported rTNSS over the 14-day treatment period.
   Change from baseline in AM subject-reported iTNSS over the 14-day treatment period.

Change from baseline in PM subject-reported rTNSS over the 14-day treatment period.

Change from baseline in PM subject-reported iTNSS over the 14-day treatment period.

Change from baseline in subject-reported reflective individual nasal symptoms over the 14-day treatment period (AM, PM and average of AM and PM).

Change from baseline in subject-reported instantaneous individual nasal symptoms over the 14-day treatment period (AM, PM and average of AM and PM).

Change from baseline in average AM and PM subject-reported rTNSS and iTNSS for each day.

Change from baseline in AM subject-reported rTNSS and iTNSS for each day.

Change from baseline in PM subject-reported rTNSS and iTNSS for each day.

Ocular Symptoms:

Change from baseline in average AM and PM subject-reported iTOSS (instantaneous TOSS) over the 14-day treatment period.

Change from baseline in AM subject-reported rTOSS over the 14-day treatment period.

Change from baseline in AM subject-reported iTOSS over the 14-day treatment period.

Change from baseline in PM subject-reported rTOSS over the 14-day treatment period.

Change from baseline in PM subject-reported iTOSS over the 14-day treatment period.

Change from baseline in subject-reported reflective individual ocular symptoms over the 14-day treatment period (AM, PM and average AM and PM).

Change from baseline in subject-reported instantaneous individual ocular symptoms over the 14-day treatment period (AM, PM and average AM and PM).

Change from baseline in average of the AM and PM subject-reported rTOSS and iTOSS for each day.

Change from baseline in AM subject-reported rTOSS and iTOSS for each day.

Change from baseline in PM subject-reported rTOSS and iTOSS for each day.

The non-nasal symptoms are assessed in a similar manner to the ocular symptoms above.

Physician Assessed Nasal Symptom Score (PNSS), Rhino-conjuntivitis Quality of Life Questionnaire Standardized Activities (RQLQ(S)), and Rhinitis Control Assessment Test (RCAT):

Change from baseline in PNSS and physician assessed individual nasal symptoms at Day 15 (Visit 4).

Change from baseline in individual domains of the RQLQ(S) at Day 15 (Visit 4) for the FAS.

Change from baseline in overall RQLQ(S) score and individual domains of the RQLQ(S) at Day 15 (Visit 4) for the RQLQ(S) analysis set.

Change from baseline in the RCAT at Day 15 (Visit 4).

Change from baseline in individual domains of the RCAT at Day 15 (Visit 4).

Individual domains of the RQLQ at Day 15 (Visit 4) for the RQLQ population (defined as subject with impaired Quality of Life at baseline).

RQLQ at Day 15 (Visit 4) for the full analysis set (FAS).

Results

Table K shows a summary of the primary clinical endpoint (rTNSS) and secondary clinical endpoints (iTNSS, rTOSS, onset of action and RQLQ) observed during this Phase III study. For comparison of the combination therapy against a monotherapy, a p-value below 0.05 is considered statistically significant.

TABLE K

| Treatment Arm | Primary Clinical Endpoint rTNSS | Secondary Clinical endpoints | | | |
|---|---|---|---|---|---|
| | | iTNSS | rTOSS | Onset of Action | RQLQ |
| TP-1 vs Pbo | −0.98 p < 0.0001* | −0.93 p < 0.0001* | −0.49 p = 0.0014* | 15 min Statistically significant at all time points | −0.43 p = 0.0001 |
| TP-1 vs GO-2 | −0.61 p = 0.0029* | −0.50 p = 0.0050* | −0.09 p = 0.5423 | NA | −0.28 p = 0.0105 |
| TP-1 vs GM-2 | −0.39 p = 0.058 | −0.36 p = 0.0413* | −0.19 p = 0.2113 | NA | −0.20 p = 0.0692 |
| GO-2 vs Pbo | −0.37 p = 0.075 | −0.42 p = 0.0177* | −0.40 p = 0.0100 | statistically significant at 45 mins only | −0.15 p = 0.1659 |
| GM-2 vs Pbo | −0.59 p = 0.004 | −0.57 p = 0.0017* | −0.30 p = 0.0510 | Not statistically significant at all time points | −0.23 p = 0.0345 |

*indicates statistical significance.

As can be seen from Table K, the combination of mometasone fuorate and olopatadine hydrochloride, when administered twice daily (TP-1) is statistically superior to placebo (p<0.0001) for the primary endpoint, change in rTNSS from baseline, and is statistically superior to olopatadine hydrochloride monotherapy (GO-2). The secondary endpoints were also statistically significant for combination of mometasone fuorate and olopatadine hydrochloride, when administered twice daily (TP-1), supportive of its efficacy in the treatment of seasonal allergic rhinitis (SAR).

The combination of mometasone fuorate and olopatadine hydrochloride, when administered twice daily (TP-1) also exhibited a faster (rapid) onset of action (an onset of action within 15 minutes), as measured by iTNSS, when compared to olopatadine hydrochloride monotherapy or mometasone fuorate monotherapy.

All TEAEs were mild to moderate. Dysgeusia (3.3%) and headache (0.7%) reported as adverse events for the combination of mometasone fuorate and olopatadine hydrochloride administered twice daily (BID).

The pharmacokinetics (PK) of TP-1 were measured for a subset of patients in the phase III clinical study on day 1 and day 8 (steady state). The PK results for patients receiving TP-1 are provided below.

| | Olopatadine | | | Mometasone furoate | |
|---|---|---|---|---|---|
| PK parameter | Day 1 | Day 8 | PK parameter | Day 1 | Day 8 |
| $C_{max}$ (ng/mL) | n = 26 | n = 25 | $C_{max}$ (pg/mL) | n = 26 | n = 26 |
| Mean (SD) | 19.82 (6.36) | 19.80 (7.01) | Mean (SD) | 6.78 (2.71) | 9.92 (3.74) |
| CV % | 32.12 | 35.39 | CV % | 39.96 | 37.69 |
| Min-Max | 8.70-31.60 | 9.67-37.30 | Min-Max | 2.67-12.80 | 3.58-16.10 |
| Geo Mean (Geo CV %) | 18.77 (35.61) | 18.70 (35.34) | Geo Mean (Geo CV %) | 6.27 (42.80) | 9.17 (43.88) |
| $AUC_{tau}$ (ng*hr/mL) | n = 26 | n = 24 | $AUC_{tau}$ (pg*hr/mL) | n = 26 | n = 25 |
| Mean (SD) | 75.48 (20.02) | 88.77 (23.87) | Mean (SD) | 28.56 (13.33) | 58.40 (27.00) |
| CV % | 26.53 | 26.89 | CV % | 46.67 | 46.23 |
| Min-Max | 39.33-116.80 | 53.35-138.34 | Min-Max | 12.11-72.54 | 25.68-124.05 |
| Geo Mean (Geo CV %) | 72.90 (27.67) | 85.74 (27.54) | Geo Mean (Geo CV %) | 26.16 (43.51) | 52.67 (49.48) |
| $T_{max}$ (hour) | n = 26 | n = 26 | $T_{max}$ (hour) | n = 26 | n = 26 |
| Median (range) | 1.00 (0.25-3) | 1.00 (0.25-2) | Median (range) | 1.00 (0.25-2) | 1.00 (0.25-2) |

Example 6

Phase III Clinical Study of Fixed Dose Combination of Mometasone and Olopatadine Nasal Spray in Human Patients with SAR, Fall and Mountain Cedar Season This study was a double-blind, randomized, parallel-group, comparative study to evaluate the efficacy, safety and tolerability of a fixed dose combination of mometasone furoate and olopatadine hydrochloride nasal spray compared with a placebo nasal spray and individual monotherapy formulations of olopatadine hydrochloride nasal spray and mometasone furoate nasal spray, in subjects (12 years of age and older) with seasonal allergic rhinitis (SAR), fall and mountain cedar season.

Study Objectives
- To compare the efficacy of mometasone furoate and olopatadine hydrochloride nasal spray twice daily with the placebo nasal spray and with the individual constituent monotherapies at the same dose in the same vehicle over 14 days of study treatment.
- To assess the safety and tolerability of individual treatment arms.

TABLE L

Investigational products and their administration

| Code | Investigational product(s) | Administration |
|---|---|---|
| TP-1 | Olopatadine hydrochloride + mometasone furoate (665 µg + 25 µg) nasal spray | Twice daily (BID) in morning and evening |
| GO-2 | Olopatadine hydrochloride (665 µg) nasal spray | Twice daily (BID) in morning and evening |
| GM-2 | Mometasone furoate (25 µg) nasal spray | Twice daily (BID) in morning and evening |

Sample Size:
A total of 1,176 randomized subjects (~294 subjects per treatment arm) were enrolled in the study. For this study, the subject population is adult and adolescent subjects (12 years of age and older) with SAR who exhibit symptoms of SAR during the fall allergy season to the relevant seasonal allergen (e.g., ragweed).

Study Design:
Subjects were randomized to treatment in a 1:1:1:1 ratio to the following four treatment arms, at multiple study sites.

TABLE M

Treatment Administration Using Two Identical Bottles of Nasal Sprays (2 sprays per nostril, total 4 sprays each bottle, per day)

| Code | Treatment Arm | Morning (AM) 1st bottle | Evening (PM) 2nd bottle |
|---|---|---|---|
| TP-1 | Olopatadine hydrochloride 665 µg + mometasone furoate 25 µg twice daily (BID) | Active | Active |
| GO-2 | Olopatadine hydrochloride nasal spray (665 µg) twice daily (BID) | Active | Active |
| GM-2 | Mometasone furoate, nasal spray (25 µg) twice daily (BID) | Active | Active |
| Pbo | Placebo nasal spray | Placebo | Placebo |

This study consisted of four visits to the study site. After the initial screening visit (Visit 1), subjects who met all study selection criteria were required to undergo a single-blind placebo run-in period for 7-10 days. Following the completion of the run-in period, eligible subjects meeting the randomization criteria were enrolled and randomized to one of the four treatment arms. Subjects were dispensed medication as per the randomization list. Randomized subjects were required to undergo a 2 week (14 days) treatment period as per the protocol to assess the efficacy and safety of the assigned treatment. Subjects were instructed to record the symptom scores in a symptom assessment diary.

Key Evaluation Criteria (Clinical Endpoints):

Primary Endpoint
- Change from baseline in average AM and PM subject-reported 12-hour rTNSS (reflective TNSS) over the 14-day treatment period.

Secondary Endpoints
- Change from baseline in average AM and PM subject-reported 12-hour iTNSS (instantaneous TNSS) over the 14 day treatment period.
- Change from baseline in average AM and PM subject-reported 12-hour rTOSS (reflective TOSS) over the 14-day treatment period.
- Onset of action for each treatment are assessed by comparing the change from baseline in post-treatment iTNSS between each active treatment and placebo at defined time points (prior to first dose (pre-dose), 15 min, 30 min, 45 min, 60 min, 90 min, 120 min, 150 min, 180 min, 210 min, and 240 min) after the first study treatment for 4 hours.

Change from baseline in the overall Rhinoconjunctivitis Quality of Life questionnaire (RQLQ)—Standardized Activities (RQLQ(S)) score on Day 15 (Visit 4) for the Full Analysis Set (FAS).

Tertiary Efficacy Endpoints

Nasal Symptoms:
  Change from baseline in AM subject-reported rTNSS over the 14-day treatment period.
  Change from baseline in AM subject-reported iTNSS over the 14-day treatment period.
  Change from baseline in PM subject-reported rTNSS over the 14-day treatment period.
  Change from baseline in PM subject-reported iTNSS over the 14-day treatment period.
  Change from baseline in subject-reported reflective individual nasal symptoms over the 14-day treatment period (AM, PM and average of AM and PM).
  Change from baseline in subject-reported instantaneous individual nasal symptoms over the 14-day treatment period (AM, PM and average of AM and PM).
  Change from baseline in average AM and PM subject-reported rTNSS and iTNSS for each day.
  Change from baseline in AM subject-reported rTNSS and iTNSS for each day.
  Change from baseline in PM subject-reported rTNSS and iTNSS for each day.

Ocular Symptoms:
  Change from baseline in average AM and PM subject-reported iTOSS (instantaneous TOSS) over the 14-day treatment period.
  Change from baseline in AM subject-reported rTOSS over the 14-day treatment period.
  Change from baseline in AM subject-reported iTOSS over the 14-day treatment period.
  Change from baseline in PM subject-reported rTOSS over the 14-day treatment period.
  Change from baseline in PM subject-reported iTOSS over the 14-day treatment period.
  Change from baseline in subject-reported reflective individual ocular symptoms over the 14-day treatment period (AM, PM and average AM and PM).
  Change from baseline in subject-reported instantaneous individual ocular symptoms over the 14-day treatment period (AM, PM and average AM and PM).
  Change from baseline in average of the AM and PM subject-reported rTOSS and iTOSS for each day.
  Change from baseline in AM subject-reported rTOSS and iTOSS for each day.
  Change from baseline in PM subject-reported rTOSS and iTOSS for each day.

The non-nasal symptoms are assessed in a similar manner to the ocular symptoms above.

Physician Assessed Nasal Symptom Score (PNSS), Rhinoconjuntivitis Quality of Life Questionnaire Standardized Activities (RQLQ(S)), and Rhinitis Control Assessment Test (RCAT):
  Change from baseline in PNSS and physician assessed individual nasal symptoms at Day 15 (Visit 4).
  Change from baseline in individual domains of the RQLQ (S) at Day 15 (Visit 4) for the FAS.
  Change from baseline in overall RQLQ(S) score and individual domains of the RQLQ(S) at Day 15 (Visit 4) for the RQLQ(S) Analysis Set.
  Change from baseline in the RCAT at Day 15 (Visit 4).
  Change from baseline in individual domains of the RCAT at Day 15 (Visit 4).

Results

Table N shows a summary of the primary clinical endpoint (rTNSS) and secondary clinical endpoints (iTNSS, rTOSS, onset of action and RQLQ) observed during this Phase III study. For comparison of the combination therapy against a monotherapy, a p-value below 0.05 is considered statistically significant.

TABLE N

| Treatment Arm | Primary Clinical Endpoint rTNSS | Secondary Clinical Endpoints | | | |
|---|---|---|---|---|---|
| | | iTNSS | rTOSS | Onset of Action | RQLQ |
| TP-1 vs. Pbo | −1.09 ($p < 0.001$)* | −0.94 ($p < 0.001$)* | −0.52 ($p = 0.001$)* | 15 minutes. Statistically significant at all time points. | −0.45 ($p = 0.0001$)* |
| TP-1 vs. GO-2 | −0.44 ($p = 0.028$)* | −0.41 ($p = 0.0035$)* | −0.17 ($p = 0.297$) | N/A | −0.31 ($p = 0.0090$)* |
| TP-1 vs. GM-2 | −0.47 ($p = 0.019$)* | −0.51 ($p = 0.008$)* | −0.35 ($p = 0.030$)* | N/A | −0.09 ($p = 0.423$) |
| GO-2 vs. Pbo | −0.64 ($p = 0.001$)* | −0.54 ($p = 0.005$)* | −0.35 ($p = 0.029$)* | 15 minutes. Statistically significant at all time points. | −0.14 ($p = 0.221$) |
| GM-2 vs. Pbo | −0.62 ($p = 0.002$)* | −0.44 ($p = 0.023$)* | −0.17 ($p = 0.282$) | Not statistically significant at any time point. | −0.36 ($p = 0.0024$)* |

*indicates statistical significance

As can be seen from Table N, the combination of mometasone fuorate and olopatadine hydrochloride, when administered twice daily (TP-1) is statistically superior to placebo (p<0.0001) for the primary endpoint, change in rTNSS from baseline, and is statistically superior to olopatadine hydrochloride monotherapy (GO-2) and mometasone fuorate monotherapy (GM-2). The secondary endpoints were also statistically significant for combination of mometasone fuorate and olopatadine hydrochloride, when administered twice daily (TP-1), supportive of its efficacy in the treatment of seasonal allergic rhinitis (SAR).

Table N2 shows the least squares mean difference in individual reflective and instantaneous nasal symptoms scores for the TP-1 group versus the placebo group.

TABLE N2

Least Squares Mean Difference in Individual Reflective and Instantaneous Nasal Symptom Scores with TP-1 versus Placebo

| | Least squares mean difference (97.5% confidence interval) | P value |
|---|---|---|
| Reflective | | |
| Rhinorrhea | −0.30 (−0.41, −0.19) | <0.001 |
| Nasal congestion | −0.20 (−0.30, −0.09) | <0.001 |
| Nasal itching | −0.23 (−0.34, −0.12) | <0.001 |
| Sneezing | −0.41 (−0.53, −0.29) | <0.001 |
| Instantaneous | | |
| Rhinorrhea | −0.29 (−0.39, −0.18) | <0.001 |
| Nasal congestion | −0.19 (−0.29, −0.09) | <0.001 |
| Nasal itching | −0.21 (−0.32, −0.10) | <0.001 |
| Sneezing | −0.29 (−0.41, −0.18) | <0.001 |

The combination of mometasone fuorate and olopatadine hydrochloride, when administered twice daily (TP-1) also exhibited a faster (rapid) onset of action (an onset of action within 15 minutes), as measured by iTNSS, when compared to olopatadine hydrochloride monotherapy or mometasone fuorate monotherapy.

All TEAEs were mild to moderate. Dysgeusia (3.8%) nasal discomfort (1%) and urinary tract infection (1%) were reported adverse events for the combination of mometasone fuorate and olopatadine hydrochloride administered twice daily (BID).

Example 7

Phase III Clinical Study of Fixed Dose Combination of Mometasone and Olopatadine Nasal Spray in Human Patients The study is a double-blind, randomized, parallel-group, comparative study to evaluate the long-term safety, efficacy, and tolerability of a fixed dose combination of mometasone furoate and olopatadine hydrochloride nasal spray compared with two placebo nasal sprays, in subjects (12 years of age and older) with perennial allergic rhinitis (PAR).

Study Objectives

To compare the long-term safety and tolerability of mometasone furoate and olopatadine hydrochloride nasal spray twice daily with two placebo nasal sprays at the same dose in the same vehicle over 52 weeks of study treatment in subjects with PAR.

A secondary objective is to evaluate the long-term efficacy of a fixed dose combination of mometasone furoate and olopatadine hydrochloride nasal spray compared with a placebo nasal spray formulations (pH=3.7) in subjects with PAR.

Key Subject Selection Criteria:
- Male and non-pregnant females aged ≥12 years.
- A history of PAR for a minimum of 2 years and a positive skin prick test to at least 1 relevant allergen.
- An AM subject-reported Reflective Total Nasal Symptom Score (rTNSS)≥5 out of a possible 12 and a congestion score ≥2 for the morning (AM) assessment at the Screening Visit (Visit 1).
- At the end of the placebo run-in period, to be eligible for randomization, the subject had not experienced an AE that would result in not meeting the Screening inclusion criteria.
- Minimum AM subject-reported rTNSS of an average of 5 (out of a possible 12) during the last 4 days of the run-in period (last 4 consecutive AM assessments from the Day 3 AM assessment to the AM assessment on the day of randomization)
- Had an AM subject-reported reflective nasal congestion score of an average 2 or greater during the last 4 days of the run-in period (last 4 consecutive AM assessments from the Day 3 AM assessment to the AM assessment on the day of randomization)

Study Design:

A total of 601 randomized subjects were enrolled in the study. Subjects were randomized to treatment in a 4:1:1 ratio to 3 treatment groups, at multiple site. The treatment groups are provided in Table I below.

TABLE I

Investigational products and their administration

| Code | Investigational product(s) | Administration |
|---|---|---|
| TP-1 | Olopatadine hydrochloride + mometasone furoate (665 µg + 25 µg) nasal spray | Twice daily (BID) in morning and evening |
| Pbo-1 | Placebo nasal spray, pH 3.7 | Placebo - Twice daily (BID) in morning and evening |
| Pbo-2 | Placebo nasal spray, pH 7.0 | Placebo - Twice daily (BID) in morning and evening |

This study consisted of twelve visits to the study site. After the initial screening visit (Visit 1), subjects who met all study selection criteria underwent a single-blind placebo run-in period for 7-10 days. Following the completion of the run-in period, eligible subjects meeting the randomization criteria were enrolled and randomized to one of the three treatment arms. Randomized subjects underwent a 52 week treatment period as per the protocol to assess the efficacy and safety of the assigned treatment.

Key Evaluation Criteria (Clinical Endpoints):

Primary Endpoints
- Proportion of subjects with treatment-emergent adverse events (TEAEs).
- Proportion of subjects with treatment-related TEAEs.
- Incidence, type, and severity of the TEAEs after 30 weeks of study treatment.
- Incidence, type, and severity of the TEAEs after 52 weeks of study treatment.
- Clinical laboratory assessments (hematology, serum biochemistry, and urinalysis) at baseline, Week 30, and Week 52.
- Vital signs, physical examinations (PE), and focused ears, nose, and throat (ENT) and eye examinations at baseline, Week 30, and Week 52.

Secondary Endpoints

Efficacy Endpoints
- Change from baseline in the average AM subject-reported rTNSS over the first 6, 30, and 52 weeks of treatment.
- Change from baseline in the average AM subject-reported instantaneous Total Nasal Symptom Score (iTNSS) over the first 6, 30, and 52 weeks of treatment.
- Change from baseline in the overall Rhinoconjunctivitis Quality of Life Questionnaire—Standardized Activities (RQLQ(S)) score at Weeks 6, 30, and 52 for the Full Analysis Set (FAS).

Other Efficacy Endpoints

Other endpoints included other assessments of AM subject-reported individual nasal symptoms, AM subject-reported rTNSS and iTNSS from baseline to the end of each treatment week, Physician-assessed Nasal Symptom Score and physician-assessed individual nasal symptoms, individual domains of the RQLQ for the FAS population, and change from baseline in the Rhinitis Control Assessment Test and individual domains of Rhinitis Control Assessment Test.

Data Sets Analyzed

The Full Analysis Set (FAS) consisted of all subjects who were randomized and received at least one dose of investigational product and had at least one post-baseline efficacy assessment. This was the primary analysis set for efficacy analyses.

The Per Protocol Set (PPS) consisted of the subset of the FAS who did not meet criteria for PPS exclusion. The PPS was a secondary analysis set for the efficacy analyses (except for RQLQ(S)).

The Safety Analysis Set (SAS) consisted of all subjects who took at least one dose of study medication following randomization, and was used for all safety analyses.

The RQLQ(S) Analysis Set consisted of all English-speaking subjects ≥18 years old with impaired quality of life at baseline as defined by RQLQ(S) Score at the Randomization Visit (Visit 2) of 3.0 or greater Efficacy Analysis Efficacy analysis was conducted on the FAS and PPS.

Change from baseline in average AM rTNSS and iTNSS over the first 6, 30, and 52 weeks of treatment was analyzed using an analysis of covariance (ANCOVA) model adjusting for study treatment group, site, and baseline (defined as the average of the last 4 consecutive AM assessments during the last 4 days of the run-in period from the Day −3 AM assessment to the AM assessment on the day of randomization). Least squares means (LSMs) of the treatment differences and associated 95% confidence intervals (95% CIs) and p-values were presented.

Changes from baseline in rTNSS and iTNSS at the end of each week of treatment and changes from baseline in individual nasal symptom scores over the first 6, 30, and 52 weeks (and at the end of each treatment week) of the treatment period were analyzed in a similar manner as described above.

Changes from baseline in RQLQ(S) at Weeks 6, 30, and 52 were analyzed for the FAS and the RQLQ(S) Analysis Set using ANCOVA models adjusting for study treatment group, site, and baseline RQLQ(S) (linear, continuous covariate). At each time-point, only completers of the respective visit were analyzed.

The analyses of RCAT results were similar to the RQLQ (S) analyses except that it was performed only for the FAS.

Safety Analysis

Adverse events occurring after the first dose of randomized study medication were defined as TEAEs.

The safety endpoints related to AEs were:

Proportion of subjects with TEAEs.

Proportion of subjects with treatment-related TEAEs.

Incidence, type, and severity of the TEAEs after 30 weeks of study treatment.

Incidence, type, and severity of the TEAEs after 52 weeks of study treatment.

Results

Safety Analysis

The table below summarizes the safety analysis for the three treatment groups over the 52 week administration period.

| Safety Analysis | TP-1 | Pbo-1 (pH = 3.7) | Pbo-2 (pH = 7.0) |
| --- | --- | --- | --- |
| Subjects with a least one TEAE: n (%) | 203 (52%) | 41 (41%) | 54 (54%) |
| TEAEs resulting in discontinuation: n (%) | 15 (3.8%) | 2 (2.0%) | 3 (3.0%) |
| SAEs (all considered not related) | 7 (1.5%) | 2 (2.0%) | 3 (1.5%) |

As can be seen, there was no meaningful differences between the three treatment groups. The majority of TEAEs were mild to moderate severity and considered "not related" by the investigator. The TP-1 treatment was safe and well tolerated, with safety profiles consistent with those expected for the individual monotherapy components. No deaths were reported during the study.

Efficacy Analysis

The table below summarizes the results for the efficacy endpoint: nasal symptoms average AM Reflective Total Nasal Symptoms (rTNSS, last 12 hours) (full set analysis, FAS).

| | TP-1 vs. Pbo-1 (pH = 3.7) | | |
| --- | --- | --- | --- |
| | 6 weeks | 30 weeks | 52 Weeks |
| N (TP-1/Pbo-1) | 319/99 | 391/99 | 391/99 |
| Treatment Difference | −0.81 | −0.96 | −0.91 |
| 95% CI | −1.29, −0.32 | −1.41, −0.50 | −1.35, −0.47 |
| p-Value | 0.0012* | <0.0001* | <0.0001* |

*Statistically Significant

As can be seen, TP-1 demonstrated a statistically significant and meaningful improvement in rTNSS versus Pbo-1 (pH=3.7) over the first 6, 30 and 52 weeks of the study.

The table below summarizes the results for the efficacy endpoint: nasal symptoms average AM Instantaneous Total Nasal Symptoms (iTNSS, last 12 hours) (full set analysis, FAS).

| | TP-1 vs. Pbo-1 (pH = 3.7) | | |
| --- | --- | --- | --- |
| | 6 weeks | 30 weeks | 52 Weeks |
| N (TP-1/Pbo-1) | 319/99 | 391/99 | 391/99 |
| Treatment Difference | −0.66 | −0.83 | −0.75 |
| 95% CI | −1.12, −0.20 | −1.26, −0.39 | −1.17, −0.33 |
| p-Value | 0.0053* | 0.0002* | 0.0005* |

*Statistically Significant

As can be seen, TP-1 demonstrated a statistically significant and meaningful improvement in iTNSS versus Pbo-1 (pH=3.7) over the first 6, 30 and 52 weeks of the study.

The table below summarizes the results for the Quality of Life Endpoint: RQLQ (S) (full set analysis, FAS).

| TP-1 vs. Pbo-1 (pH = 3.7) | | | |
| --- | --- | --- | --- |
| | 6 weeks | 30 weeks | 52 Weeks |
| N (TP-1/Pbo-1) | 371/95 | 322/84 | 286/72 |
| Treatment Difference | −0.42 | −0.33 | −0.04 |
| 95% Cl | −0.70, −0.14 | −0.60, −0.05 | −0.34, −0.26 |
| p-Value | 0.0035* | 0.0186* | 0.7902 |

*Statistically Significant

As can be seen, TP-1 demonstrated a statistically significant and meaningful improvement in RQLQ (S) versus Pbo-1 (pH=3.7) over the first 6 and 30 weeks of the study.

Examples 8 and 9

Suspension Compositions Containing Mometasone Furoate, Olopatadine HCl and Carboxymethylcellulose Sodium

| SN | Ingredient | Example 8 (% w/w) | Example 9 (% w/w) |
| --- | --- | --- | --- |
| 1 | Mometasone Furoate monohydrate Eq. to Mometasone furoate | 0.050 | 0.025 |
| 2 | Olopatadine Hydrochloride | 0.665 | 0.665 |
| 3 | Avicel RC 591 (Microcrystalline Cellulose and Carboxymethylcellulose Sodium) | 1.200 | 1.200 |
| 4 | Benzalkonium chloride (50% solution) | 0.040 | 0.040 |
| 5 | Carboxymethylcellulose Sodium (Cekol 2000 P) | 0.500 | 0.500 |
| 6 | Sodium chloride | 0.410 | 0.410 |
| 7 | Edetate disodium | 0.010 | 0.010 |
| 8 | Dibasic sodium phosphate heptahydrate | 0.940 | 0.940 |
| 9 | Polysorbate 80 | 0.010 | 0.010 |
| 10 | Sodium Hydroxide | Q.S. | Q.S. |
| 11 | Hydrochloric acid | Q.S. | Q.S. |
| 12 | Water for injection | Q.S. | Q.S. |
| Observations | | | |
| | Physical observation on standing for 24 hours | No phase separation observed | No phase separation observed |
| | Mean Particle size by microscopy | Below 15 µm. | Below 15 µm. |

Manufacturing Procedure:

1. Avicel RC-591 was added in water for injection with homogenization and allowed to hydrate.
2. Carboxymethylcellulose Sodium was dispersed in water for injection and added to step-1.
3. Dibasic sodium phosphate heptahydrate, Sodium chloride, Edetate disodium and Olopatadine were dissolved in water. The pH was adjusted to 2.8-3.2 with Hydrochloric acid.
4. Step-3 was added to Step-1 with homogenization.
5. Polysorbate 80 was dissolved in water for injection. Mometasone Furoate monohydrate was added and stirred to form slurry.
6. Step-5 was added to Step-4 with homogenization.
7. Benzalkonium chloride was dissolved in water for injection.
8. Step-7 was added to Step-6 with homogenization.
9. The pH was checked and adjusted to 3.5-3.9 with HCl and the total weight was adjusted with Water for injection. The osmolality of the composition was about 250-350 mOsm/kg.

The composition was subjected to stability studies at different conditions. The results of the same are as follows:

Container details: Sprayer containing HDPE bottle crimped with pump and fitted with an actuator and can.

| Stability Study Data | | | | | | |
| --- | --- | --- | --- | --- | --- | --- |
| | Initial | | 3 months | | 6 months | |
| Test | Ex. 8 | Ex. 9 | Ex. 8 | Ex. 9 | Ex. 8 | Ex. 9 |
| Stability condition (25° C. ± 2° C. & 60% RH ± 5% RH) | | | | | | |
| pH | | 3.61 | 3.69 | 3.73 | 3.78 | 3.81 |
| Osmolality (mOsm)* | 310 | 308 | 299 | 298 | 302 | 311 |
| Viscosity (cps)** | | 32.5 | 42.5 | 42.3 | 40.6 | 40.9 |
| Weight per ml (g/ml) | | 1.01 | 1.021 | 1.024 | 1.029 | 1.019 |
| Assay of mometasone furoate (% w/w) | 101 | 102.4 | 99.1 | 99.3 | 98.2 | 97.2 |
| Assay of olopatadine hydrochloride (% w/w) | 98.2 | 99.9 | 97.3 | 99.1 | 97.8 | 97.9 |
| Related substances for mometasone furoate | | | | | | |
| Impurity DMCF (%) | 0.02 | 0.03 | 0.09 | 0.10 | 0.14 | 0.17 |
| Any other impurity (%) | 0.04 | | 0.04 | | 0.03 | |
| Total impurities (%) | 0.09 | | 0.23 | 0.29 | 0.31 | 0.34 |
| Related substances for olopatadine hydrochloride | | | | | | |
| Olopatadine E-isomer (%) | 0.08 | 0.07 | 0.09 | | 0.09 | |
| Any other impurity (%) | 0.03 | 0.04 | 0.09 | 0.12 | 0.11 | 0.11 |
| Total impurities (%) | 0.15 | 0.16 | 0.20 | 0.25 | 0.37 | 0.38 |
| Spray Pattern (at 6 cm) | | | | | | |
| Major Axis (mm) | 52 | | 60 | 63 | 59 | 61 |
| Minor Axis (mm) | 43 | 47 | 49 | 53 | 49 | 51 |
| Ellipticity | 1.2 | 1.1 | 1.2 | 1.2 | 1.2 | 1.2 |

Stability Study Data

|  | Initial | | 3 months | | 6 months | |
|---|---|---|---|---|---|---|
| Test | Ex. 8 | Ex. 9 | Ex. 8 | Ex. 9 | Ex. 8 | Ex. 9 |
| Droplet size distribution (at 6 cm) | | | | | | |
| $D_{10}$ (μm) | 18.91 | 19.45 | 19.26 | 19.70 | 19.33 | 18.88 |
| $D_{50}$ (μm) | 36.39 | 37.61 | 35.96 | 37.34 | 39.28 | 37.85 |
| $D_{90}$ (μm) | 72.46 | 76.44 | 70.29 | 75.78 | 85.42 | 72.07 |
| SPAN | 1.47 | 1.51 | 1.42 | 1.5 | 1.67 | 1.46 |
| Stability condition (40° C. ± 2° C. & 75% RH ± 5% RH) | | | | | | |
| pH |  | 3.61 | 3.68 | 3.72 | 3.59 | 3.68 |
| Osmolality (mOsm) | 310 | 308 | 298 | 306 | 305 | 299 |
| Viscosity (cps) |  | 32.5 | 45.2 | 42.6 | 41.8 | 41.5 |
| Weight per ml (g/ml) |  | 1.01 | 1.023 | 1.019 | 1.026 | 1.025 |
| Assay of mometasone furoate (%) | 101 | 102.4 | 99.8 | 100.4 | 98.3 | 98.4 |
| Assay of oloptadine hydrochloride (%) | 98.2 | 99.9 | 99.3 | 102.5 | 98.7 | 99.7 |
| Related substances for mometasone furoate | | | | | | |
| Impurity DMCF (%) | 0.02 | 0.03 | 0.14 | 0.20 | 0.25 | 0.25 |
| Any other impurity (%) | 0.04 | 0.04 | 0.04 | 0.03 | 0.03 | 0.04 |
| Total impurities (%) |  | 0.09 | 0.25 | 0.39 | 0.40 | 0.46 |
| Related substances for olopatadine hydrochloride | | | | | | |
| Olopatadine E-isomer (%) |  | 0.08 | 0.07 | 0.08 | 0.08 | 0.09 |
| Any other impurity (%) | 0.03 | 0.04 | 0.21 | 0.18 | 0.31 | 0.30 |
| Total impurities (%) | 0.15 | 0.16 | 0.32 | 0.36 | 0.68 | 0.64 |
| Spray Pattern (at 6 cm) | | | | | | |
| Major Axis (mm) | 52 | 52 | 61 | 58 | 58 | 58 |
| Minor Axis (mm) | 43 | 47 | 50 | 49 | 48 | 49 |
| Ellipticity | 1.2 | 1.1 | 1.2 | 1.2 | 1.2 | 1.2 |
| Droplet size distribution (at 6 cm) | | | | | | |
| $D_{10}$ (μm) | 18.91 | 19.45 | 19.49 | 19.27 | 18.05 | 18.09 |
| $D_{50}$ (μm) | 36.39 | 37.61 | 35.29 | 34.68 | 36.19 | 36.12 |
| $D_{90}$ (μm) | 72.46 | 76.44 | 64.66 | 63.49 | 71.89 | 70.06 |
| SPAN | 1.47 | 1.51 | 1.28 | 1.27 | 1.50 | 1.44 |

*Determined by Advanced Instruments Osmometer (Model 3250).
**Determined by Brookfield viscometer.

Examples 10 and 11

Suspension Compositions Containing Mometasone Furoate, Olopatadine HCl and Xanthan Gum

| SN | Ingredient | Example 10 (% w/w) | Example 11 (% w/w) |
|---|---|---|---|
| 1 | Mometasone Furoate monohydrate Eq. to Mometasone furoate | 0.050 | 0.025 |
| 2 | Olopatadine HCl | 0.665 | 0.665 |
| 3 | Avicel RC 591 (Microcrystalline Cellulose and Carboxymethylcellulose Sodium) | 1.000 | 1.000 |
| 4 | Benzalkonium chloride (50% solution) | 0.040 | 0.040 |
| 5 | Xantural 75 (Xanthan Gum) | 0.300 | 0.300 |
| 6 | Sodium chloride | 0.410 | 0.410 |
| 7 | Edetate disodium | 0.010 | 0.010 |
| 8 | Dibasic sodium phosphate heptahydrate | 0.940 | 0.940 |
| 9 | Polysorbate 80 | 0.010 | 0.010 |
| 10 | Sodium Hydroxide | Q.S. | Q.S. |
| 11 | Hydrochloric acid | Q.S. | Q.S. |
| 12 | Water for injection | Q.S. | Q.S. |
| Observations | | | |
| | Physical observation on standing for 24 hours | No phase separation observed | No phase separation observed |
| | Mean Particle size by microscopy | Below 15 μm. | Below 15 μm. |

Manufacturing Procedure:

1. Avicel RC-591 was added in Water for injection with homogenization and allowed to hydrate.

2. Xanthan gum was dispersed in Water for injection and added to step-1.

3. Dibasic sodium phosphate heptahydrate, Sodium chloride, Edetate disodium and Olopatadine were dissolved in water. The pH was adjusted to 2.8-3.2 with Hydrochloric acid.

4. Step-3 was added to Step-1.

5. Polysorbate 80 was dissolved in water for injection. Mometasone Furoate monohydrate was added to it and stirred to form slurry.

6. Step-5 was added to Step-4 with homogenization.

7. Benzalkonium chloride was dissolved in water for injection.

8. Step-7 was added to Step-6 with homogenization.
9. The pH was checked and adjusted to 3.5-3.9 with HCl and the weight was adjusted with water for injection. The osmolality of the composition was about 250-350 mOsm/kg.

The composition was subjected to stability studies at different conditions. The results of the same are as follows:

Container details: Sprayer containing HDPE bottle crimped with pump and fitted with a actuator and cap

| | Stability Study Results | | | | | |
|---|---|---|---|---|---|---|
| | Initial | | 3 months | | 6 months | |
| Test | Ex. 10 | Ex. 11 | Ex. 10 | Ex. 11 | Ex. 10 | Ex. 11 |
| Stability condition (25° C. ± 2° C. & 60% RH ± 5% RH) | | | | | | |
| pH | 3.65 | 3.67 | 3.78 | 3.65 | 3.70 | 3.62 |
| Osmolality (mOsm) | 307 | 312 | 302 | 316 | 308 | 308 |
| Viscosity (cps) | 124.2 | 129.1 | 127.9 | 129.9 | 126.2 | 126.8 |
| Weight per ml (g/ml) | 1.015 | 1.022 | 1.02 | 1.023 | 1.02 | 1.019 |
| Assay of mometasone furoate (%) | 99.9 | 102.8 | 102.2 | 99.0 | 98.7 | 100.4 |
| Assay of olopatadine hydrochloride (%) | 99.2 | 100.7 | 99.7 | 99.7 | 99.4 | 99.6 |
| Related substances for mometasone furoate | | | | | | |
| Impurity DMCF (%) | 0.02 | 0.02 | 0.04 | 0.05 | 0.03 | 0.05 |
| Any other impurity (%) | 0.03 | | 0.04 | | 0.03 | 0.04 |
| Total impurities (%) | 0.11 | 0.10 | 0.15 | 0.16 | 0.12 | 0.16 |
| Related substances for olopatadine hydrochloride | | | | | | |
| Olopatadine E-isomer (%) | 0.08 | 0.07 | 0.09 | 0.11 | 0.11 | 0.10 |
| Any other impurity (%) | 0.03 | 0.04 | 0.05 | 0.05 | 0.08 | 0.08 |
| Total impurities (%) | 0.18 | 0.15 | 0.24 | 0.20 | 0.33 | 0.33 |
| Spray Pattern (at 6 cm) | | | | | | |
| Major Axis (mm) | 46 | | 59 | 59 | 56 | 54 |
| Minor Axis (mm) | 38 | | 47 | 44 | 35 | 43 |
| Ellipticity | 1.2 | | 1.3 | 1.4 | 1.6 | 1.3 |
| Droplet size distribution (at 6 cm) | | | | | | |
| $D_{10}$ (μm) | 21.58 | 21.03 | 20.95 | 20.27 | 18.73 | 18.34 |
| $D_{50}$ (μm) | 40.44 | 39.79 | 37.86 | 37.93 | 36.66 | 36.16 |
| $D_{90}$ (μm) | 78.25 | 77.55 | 74.07 | 74.93 | 70.63 | 70.99 |
| SPAN | 1.40 | 1.42 | 1.40 | 1.44 | 1.41 | 1.45 |
| Stability condition (40° C. ± 2° C. & 75% RH ± 5% RH) | | | | | | |
| pH | 3.65 | 3.67 | 3.70 | 3.77 | 3.78 | 3.65 |
| Osmolality (mOsm) | 307 | 312 | 309 | 305 | 302 | 316 |
| Viscosity (cps) | 124.2 | 129.1 | 129.6 | 124.3 | 127.9 | 129.9 |
| Weight per ml (g/ml) | 1.015 | 1.022 | 1.017 | 1.027 | 1.022 | 1.020 |
| Assay of mometasone furoate (%) | 99.9 | 102.8 | 101.7 | 100.6 | 99.6 | 98.9 |
| Assay of oloptadine hydrochloride (%) | 99.2 | 100.7 | 99.9 | 99.4 | 99.7 | 99.9 |
| Related substances for mometasone furoate | | | | | | |
| Impurity DMCF (%) | 0.02 | 0.02 | 0.10 | 0.12 | 0.10 | 0.12 |
| Any other impurity (%) | 0.03 | 0.03 | 0.02 | 0.03 | 0.05 | 0.03 |
| Total impurities (%) | 0.11 | 0.10 | 0.20 | 0.22 | 0.18 | 0.21 |
| Related substances for olopatadine hydrochloride | | | | | | |
| Olopatadine E-isomer (%) | 0.08 | 0.07 | 0.12 | 0.13 | 0.11 | 0.11 |
| Any other impurity (%) | 0.03 | 0.04 | 0.06 | 0.06 | 0.12 | 0.12 |
| Total impurities (%) | 0.18 | 0.15 | 0.26 | 0.26 | 0.41 | 0.40 |
| Spray Pattern (at 6 cm) | | | | | | |
| Major Axis (mm) | 46 | 46 | 56 | 58 | 54 | 55 |
| Minor Axis (mm) | 38 | 38 | 45 | 49 | 34 | 43 |
| Ellipticity | 1.2 | 1.2 | 1.3 | 1.2 | 1.6 | 1.3 |
| Droplet size distribution (at 6 cm) | | | | | | |
| $D_{10}$ (μm) | 21.58 | 21.03 | 20.67 | 23.16 | 19.13 | 19.16 |
| $D_{50}$ (μm) | 40.44 | 39.79 | 38.06 | 39.08 | 37.34 | 37.26 |
| $D_{90}$ (μm) | 78.25 | 77.55 | 75.63 | 69.37 | 72.36 | 72.49 |
| SPAN | 1.40 | 1.42 | 1.44 | 1.19 | 1.42 | 1.43 |

Comparative Examples A and B

Suspension Composition Containing Mometasone Furoate, and Olopatadine HCl

| SN | Ingredient | Example (% w/w) A | B |
|---|---|---|---|
| 1 | Mometasone Furoate monohydrate Eq. to Mometasone furoate | 0.050 | 0.050 |
| 2 | Olopatadine HCl | 0.665 | 0.665 |
| 3 | Avicel RC 591 (Microcrystalline Cellulose and Carboxymethyl cellulose Sodium) | 1.00 | 1.00 |
| 4 | Benzalkonium chloride (50% solution) | 0.040 | 0.040 |
| 5 | Carboxymethylcellulose Sodium (Cekol 2000 P) | 0.00 | 0.150 |
| 6 | Sodium chloride | 0.410 | 0.410 |
| 7 | Edetate disodium | 0.010 | 0.010 |
| 8 | Dibasic sodium phosphate heptahydrate | 0.940 | 0.940 |
| 9 | Polysorbate 80 | 0.010 | 0.010 |
| 10 | Sodium Hydroxide | Q.S. | Q.S. |
| 11 | Hydrochloric acid | Q.S. | Q.S. |
| 12 | Water for injection | Q.S. | Q.S. |
| | Observations | | |
| | pH | 3.7 | 3.7 |
| | Physical observation on standing for 24 hours | Phase separation observed | Phase separation observed |

Manufacturing Procedure:

The manufacturing procedure as mentioned in Example 8 was followed.

Comparative Examples C and D

Suspension Composition Containing Mometasone Furoate and Olopatadine HCl

| SN | Ingredient | Example (% w/w) C | D |
|---|---|---|---|
| 1 | Mometasone Furoate monohydrate Eq. to Mometasone furoate | 0.050 | 0.050 |
| 2 | Olopatadine HCl | 0.665 | 0.665 |
| 3 | Avicel RC 591 (Microcrystalline Cellulose and Carboxymethyl cellulose Sodium) | 1.000 | 1.000 |
| 4 | Benzalkonium chloride (50% solution) | 0.040 | 0.040 |
| 5 | Xantural 75 (Xanthan Gum) | 0.00 | 0.20 |
| 6 | Sodium chloride | 0.410 | 0.410 |
| 7 | Edetate disodium | 0.010 | 0.010 |
| 8 | Dibasic sodium phosphate heptahydrate | 0.940 | 0.940 |
| 9 | Polysorbate 80 | 0.010 | 0.010 |
| 10 | Sodium Hydroxide | Q.S. | Q.S. |
| 11 | Hydrochloric acid | Q.S. | Q.S. |
| 12 | Water for injection | Q.S. | Q.S. |
| | Observations | | |
| | pH | 3.73 | 3.70 |
| | Physical observation on standing for 24 hours | Phase separation observed | Phase separation observed |

Manufacturing Procedure:

The manufacturing procedure as mentioned in Example 10 was followed.

Example 12

Pharmacokinetics of Olopatadine in a Fixed Dose Combination of Mometasone Furoate and Olopatadine Hydrochloride Nasal Spray The pharmacokinetics of olopatadine in a fixed dose combination of mometasone furoate and olopatadine hydrochloride nasal spray was evaluated in a clinical trial. The clinical trial was a randomized, single-center, single-dose, open-label, three-period, six-sequence, cross-over study to evaluate three treatments administered as a nasal spray. The three treatments included a combination of mometasone furoate and olopatadine hydrochloride nasal spray, olopatadine hydrochloride nasal spray and PATANASE® nasal spray.

Subjects were randomized to 1 of 6 treatment sequences in a 1:1:1:1:1:1 ratio with all subjects receiving single doses of a fixed dose combination of mometasone furoate and olopatadine hydrochloride nasal spray, olopatadine hydrochloride nasal spray, and PATANASE® nasal spray. The study consisted of a screening visit, 3 single-dose treatment periods with washout periods of 7 to 14 days between dosing in each treatment period, an early withdrawal visit if applicable, and a follow-up telephone call (or visit) 1 to 7 days after completing the third treatment period.

A total of 30 subjects were randomized to 1 of 6 treatment sequences and received at least 1 dose of study drug. All 30 subjects were included in the safety analysis set and the pharmacokinetic subset. All but 2 subjects completed the study per protocol. The safety analysis set consisted of 30 subjects: 29, 29, and 30 subjects in the safety analysis set received a single dose of the fixed dose combination of mometasone furoate and olopatadine hydrochloride nasal spray, olopatadine hydrochloride nasal spray, and PATANASE® nasal spray, respectively. The pharmacokinetic subset consisted of 30 subjects: 29, 29, and 30 subjects in the pharmacokinetic subset received a single dose of the fixed dose combination of mometasone furoate and olopatadine hydrochloride nasal spray, olopatadine hydrochloride nasal spray, and PATANASE® nasal spray, respectively.

Quantifiable concentrations of olopatadine were observed until the last time point (48 hours). All 3 treatments were well tolerated. No subject died or reported a serious adverse event; and only one subject discontinued due to a treatment-emergent adverse event (mild oropharyngeal pain) in this study. Treatment-emergent adverse events and treatment-related treatment emergent adverse events were evenly distributed across the 3 treatments. All treatment-emergent adverse events were mild. There was no clinically significant effect of any of the treatments on laboratory values, vital sign measurements, or ECG parameters.

Example 13

Pharmacokinetics of Mometasone Furoate in a Fixed Dose Combination of Mometasone Furoate and Olopatadine Hydrochloride Nasal Spray The pharmacokinetics of mometasone furoate in a fixed dose combination of mometasone furoate and olopatadine hydrochloride nasal spray was evaluated in a clinical trial. The clinical trial was a randomized, single-center, single-dose, open-label, three-period, six-sequence, cross-over study to evaluate three treatments administered by nasal spray. The three treatments included a combination of mometasone furoate and olopatadine hydrochloride nasal spray, mometasone furoate nasal spray and Nasonex® nasal spray.

Subjects were randomized to 1 of 6 treatment sequences in a 1:1:1:1:1:1 ratio with all subjects receiving single doses of a fixed dose combination of mometasone furoate and olopatadine hydrochloride nasal spray, mometasone furoate nasal spray and Nasonex® nasal spray. The study consisted of a screening visit, 3 single-dose treatment periods with washout periods of 7 to 14 days between dosing in each treatment period, an early withdrawal visit if applicable, and a follow-up telephone call (or visit) 1 to 7 days after completing the third treatment period.

A total of 30 subjects were randomized to 1 of 6 treatment sequences and received at least 1 dose of study drug. All 30 subjects were included in the safety analysis set and the pharmacokinetic subset. All but 2 subjects completed the study per protocol. The safety analysis set consisted of 30 subjects: 29, 29, and 30 subjects in the safety analysis set received a single dose of the fixed dose combination of mometasone furoate and olopatadine hydrochloride nasal spray, mometasone furoate nasal spray and Nasonex® nasal spray, respectively. The pharmacokinetic subset consisted of 30 subjects: 29, 29, and 30 subjects in the pharmacokinetic subset received a single dose of the fixed dose combination of mometasone furoate and olopatadine hydrochloride nasal spray, mometasone furoate nasal spray and Nasonex® nasal spray respectively.

Quantifiable concentrations of mometasone furoate were observed until the last time point (72 hours). All 3 treatments were well tolerated. No subject died or reported a serious adverse event, or discontinued due to a treatment-emergent adverse event in this study. Treatment-emergent adverse events were evenly distributed across the 3 treatments. All treatment-emergent adverse events were mild. There was no clinically significant effect of any of the treatments on laboratory values, vital sign measurements, or ECG parameters.

Example 14

Phase III Clinical Study of Fixed Dose Combination of Mometasone and Olopatadine Nasal Spray in Pediatric Patients This study is a double blind, randomized, parallel-group, 12-week study to evaluate the efficacy, safety, and tolerability of a fixed dose combination of mometasone furoate and olopatadine hydrochloride nasal spray compared with a placebo nasal spray in pediatric subjects (aged 2 to under 12 years) with perennial seasonal allergic rhinitis (PAR).

Study Objectives

To compare the efficacy of mometasone furoate and olopatadine hydrochloride nasal spray (administered as 1 spray per nostril twice daily) with a placebo nasal spray for treatment in pediatric subjects (aged ≥2 to <12 years) with PAR.

A secondary objective is to compare the safety and tolerability of mometasone furoate and olopatadine hydrochloride nasal spray with a placebo nasal spray over 12 weeks of study treatment.

Key Subject Selection Criteria

Male or non-pregnant female subjects aged ≥2 to <12 years, as of the Screening Visit (Visit 1).

Documented clinical history of PAR (≥12 months for subjects aged ≥6 to <12 years, ≥6 months for subjects aged ≥2 to <6 years preceding the Screening Visit [Visit 1]) with exacerbations (clinical evidence of active symptoms). In the judgment of the Investigator, the PAR must have been of sufficient severity to have required treatment (either continuous or intermittent) in the past and is expected to require treatment for the study duration.

Documented positive skin prick test (wheal diameter at least 3 mm greater than negative control wheal) to at

| Therapy | Pharmacokinetic Parameters | | | |
|---|---|---|---|---|
| | $AUC_{(0-t)}$ | $AUC_{(0-infinity)}$ | $C_{max}$ | $T_{max}$ |
| Olopatadine in fixed dose combination of mometasone furoate and olopatadine hydrochloride nasal spray | 70.95 ng · h/mL | 83.26 ng · h/mL | 17.27 ng/mL | 1.00 hr |
| Mometasone furoate in fixed dose combination of mometasone furoate and olopatadine hydrochloride nasal spray | 84.97 pg · h/mL | 103.77 pg · h/mL | 10.81 pg/mL | 1.00 hr |
| Relative Bioavailability of fixed dose combination of mometasone furoate and olopatadine hydrochloride nasal spray versus: | | | | |
| Patanase ® (Geometric mean ratio %) | 87.87 | 93.80 | 84.68 | — |
| Nasonex ® (Geometric mean ratio %) | 109.92 | 115.14 | 141.84 | — |
| olopatadine hydrochloride (Geometric mean ratio %) | 86.92 | 92.83 | 86.63 | — |
| mometasone furoate (Geometric mean ratio %) | 118.36 | 118.50 | 113.83 | — | least one allergen known to induce PAR. Documentation of a positive result within 12 months prior to the Screening Visit (Visit 1) is acceptable. Positive allergen test for the subject that must be consistent with the medical history of PAR. Additionally the subject is expected to be exposed to the PAR allergen that he or she tested positive for via the skin prick test for the entire duration of the study.

A 12-hour rTNSS value of ≥6 (out of a possible 12) for the AM assessment at the Screening Visit (Visit 1).

Study Design

A total of approximately 540 subjects (≥2 to <12 years) will be randomized in the study in a 2:1 ratio for a fixed dose combination of mometasone furoate and olopatadine hydrochloride nasal spray (360 subjects) versus placebo nasal spray (180 subjects).

The study will be 12 weeks in duration. The subject participation may extend up to 13 to 14 weeks consisting of up to 7 to 10 days of a screening/placebo run-in period and 12 weeks of treatment period with allowable window periods for the study visits. The treatment groups are provided in the table below.

Investigational Products and their Administration

| Investigational product(s) | Administration |
| --- | --- |
| Olopatadine hydrochloride + mometasone furoate (665 µg + 25 µg) nasal spray* | 1 spray per nostril, twice daily (BID) in morning and evening |
| Placebo nasal spray | Placebo - 1 spray per nostril twice daily (BID) in morning and evening |

*Each spray provides 665 µg olopatadine hydrochloride and 25 µg mometasone furoate.

Primary Endpoint:
　Change from baseline in average AM and PM subject-reported 12-hour reflective Total Nasal Symptom Score (rTNSS) over the first 4 weeks of treatment for subjects aged ≥6 to <12 years.
Secondary Endpoint(s):
　Change from baseline in average AM and PM subject-reported 12-hour instantaneous Total Nasal Symptom Score (iTNSS) over the first 4 weeks of treatment for subjects ≥6 to <12 years of age.
　Change from baseline in average AM and PM subject-reported 12-hour rTNSS over the first 4 weeks of treatment for subjects ≥2 to <12 years of age.
　Change from baseline in average AM and PM subject-reported 12-hour iTNSS over the first 4 weeks of treatment for subjects ≥2 to <12 years of age.
　Change from baseline in the overall Pediatric Rhinoconjunctivitis Quality of Life Questionnaire (PRQLQ) score at Week 4 between treatment groups.
Other Endpoint(s):
Nasal Symptoms:
　TNSS—First 4 Weeks, Subjects Aged ≥6 to <12 Years:
　Change from baseline in AM subject-reported rTNSS over the first 4 weeks of treatment.
　Change from baseline in PM subject-reported rTNSS over the first 4 weeks of treatment.
　Change from baseline in AM subject-reported iTNSS over the first 4 weeks of treatment.
　Change from baseline in PM subject-reported iTNSS over the first 4 weeks of treatment.
　Change from baseline in subject-reported reflective individual nasal symptoms over the first 4 weeks of treatment period (AM, PM and average of AM and PM).
　Change from baseline in subject-reported instantaneous individual nasal symptoms over the first 4 weeks of treatment period (AM, PM and average of AM and PM).
　Change from baseline subject-reported rTNSS and iTNSS for each day (AM, PM and average of AM and PM).
　TNSS—First 4 Weeks, Subjects Aged ≥2 to <6 Years:
　Change from baseline in average AM and PM subject-reported 12-hour rTNSS over the first 4 weeks of treatment for subjects aged ≥2 to <6 years.
　Change from baseline in average AM and PM subject-reported 12-hour iTNSS over the first 4 weeks of treatment for subjects aged ≥2 to <6 years.
　TNSS—First 4 Weeks, Subjects Aged ≥2 to <12 Years:
　Change from baseline in average AM and PM subject-reported 12-hour rTNSS over the first 4 weeks of treatment for subjects aged ≥2 to <12 years.
　Change from baseline in average AM and PM subject-reported 12-hour iTNSS over the first 4 weeks of treatment for subjects aged ≥2 to <12 years.
　Additional Total Nasal Symptom Score (TNSS) outcomes will be assessed for the following (e.g. AM, PM, Individual symptoms):
　12 weeks, subjects aged ≥6 to <12 years.
　12 weeks, subjects aged ≥2 to <6 years.
　12 weeks, subjects aged ≥2 to <12 years.
Physician Assessed Nasal Symptom Score (PNSS):
　Change from baseline in PNSS and physician assessed individual nasal symptoms at Weeks 4 and 12.
Pediatric Rhinoconjuntivitis Quality of Life Questionnaire (PRQLQ):
　Individual domains of the PRQLQ at Weeks 4 and 12.

Example 15

Phase III Clinical Study of Fixed Dose Combination of Mometasone and Olopatadine Nasal Spray in Pediatric Patients This study is a double blind, randomized, parallel-group 14 day study to evaluate the efficacy, safety, and tolerability of a fixed dose combination of mometasone furoate and olopatadine hydrochloride nasal spray compared with a placebo nasal spray over 14 days in pediatric subjects (aged 6 to under 12 years) with seasonal allergic rhinitis (SAR).

Study Objectives

To compare the efficacy of mometasone furoate and olopatadine hydrochloride nasal spray (administered as 1 spray per nostril twice daily) with a placebo nasal spray for treatment in pediatric subjects (aged ≥6 to <12 years) with SAR.

A secondary objective is to compare the safety and tolerability of mometasone furoate and olopatadine hydrochloride nasal spray with a placebo nasal spray over the study period.

Key Subject Selection Criteria
　Male or non-pregnant female subjects aged ≥6 to <12 years, at the Screening Visit (Visit 1).
　Documented clinical history of SAR (for at least 2 years preceding the Screening Visit [Visit 1]) with exacerbations (clinical evidence of active symptoms) during the study season for the relevant seasonal allergen (tree/grass pollen). SAR must have been of sufficient severity to have required treatment (either continuous or intermittent) in the past, and in the Investigator's judgment, is expected to require treatment throughout the study period.

Demonstrated sensitivity to at least 1 seasonal allergen (tree/grass pollen) known to induce SAR through a documented positive skin prick test (wheal diameter at least 5 mm greater than the negative control) to a relevant seasonal allergen. Documentation of a positive result within 12 months prior to the Screening Visit (Visit 1) is acceptable. The subject's positive allergen must be consistent with the medical history of SAR. Additionally, the subject is expected to be adequately exposed to the SAR allergen that he/she has tested positive for the entire duration of the study.

A 12-hour reflective Total Nasal Symptom Score (rTNSS) value of ≥6 (out of a possible 12) for the morning (AM) assessment at the Screening Visit (Visit 1).

Study Design

A total of approximately 450 subjects (≥6 to <12 years) will be randomized in the study in a 1:1 ratio for a fixed dose combination of mometasone furoate and olopatadine hydrochloride nasal spray (225 subjects) versus placebo nasal spray (225 subjects).

The treatment groups are provided in the table below.

Investigational Products and their Administration

| Investigational product(s) | Administration |
| --- | --- |
| Olopatadine hydrochloride + mometasone furoate (665 μg + 25 μg) nasal spray* | 1 spray per nostril, twice daily (BID) in morning and evening |
| Placebo nasal spray | Placebo - 1 spray per nostril twice daily (BID) in morning and evening |

*Each spray provides 665 μg olopatadine hydrochloride and 25 μg mometasone furoate.

The subject participation may be 22 days up to 27 days with 7 to 10 days of a screening/run-in period and 14 days of treatment period, with allowable window periods for the study visits.

Key Evaluation Criteria (Clinical Endpoints):
Primary Endpoint
  Change from baseline in average AM and PM subject-reported 12-hour reflective Total Nasal Symptom Score (rTNSS) over the 14 day treatment period.
Secondary Endpoint(s):
  Change from baseline in average AM and PM subject-reported 12-hour instantaneous Total Nasal Symptom Score (iTNSS) over the 14 day treatment period.
  Change from baseline in the overall Pediatric Rhinoconjunctivitis Quality of Life Questionnaire (PRQLQ) score on Day 15 (Visit 4) between treatment groups.
  Change from baseline in average AM and PM subject-reported 12-hour reflective Total Ocular Symptom Score (rTOSS) over the 14-day treatment period.
Other Efficacy Endpoint(s):
Nasal Symptoms
  Change from baseline in AM subject-reported rTNSS over the 14-day treatment period.
  Change from baseline in AM subject-reported iTNSS over the 14-day treatment period.
  Change from baseline in PM subject-reported rTNSS over the 14-day treatment period.
  Change from baseline in PM subject-reported iTNSS over the 14-day treatment period.
  Change from baseline in subject-reported reflective individual nasal symptoms over the 14-day treatment period (AM, PM and average of AM and PM).
  Change from baseline in subject-reported instantaneous individual nasal symptoms over the 14-day treatment period (AM, PM and average of AM and PM).
  Change from baseline in average AM and PM subject-reported rTNSS and iTNSS for each day.
  Change from baseline in AM subject-reported rTNSS and iTNSS for each day.
  Change from baseline in PM subject-reported rTNSS and iTNSS for each day.
Ocular Symptoms:
  Change from baseline in average AM and PM subject-reported instantaneous Total Ocular Symptom Score (iTOSS) over the 14-day treatment period.
  Change from baseline in AM subject-reported rTOSS over the 14-day treatment period.
  Change from baseline in AM subject-reported iTOSS over the 14-day treatment period.
  Change from baseline in PM subject-reported rTOSS over the 14-day treatment period.
  Change from baseline in PM subject-reported iTOSS over the 14-day treatment period.
  Change from baseline in subject-reported reflective individual ocular symptoms over the 14-day treatment period (AM, PM, and average AM and PM).
  Change from baseline in subject-reported instantaneous individual ocular symptoms over the 14-day treatment period (AM, PM, and average AM and PM).
  Change from baseline in average of the AM and PM subject-reported rTOSS and iTOSS for each day.
  Change from baseline in AM subject-reported rTOSS and iTOSS for each day.
  Change from baseline in PM subject-reported rTOSS and iTOSS for each day.
Non-nasal symptoms will be assessed in a similar manner to the ocular symptoms above (as described in the Statistical Analysis Plan [SAP]).
Physician Assessed Nasal Symptom Score (PNSS):
  Change from baseline in PNSS and physician assessed individual nasal symptoms at Day 15 (Visit 4).
Pediatric Rhinoconjuntivitis Quality of Life Questionnaire (PRQLQ):
  Change from baseline in individual domains of the PRQLQ at Day 15.

Although the invention herein has been described with reference to particular embodiments, it is to be understood that these embodiments are merely illustrative of the principles and application of the present invention. It is therefore to be understood that numerous modifications may be made to the illustrative embodiments.

All publications, patents, and patent applications cited in this application are herein incorporated by reference to the same extent as if each individual publication, patent, or patent application was specifically and individually indicated to be incorporated herein by reference.

We claim:

1. A method of treating allergic rhinitis and/or symptoms associated therewith in a human in need thereof comprising nasally administering to the human an effective amount of a fixed-dose pharmaceutical composition comprising mometasone furoate and olopatadine or its salt, in a weight ratio of from about 1:12 to about 1:53, wherein (i) the composition is nasally administered as 1 or 2 sprays per nostril, at least once daily, (ii) the pharmaceutical composition has a pH between about 3.3 and about 4.1, and (iii) each spray comprises olopatadine hydrochloride equivalent to about 600 mcg of olopatadine and about 25 mcg to about 50 mcg of mometasone furoate.

2. The method of claim 1, wherein the composition comprises mometasone furoate and olopatadine or its salt in a weight ratio of about 1:13.3 to about 1:26.6.

3. The method of claim 1, wherein the symptoms are selected from nasal symptoms.

4. The method of claim 3, wherein the nasal symptoms are selected from nasal congestion, rhinorrhea, itching and sneezing.

5. The method of claim 1, wherein the allergic rhinitis is seasonal allergic rhinitis.

6. The method of claim 1, wherein the allergic rhinitis is perennial allergic rhinitis.

7. A method of treating allergic rhinitis in a human in need thereof comprising nasally administering to the human an effective amount of a fixed-dose pharmaceutical composition comprising mometasone furoate and olopatadine or its salt, wherein (i) the composition is nasally administered as 1 or 2 sprays per nostril of the human at least once daily, (ii) each spray comprises about 25 mcg to about 50 mcg of mometasone furoate and about 600 mcg of olopatadine or its salt and (iii) the method provides reduction in at least one treatment-related adverse effect relative to the use of olopatadine alone.

8. The method of claim 7, wherein the composition comprises mometasone furoate and olopatadine or its salt in a weight ratio of about 1:13.3 to about 1:26.6.

9. The method of claim 7, wherein the treatment-related adverse effect is epistaxis.

10. The method of claim 7, wherein the symptoms are selected from nasal symptoms.

11. The method of claim 10, wherein the nasal symptoms are selected from nasal congestion, rhinorrhea, itching and sneezing.

12. The method of claim 7, wherein the allergic rhinitis is seasonal allergic rhinitis.

13. The method of claim 7, wherein the allergic rhinitis is perennial allergic rhinitis.

14. A method of treating allergic rhinitis and/or symptoms associated therewith in a human in need thereof comprising nasally administering to the human an effective amount of a fixed-dose pharmaceutical composition comprising mometasone furoate and olopatadine or its salt, in a weight ratio of about 1:12 to about 1:53, wherein (i) the composition is nasally administered as 1 or 2 sprays per nostril, at least once daily, (ii) each spray comprises olopatadine hydrochloride equivalent to about 600 mcg of olopatadine and about 25 mcg to about 50 mcg of mometasone furoate, and (iii) the composition has a total impurity content of no more than 1.0% after storage at about 25° C. and 60% relative humidity for a period of at least 6 months.

15. A method of treating one or more symptoms associated with allergic rhinitis in a human subject in need thereof comprising nasally administering twice daily, two sprays per nostril of a fixed-dose aqueous pharmaceutical composition comprising mometasone furoate and olopatadine hydrochloride, wherein (i) the composition has a pH between about 3.3 and about 4.1, (ii) each spray comprises about 25 mcg of mometasone furoate and about 665 mcg olopatadine hydrochloride, (iii) the composition contains less than 2% of crystallized olopatadine hydrochloride, based on the 100% total weight of olopatadine hydrochloride in the composition, after 3 months of storage at 25° C.±2° C. and 60%±5% relative humidity.

16. The method of claim 15, wherein the composition contains less than 2% of crystallized olopatadine hydrochloride, based on the 100% total weight of olopatadine hydrochloride in the composition, after 6 months of storage at 25° C.±2° C. and 60%±5% relative humidity.

17. A method of treating one or more symptoms associated with allergic rhinitis in a human subject in need thereof comprising nasally administering twice daily, two sprays per nostril of a fixed-dose aqueous pharmaceutical composition comprising mometasone furoate and olopatadine hydrochloride, wherein (i) the composition has a pH between about 3.3 and about 4.1, (ii) each spray comprises about 25 mcg of mometasone furoate and about 665 mcg olopatadine hydrochloride, (iii) the composition contains less than 2% of crystallized olopatadine hydrochloride, based on the 100% total weight of olopatadine hydrochloride in the composition, after 3 months of storage at 40° C.±2° C. and 75%±5% relative humidity.

18. The method of claim 17, wherein the composition contains less than 2% of crystallized olopatadine hydrochloride, based on the 100% total weight of olopatadine hydrochloride in the composition, after 6 months of storage at 40° C.±2° C. and 75%±5% relative humidity.

* * * * *